United States Patent
Shukla

(10) Patent No.: US 11,305,130 B2
(45) Date of Patent: Apr. 19, 2022

(54) DEVICES, SYSTEMS, AND METHODS FOR NON-INVASIVE CHRONIC PAIN THERAPY

(71) Applicant: NeuraLace Medical, Inc., San Diego, CA (US)

(72) Inventor: Shiv Shukla, San Diego, CA (US)

(73) Assignee: NeuraLace Medical, Inc., San Diego, CA (US)

( * ) Notice: Subject to any disclaimer, the term of this patent is extended or adjusted under 35 U.S.C. 154(b) by 0 days.

(21) Appl. No.: 16/920,637

(22) Filed: Jul. 3, 2020

(65) Prior Publication Data

US 2021/0001139 A1    Jan. 7, 2021

Related U.S. Application Data

(60) Provisional application No. 62/870,661, filed on Jul. 3, 2019.

(51) Int. Cl.
*A61N 2/00* (2006.01)
*A61N 2/02* (2006.01)

(52) U.S. Cl.
CPC .............. *A61N 2/008* (2013.01); *A61N 2/02* (2013.01)

(58) Field of Classification Search
CPC ... A61M 2005/3289; A61B 2562/0223; A61B 5/248; A61B 5/4848; A61B 5/4893; A61N 2/006; A61N 2/008; A61N 2/02
See application file for complete search history.

(56) References Cited

U.S. PATENT DOCUMENTS

| | | |
|---|---|---|
| 2009/0149736 A1 | 6/2009 | Skidmore et al. |
| 2010/0249577 A1 | 9/2010 | Schneider |
| 2014/0046423 A1 | 2/2014 | Rajguru et al. |
| 2018/0153430 A1 | 6/2018 | Ang et al. |
| 2018/0242865 A1 | 8/2018 | Yamagata |
| 2019/0192874 A1 | 6/2019 | Shukla |

FOREIGN PATENT DOCUMENTS

WO     2017132750 A1     8/2017

OTHER PUBLICATIONS

International Search Report and Written Opinion dated Oct. 9, 2020 for PCT application No. PCT/US2020/040835.

*Primary Examiner* — Christine H Matthews
(74) *Attorney, Agent, or Firm* — Mintz, Levin, Cohn, Ferris, Glovsky and Popeo, P.C.

(57) ABSTRACT

The present disclosure relates to sensing devices, systems, and their methods of use for aiding transcutaneous magnetic stimulation (tMS) therapy, such as for the treatment, alleviation, and the management of pain. The sensing device being configured for determining and measuring the efficacy thereof. Particularly, the present disclosure is directed to providing sensing devices, systems including the same, and their methods of use in identifying and targeting one or more sources of pain, such as chronic neuropathic pain, as well as for facilitating in the treatment thereof.

20 Claims, 14 Drawing Sheets

DEVICES, SYSTEMS, AND METHODS FOR NON-INVASIVE CHRONIC PAIN THERAPY

CROSS REFERENCE TO RELATED APPLICATIONS

The present application claims priority from U.S. Provisional Patent Application No. 62/870,661, filed Jul. 3, 2019, entitled "DEVICES, SYSTEMS, AND METHODS FOR NON-INVASIVE CHRONIC PAIN THERAPY", the disclosure of which is incorporated herein by reference in its entirety.

FIELD OF THE DISCLOSURE

The present disclosure relates generally to sensing devices, systems, and their methods of use for aiding in the administration of transcutaneous magnetic stimulation (tMS) therapy, such as for the treatment, alleviation, and the management of pain; the sensing device being configured for determining and measuring the efficacy thereof. Particularly, the present disclosure is directed to providing sensing devices, systems including the same, and their methods of use in targeting one or more sources of pain, such as chronic neuropathic pain, and for facilitating in the treatment thereof.

BACKGROUND OF THE DISCLOSURE

There are many different manifestations of pain. Pain can be psychological, such as caused by depression and stress, or bodily, such as due to a physical perturbation of a part of the body. In particular instances, bodily pain may be caused by direct engagement of the body with physical objects in the world. These types of acute pain are well known, and have been widely treated. Specifically, bodily pain is most often treated by the administration of an analgesic, such as acetaminophen. Additionally, non-steroidal anti-inflammatory drugs, like aspirin or ibuprofen, may be used to alleviate the sensation of pain and/or reduce inflammation.

However, in various instances, such as in extreme pain during post-surgery recovery, non-opioid analgesics may not be sufficient to bring about an alleviation in the experience of pain. In such an instance, opioid-based drugs like codeine or morphine and the like, may be administered. Nonetheless, because of the highly addictive nature of these drugs their use is highly regulated. Despite these ever increasing limiting regulations, opioid abuse remains a national epidemic that continues to claim the lives of tens of thousands of people every year. Particularly, it is estimated that in 2017 opioid abuse claimed the lives of about 72,000 sufferers nation wide.

Thus, when experiencing acute pain, a sufferer has very limited options for pain remediation. They can use an analgesic, such as acetaminophen or an NSAID, which may not be strong enough to relieve acute pain, or they may use an opioid, and risk the possibility of becoming addicted. In either instance, neither medicament is a good option when faced with chronic pain.

It has been found that chronic pain is physiologically different from acute pain. Specifically, acute pain is typically of sudden onset, usually the result of clearly defined underlying causes, such as bodily injury, e.g., cutting, piercing, pinching, tearing, and the like. Hence, healing the underlying cause typically resolves the pain altogether. In such instances, analgesics are administered as a stopgap for ameliorating the sensation of pain until the underlying injury can be healed.

Chronic pain, on the other hand, is different from acute pain. In certain instances, chronic pain can be provoked by an injury to nerve cells thereby initiating a pain pathway that often times generate pain signals that travel from the peripheral to the central nervous system. Particularly, once activated peripheral sensory nerves transmit pain messages to the Central Nervous System (CNS). Such pain is not easily resolved, and thus, it becomes chronic. Specifically, chronic nerve pain is difficult to treat, but if left untreated leads to biological cycles that only exacerbate the experience of pain. For many sufferers, chronic pain will never go away, may increase over time, and can lead to biological cycles that exacerbate pain. And as indicated herein, a problem with such pain is that treating it largely relies upon opioid use, which can in and of itself lead to addiction and death, as is widely reported today.

In various instances, the application of tMS has been found to reduce and/or ameliorate the sensation of chronic pain. However, there are some limitations to its usefulness. For instance, one such limitation is that it is difficult to successfully target and apply transcutaneous stimulation to the correct nerve cells that will be capable of beneficially responding to tMS. Other limitations are that it is difficult to deliver the tMS in an orientation that maximizes engagement, and at an intensity and duration to produce a reduction in pain intensity.

Particularly, there are two general types of pain that result from injury. These two different types of pain are the result of the conductance of pain sensation by different nerve cell types. The first type of pain sensation is acute, fast onset pain that is mediated by A nociceptive nerve fibers, e.g., A-β. The second is a duller, slow pain, mediated by C nociceptive nerve fibers. Hence, both of these A and C nociceptive nerve fibers are distinguishable by the speed at which they conduct signaling, resulting in two distinct sensations of pain: fast and acute as well as a slower more dispersed and duller sensation of pain.

Particularly, A and C fibers differ in the diameter and thickness of the myelin sheath that surrounds them, which affects the speed at which these neurons conduct nerve impulses. Specifically, the greater the diameter of the fiber and the thicker its myelin sheath, the faster the nerve cells will conduct nerve impulses. More specifically, A fibers have a larger diameter and are myelinated, and therefore conduct impulses quickly, while C fibers have a smaller diameter, are not myelinated, and conduct impulses more slowly. Accordingly, because of their differences in diameters and myelination, these different nerve fibers have been adapted to serve different functions. Consequently, when a part of the body is injured, the first pain felt is typically sharp, specific, and acute, mediated by A nerve fibers, while a few seconds later a more diffuse, dull pain mediated by C nerve fibers is typically experienced.

A fibers can be divided into three sub-categories including A-α fibers, which carry proprioception, or orientation, information, A-β, which carries information about touch, and A-δ, which carry information about pain, such as mechanical and/or thermal pain. C fibers also conduct information about mechanical and chemical, e.g., cold-sensation, pain, but with a slower conduction velocity. Accordingly, it is the difference between the speeds at which the two types of nociceptive nerve fibers (A-δ and C) conduct nerve impulses that distinguishes the two different manners in which pain is experienced when injured, the first, A-δ, is mediated by a fast-pain pathway that causes the immediate sharp, and acute pain, while C fibers form a slow-pain pathway that leads to the sensation of diffuse and dull pain.

Likewise, A-α fibers regulate the sensation of pain as related to one's muscles. However, there is another, lesser-known pain pathway that is mediated by an abridgement in homeostasis, which pain pathway is arbitrated by A-β. Particularly, when there is a homeostatic condition, e.g., in the absence of an acute pain-causing event, there is a concomitant lack of pain sensation everywhere in the body. Consequently, where pain is not felt, this absence of the sensation of pain is the result of a particular sensory nerve fiber, A-β, in that region that is constitutively active at a baseline level. The functioning of A-β, therefore, is to signal to the brain that homeostasis is good and to be maintained.

However, when that homeostatic condition is perturbed, pain is perceived when there is trauma or damage to the nerve that results in a diminution of activity below A-β's basal level. This decrease in activity signals to the brain that an injury to the body, at site of onset, has occurred and as a result the brain interprets this drop in activity as a traumatic event and therefore signals pain. The mechanism for this cause of action involves messaging from secondary, peripheral nerve fibers to the primary, first-order nerve fibers in the dorsal root ganglia.

More particularly, the dorsal root ganglia constitute a cluster of neurons that form at the dorsal root of the spinal nerve. These neurons include a collection of afferent axons that function to relay sensory information, in this instance, a decrease in peripheral sensory activity, e.g., of A-β, from the periphery to the central nervous system, e.g., brain, via the spinal cord. Specifically, when the peripheral A-β sensory touch fibers are active, the dorsal root ganglia (DRG) filters both A-δ and C fiber activity. However, when A-β activity diminishes, the filtering at the DRG switches off, and A-δ and C fiber signaling is then passed on to the central nervous system. Hence, it has been determined herein that A-β sensory inputs play a suppressive role for repressing A-δ and C fiber activity, and when that suppression is lifted, e.g., by a decreased activity of A-β, acute and/or chronic pain signaling is initiated.

These various nociceptive nerve fibers, including the A-α, A-β, A-δ, and C fibers form peripheral nerve fibers that include a collection of afferent axons that function to relay sensory information, e.g., secondary messaging, e.g., of pain sensation, from the periphery to the primary, first-order nerve fibers in the dorsal root ganglia, which constitutes a cluster of neurons that form at the dorsal root of the spinal nerve and conduct signals to the Central Nervous System (CNS), e.g., the brain via the spinal cord. Collectively, these nerve fibers have free nerve endings (nociceptors) that form dense networks with multiple branches connecting the peripheral tissues and organs to the spinal cord, and they respond only when a stimulus is strong enough to threaten the body's integrity, such as when a stimulus or event is likely to cause an injury.

Given this branching, over-lapping, dense network of axon fibers, which network includes a conglomeration of A-α, A-β, A-δ, and C fibers, as well as other peripheral and central nerve fibers, it is difficult to target magnetic stimulation to a particular site of injury in a specific nerve fiber at a determined orientation of application. Sensing the effects of that stimulation and monitoring those effects over time is even more difficult. However, such targeting and monitoring is important for effectively and efficiently ameliorating pain through magnetic stimulation. For instance, in a normal condition, when a portion of the body suffers an injury, A-β activity is down regulated, and A-δ and/or C fiber activity is increased signaling a pain response. When the body heals, homeostasis is re-established, A-β activity is increased, e.g., gradually, and the pain is diminished.

However, in some instances, such as when the nerves are traumatically injured, even though the body may heal, the nerves may not. Hence, in such an instance, e.g., of traumatic nerve injury, A-β activity remains down regulated, and because of this a chronic sense of pain remains ongoing. Accordingly, it is the A-β pain pathway, and its mechanism of action that creates and propagates chronic pain over time, and not the A-α, A-δ, and C fiber. Consequently, transcutaneous magnetic stimulation (tMS) has been found to reduce the intensity of the pain for a manageable period of time.

Particularly, provided herein below, is a tMS device that is configured for delivering magnetic stimulation to an A-β nerve, which is effective for reducing the sensation of pain when a magnetic impulse is received by the A-β nerve fibers in a manner so as to activate these fibers. Specifically, it has been determined that by preferentially stimulating A-β nerves, e.g., in the area of pain, A-β activity can be increased. This increase in A-β activity in turn down regulates the activity of A-δ and C fiber activity, thereby reducing the experience of pain.

Consequently, in view of the above, being able to preferentially apply the delivered magnetic pulse to A-β nerve tissues, rather than A-α, A-δ, and C fibers is very useful for treatment of chronic pain. Such stimulation is difficult to administer, however, because it is difficult to target A-β nerve fibers given the branching, over-lapping, dense network of A-α, A-δ, and C fibers that form the nerve tissues. This difficulty has been overcome by a number of different advancements in the field made by the inventor hereof. Particularly, presented herein are devices, systems, and their methods of use for the directed targeting and delivering of magnetic pulses to the A-β nerve, e.g., at the site of pain, such that the A-β fiber can be preferentially stimulated and/or monitored in a non-invasive manner.

Likewise, it has further been determined that when such magnetic stimulation is administered at a determined frequency, it can result in the activation of the A-β nerve, which, in turn, will result in the interruption of the pain response and a cessation of pain experience. More particularly, magnetic stimulation may be administered at a current density so as to create a voltage differential at the axon of the A-β fiber thereby activating the various voltage gated channels therein, which in turn, results in the activation of A-β and the down regulation of by A-δ and C fiber activity. Accordingly, provided herein is a device for the application of magnetic stimulation of the nerve cells, specifically the nerve cells associated with pain mediation, more specifically, A-β nerve fibers.

The sensing and monitoring of this stimulation is further complicated and made difficult because the A-β fiber is a fast conducting nerve fiber, whereby its signaling reaches the DRG prior to that of A-δ and C fiber activity. The sensing mechanism, therefore, has to be attuned so as to perceive activation despite the rapid conductance and transmission rates of the underlying nerve fibers, in a manner that the delivery of stimulation can be adapted and/or otherwise be orientated so as to not only preferentially target A-β fiber, but to also modulate the stimulation in response to changes in sensed nerve conditions. In a manner such as this, a cessation of the experience of pain can be achieved, such as via directive magnetic stimulation, so although one or more other nerve fibers may be stimulated, the rapid conducting A-β nerve fibers can be preferentially activated, and because of its fast conductance its activation dominates the interaction in a manner so as to cause a diminution in pain. Such stimulation may be generated in any suitable manner so as to activate the A-β nerve fiber, e.g., above its basal level, so as to increase the signaling that thereby down regulates the sensations of pain caused by the activation of A-δ and C fibers. For instance, such stimulation may be generated by the source of magnetic stimulation disclosed herein that activates the voltage-gated channels in the nerve fiber and/or depolarize the nerve cell, such as in minimally invasive manner.

However, as indicated, although effective for lessening pain, the activation of A-β nerve fibers with magnetic stimulation is difficult to achieve. Specifically, in order to generate stimulation of the A-β nerve so as to produce activation, it is useful for the magnetic stimulation to be finely tuned, orientated, and directed, which means that in applying the magnetic pulse, it is very easy to go off of the treatment site, miss the treatment site, and/or not hit it with the correct orientation. To overcome these difficulties, the development and use of the magnetic, sensing, and/or monitoring devices, systems, and their methods of use described herein have been advanced for overcoming these difficulties.

More specifically, in various embodiments, a mechanism for orientating a tMS device proximate an active region, e.g., a site of acute and/or chronic pain, such as within a determined range of effective administration of magnetic radiation, as well as the methods for delivering such radiation are provided. Additionally, provided are devices for sensing and/or monitoring the application of stimulation to a treatment site. Particularly, a mechanism, system, and method for identifying a treatment site of a subject, orientating a magnetic pulse delivery device to the treatment site, and administering magnetic radiation to the subject, is provided, such as where the mechanism further includes a sensing and/or monitoring device that is configured for sensing and/or monitoring the administration.

More particularly, the mechanism may include one or more of a positioning element, a tMS device, and a sensory and/or monitoring device that is configured to sense the nerves response to the magnetic stimulation and provide feedback to the system so as to more effectively target and direct the generated stimulation to the pain causing nerve of interest. Hence, although transcutaneous magnetic stimulation (tMS) has been found to reduce the intensity of pain for a manageable period of time, such administration of tMS is still in its infancy with respect to treatment efficacy, monitoring, and control, all of which are needed for systematizing tMS treatments.

Accordingly, embodiments of the systems of the disclosure provide greater observability of treatment activity, leading to better and more accurate control, thus leading to better treatment outcomes. Consequently, the devices, systems, and their methods of use as disclosed herein are effective for diminishing the experience of pain, and thus, represent a powerful replacement for the use of traditional opiates that have been found to be highly addictive, and can often lead to overdose and death, which is not a problem with the use of tMS application for pain amelioration.

SUMMARY OF THE DISCLOSURE

The present devices, systems, and methods accomplish these goals by providing for noninvasive pain amelioration therapy, including (but not necessarily limited to) a tMS application device having a magnetic coil, an automated positioning and tracking system that is programmed and/or configured to selectively position the magnetic coil of the tMS application device proximate a target area on a body of a subject experiencing neuropathic pain, and a tMS sensing device that is in communication with the tMS application device and positioning system, and functions to effectuate the targeting of magnetic stimulation to a discrete target site within the target area so as to deliver chronic pain therapy to a predetermined nerve in the subject in need of therapy.

For instance, in one aspect, a transcutaneous magnetic stimulation (tMS) device including a magnetic coil is provided, such as where the tMS device is configured as a magnetic stimulator. The tMS device may be coupled to the positioning element that is configured for assisting in the positioning and/or orientating of the tMS device so as to be proximate the site of treatment. This positioning and orientating may be effectuated through the use of a suitably configured tMS sensing and/or monitoring device, as described herein. In various instances, the tMS device, positioning element, and tMS sensing device may form a system that functions either manually or autonomously, such as through an associated controlling device.

Accordingly, in one aspect, presented herein is a transcutaneous magnetic stimulation (tMS) application device for delivering focused magnetic stimulation to a treatment site on a body of a subject. In various embodiments, the tMS application device may include one or more of the following. For example, the tMS application device may include a housing. The housing may have an extended body that includes a proximate portion having a proximate end, and a distal portion having a distal end. The extended body defines a cavity for retaining one or more components of the tMS application device.

The tMS applicator device includes a magnetic coil, such as an insulated magnetic coil disposed within the cavity of the proximate portion of the extended body of the housing. In particular embodiments, the magnetic coil may have a figure-8 arrangement and may include braiding wrapped around the figure-8 arrangement of the coil. The insulated magnetic coil may be configured for generating and delivering a focused magnetic stimulus at a determined pulse rate and having a determined amplitude. Likewise, the magnetic coil may be configured for receiving a determined voltage to push a selected current through the coil so as to generate the magnetic stimulus in a manner so as to produce a waveform having the chosen wave characteristics, e.g., amplitude, wavelength, and frequency, etc.

In various embodiments, the tMS device may include a cooling mechanism having a cooling element that is in communication with the magnetic coil. Particularly, the tMS applicator may include a cooling element for translating a fluid, such as from a reservoir of the cooling mechanism, to and from the magnetic coil in a manner sufficient to remove heat therefrom. Any suitable cooling agent may be used to flow through the cooling mechanism so long as it is capable of flowing through the translation conduits, e.g., tubing, and contacting the magnetic coil without breaking down, in a manner to absorb and translate generated heat away from the coils and into the reservoir. For instance, a carbon based, organic fluid may be employed, such as an oil based liquid, e.g., mineral oil.

Likewise, the reservoir may be associated with one or more cooling elements, such as one or more fans, such as 1, 2, 3, 4, or 5 or more fans, or other cooling elements that are capable of rapidly cooling the fluid in the reservoir prior to its return towards the magnetic coil. In particular embodiments, the cooling system may include one or more temperature sensors, e.g., thermometers, that are configured for detecting the temperature of the coils, and sending such coil temperature related data to the system control module so as to regulate the temperature of the coil. Specifically, the temperature may be regulated within a range of from about 15 degrees to about 60 degrees C., such as from about 20 degrees to about 40 degrees C., such as within a range between 25 to about 35 degrees C., including maintaining a temperate of about 30 to 35 to 40 degrees C. More specifically, the cooling system may be given a set point and may function to keep the temperature within the coil at the set point, such as below 46 degrees, or below 40 degrees C., or may be set to keep the temperature within a range, such that as the higher limit within the range the cooling system and/or other system parameters, e.g., voltage applied, current run, and/or duration of pulse length can all be modulated to keep the temperature within the set limits.

In particular embodiments, an imaging device may also be included. For instance, the tMS device, specifically, the tMS applicator may be associated with an imaging device, such as where the imaging device may be positioned proximate the housing of the tMS application device. The imaging device has a field whereby an image of a treatment site of the body to be treated relative to the tMS application device. Furthermore, in various embodiments, the imaging device may include a processing element for processing the captured images to produce processed image data, and may further include a communications module for transmitting the processed image data.

Additionally, the tMS application device may include a control module that may have a computing device that is configured to generate and control the generation of the magnetic stimulus. For instance, the control module may control the tMS applicator with respect to one or more of the voltage and current being employed in generating the magnetic stimulus as well as the pulse rate and amplitude of a waveform of the magnetic stimulus to be delivered by the magnetic coil. In such a manner as this, a finely catered tMS stimulus may be generated and delivered in a focused manner to the treatment site of the body of the subject.

Further, in another aspect, a transcutaneous sensing, imaging, tracking, and/or monitoring device is provided. The tMS sensing device may be configured for one or more of identifying a target site within a treatment area, determining a nerve of interest for the receipt of treatment, defining a topographical morphology of sub-cutaneous structures, nerve fiber s, and/or vessels within a given region of the body, e.g., surrounding the target nerve of interest, and communicating the same to a tMS system applicator and/or controller so as to more effectively target and facilitate the delivery of a magnetic field to an identified nerve fiber by a suitably configured tMS application device.

For instance, in various instances, a transcutaneous sensing and monitoring device is provided. Particularly, the transcutaneous sensing device may be configured for determining a reaction of a nerve to receipt of a magnetic stimulation applied to a target area. In particular instances, the transcutaneous sensing device includes a housing. The housing may have a plurality of sets of opposed surfaces that may be offset from one another by a boundary member. In such an instance, one of the surfaces of a pair of opposed surfaces may be configured to form a top surface and a corresponding other of the opposed surfaces forms a bottom surface. Together the plurality of sets of opposed surfaces and boundary member bound a cavity, such as where the cavity is configured for retaining one or more components of the sensing device.

For example, within the housing the sensing device may include one or more insulation and/or one or more sensor layers, such as where the sensor layer includes a number of sensing units formed of one or more sensor elements. Specifically, a first and second extended insulation layer may be included, such as where the first insulation layer may be positioned proximate the top surface of the housing, and the second insulation layer may be positioned proximate the bottom surface of the housing. Likewise, an extended substrate layer may be provided such as where the substrate layer is positioned between the first and second insulation layer. The substrate is configured for determining the reaction of the nerve to receipt of the magnetic stimulation.

More specifically, the substrate layer includes a plurality of sensing elements, which may be positioned along one or more surfaces of the substrate layers. Each sensing element may be configured for detecting a reaction in one or more nerve fibers to magnetic stimulation being applied by the tMS applicator to the target area so as to produce a response. The substrate may be in a variety of configurations and may include a plurality of components. For example, the substrate may include a printed circuit board that is coupled with the plurality of sensing elements. The printed circuit board contains one or more processing units, one or more memories, and a communications module. In particular embodiments, the processing unit is configured for receiving and processing the response data so as to produce processed response data. Further a communications module may be provided whereby the communications module is configured for transmitting the processed response data. An antenna unit may also be provided for enhancing data collection and transmission. Additionally, a surface member, such as a bottom surface of the housing, may include, or otherwise be associated with an attachment mechanism that is configured for coupling the transcutaneous sensing and monitoring device to a portion of a subject's body such as proximate the target area.

As indicated above, the tMS sensing device may be configured for interacting with a tMS applicator device for the purpose of identifying a response of a target nerve to an applied stimulation from the tMS applicator, and further configured for identifying one or more characteristics of the responding nerve. Particularly, the tMS sensing device may be configured for determining the morphology of one or more of an A-α, A-β, A-δ, and C nerve fiber, and can distinguish A-β from A-α, A-δ, and C fibers by their responsiveness to a magnetic pulse, and thus, can make targeting of an applied pulse from a tMS applicator to an A-β nerve fiber easier and more effective. Hence, in one aspect, the disclosure is directed to a system for identifying a target nerve and/or for administering magnetic stimulation to that target nerve for the purpose of treating neuropathic pain in a subject's body via the administration of catered magnetic stimulation.

For instance, the system may include one or more of a transcutaneous sensing and monitoring device, such as for identifying and/or mapping out a position of a nerve to be targeted, as well as a transcutaneous magnetic stimulation (tMS) application device for delivering focused magnetic stimulation to the identified target nerve, as described above. In particular instances the tMS application device is a tMS applicator that is part of a tMS application system. For instance, along with the tMS applicator, the tMS application system may include one or more control modules, having a memory, a processing element, and a communications module having one or more communications elements. Further, the tMS application system may include a positioning element.

Accordingly, in one aspect provided herein is a tMS application system for treating neuropathic pain in a subject's body via the administration of magnetic stimulation that includes, along with a tMS sensing and monitoring device and tMS applicator device, a control module and a positioning element. Specifically, the tMS system includes a transcutaneous sensing and monitoring device for identifying a nerve to be treated with magnetic stimulation, and a transcutaneous magnetic stimulation (tMS) application system for delivering focused magnetic stimulation to the identified nerve to be treated with magnetic stimulation. A control module and a positioning element, such as an automated positioning element may also be included.

For example, the control module may include a communications module for receiving the processed response data from the sensor module as well as the data therefrom that identifies and characterizes the identified nerve. A memory may also be included, such as a memory that is coupled to one or more of a processing element and the communications module, such as for storing the processed response data, the characterization of the nerve data, and one or more treatment protocols. As detailed herein below, the memory may be any form of onboard or detached memory.

The control unit includes one or more processing elements that are coupled to one or more of the communications module and the memory. The processing elements are configured for accessing the response data and the data characterizing the identified nerve from the sensing elements, and determining a treatment protocol to be administered to the subject for the treatment of neuropathic pain experience. The treatment protocol defines the application parameters and the delivery characteristics.

For instance, the one or more application parameters may include the voltage and current levels for generating the magnetic pulse of the magnetic stimulation. Further, the application parameters may include various parameters that characterize the waveform of the magnetic pulse to be generated, such as with respect to its wavelength, frequency, and duration. Likewise, the feedback received from the sensing elements of the various sensing units may be used to determine the one or more delivery characteristics.

Specifically, based on the degree, amplitude, and direction, e.g., magnitude, of the response of the nerve to the magnetic stimulation, the orientation and/or boundaries of the nerve may be determined. For example, the processing elements may perform a plurality of triangulation and/or trilateration functions so as to define a set of coordinates that define an area including at least a portion of the nerve to be targeted for treatment. More specifically, in addition, to the delivery characteristics, e.g., defining the location of the nerve to be treated, the one or more processing elements of the control unit may process the various sensed data from the response of the nerve to the applied magnetic pulse, e.g., its amplitude and magnitude, may perform one or more triangulation and/or trilateration operations on the data, and may determine one or more proposed orientation parameters that may define or otherwise be used for orienting the tMS application device relative to the target area.

Additionally, for example, once one or more orientation parameters have been defined, a positioning element may be employed so as to position the tMS applicator proximate the target area, and to orientate the applicator to the target nerve, such as in accordance with the determined orientation parameters. Accordingly the tMS application system may include a positioning element. The positioning element may have a proximal portion including a proximal end, and a distal portion including a distal end. In particular configurations, the distal portion may be coupled to the transcutaneous magnetic stimulation (tMS) application device, such as proximate the distal end, while the distal end may be coupled to a control module and/or to a support or grounding member.

The positioning element is composed of a plurality of articulating arm members that are configured for being moved and configured as necessary so as to position the tMS applicator in the determined orientation so as to achieve optimal activation of the target nerve. Further, in various embodiments, an automating element, such as one or more motors may be employed. Specifically, a plurality of the arm members may be coupled together by an automating element, which may be employed for automating the process of positioning and orienting the tMS application device proximate the treatment area in accordance with the determined orientation parameters of the treatment protocol.

Accordingly, in view of the above, a system is provided for identifying and characterizing a target nerve in an area proximate where a pain is being experienced. Both identifying and characterizing the nerve to be targeted may be an iterative process that involves applying a variety of magnetic pulses to the target area while moving the tMS application device, e.g., cm by cm, mm by mm, even micrometer by micrometer, in a variety of positions and orientations so as to determine what position and which orientation elicits the greatest response in pain reduction as experienced by the pain causing nerve. Hence, along with the tMS application device for applying a magnetic stimulation to a portion of a body so as to alleviate the experience of pain, a tMS sensing device may be provided whereby the tMS sensing device may be configured for being directly associated with the body of a person receiving treatment, such as by being attached to the skin proximate a treatment area.

Thus, as the tMS applicator applies a magnetic pulse to the target area, so as to provoke a reaction in a nerve to be treated, the attached tMS sensing device senses not only the magnitude of the response but also the amplitude and relative direction of the response. Specifically, for these purposes, the tMS sensing device may include one or more protective and/or substrate layers, one or more insulating and/or spacer layers, along with one or more sensing and/or data collecting layers. The sensing layers may include one or more sensor units, or other data collection units, and may include a communications module. The sensing and data collecting layer may further include one or more processing elements that is communicably coupled to the one or more sensing elements, whereby the processing element is configured for receiving and processing obtained, e.g., sensed, data.

In one aspect, therefore, provided herein is a system for identifying one or more characteristics of a neuropathic nerve to be targeted with an application of a focused magnetic stimulation so as to ameliorate neuropathic pain experience. So being, provided herein is a transcutaneous sensing and monitoring device that is configured for detecting a prospective nerve's response to the application of a magnetic stimulation as well as a computing device that is configured for analyzing sensed response data for the purpose of identifying and characterizing the identified nerve. Particularly, as recited above, the transcutaneous sensing and monitoring device may have a plurality of sensing elements, which may be configured in the form of a grid including both rows and columns of sensing elements. Any number of sensing elements may be provided such as in any number of rows and columns, depending on the size and orientation of nerve to be targeted, such as in 2, 4, 6, 8, 10, or more, or any number there between may be provided. Each sensing element is configured for identifying a reaction of a nerve in response to an applied magnetic stimulus so as to produce raw reaction data, which raw reaction data may include a magnitude and an orientation of the response of the nerve. Likewise, the transcutaneous sensing and monitoring device may include a communications module for transmitting the sensed raw reaction data.

Additionally, the system may include a computing device, such as a computing device that is part of or otherwise coupled to the transcutaneous sensing and monitoring device. As indicated, the computing device may be configured for receiving the raw reaction data, evaluating the raw reaction data, and determining one or more characteristics of the neuropathic nerve to be targeted. In various instances, the computing device includes a set of processing engines for processing the raw reaction data in a variety of manners using a plurality of different combinations of sensor elements so as to triangulate which sensor elements pick up the strongest responses and in what orientations.

For instance, a first processing engine, or set of processing engines, may be provided, such as for receiving the raw reaction data from a first unit of a plurality of sensing elements of the transcutaneous sensing and monitoring device. Particularly, the first sensing unit may include a first set of sensing elements, such as a first of at least two or three, or four or five, or six or more, sensing elements. A variety of raw data may be collected, such as raw reaction data that includes an amplitude, magnitude, direction, and/or orientation data, such as from each or a selection of sensing elements. This data may be in a raw form and may be used to characterize the response of the neuropathic nerve to the applied magnetic stimulus. In such an instance, the first processing element may be configured for integrating the direction, magnitude, and the orientation data from each of a selected set of sensing elements of the first sensing unit. Hence, the first sensing element or set of sensing elements may be configured for determining a first integrated magnitude and a first integrated orientation for the first unit.

Further, a second processing engine, or set of processing engines may be provided, such as for receiving the raw reaction data from a second unit of sensing elements. As per above, the second sensing unit may include a second set of sensing elements, such as a second set of at least two or three, or four or five, or six or more, sensing elements. Like above, the raw reaction data will include amplitude, magnitude, direction, and/or orientation data, such as from each or a selection of sensing elements, such as for further characterizing the response of the neuropathic nerve to the applied tMS stimulus. The second processing element, therefore, may be configured for integrating the direction, magnitude and orientation data from each of the sensing elements of the second sensing unit, and may further be configured for determining a second integrated direction and/or magnitude and a second integrated orientation for the second unit. These processes may be repeated for a number of different selections of sensing units including a number of different combinations of sensing elements, all producing a wide variety of sensor data having different strengths of magnitudes in different directions and having different orientations, such as in three-dimensional, X, Y, and Z space.

Furthermore, a third processing engine, or set of processing engines, may be provided for receiving the first and second, as well as any and all other integrated direction and magnitude data, and may further be configured for determining which collection of sensing units, and which sets of sensing elements thereof, evokes or otherwise evidences the greatest magnitude. The same or a different processing engine may then be configured for evaluating the sensed magnitude data and associating a weight to the evaluated data points, such as where greater weight is given to the sensing unit, as well as to the sensing elements thereof, evidencing the greatest results data, e.g., with respect to amplitude and/or magnitude of response. Lessor weighting may then be attributed to all the other sensing units and sensing elements.

Further still, a fourth processing engine, or set of processing engines, may be provided, such as where the fourth processing engine is configured for receiving the first and second and any additional integrated orientation, evaluating the same, and associating weights to individual data points, where a greater weight is given to whichever orientation is correlated with orientation data received by sensing elements of the sensor units evoking the greatest response, e.g., evidencing greater magnitude. Lessor weighting may then be attributed to all the other sensing units and sensing elements. A fifth processing engine, or set of processing engines, may also be present for receiving and evaluating respective integrated magnitude, integrated orientation, and other collected data, e.g., integrated direction and amplitude data, as well as the weight data for a plurality of sensing units, and determining a set of coordinates defining the neuropathic nerve to be targeted, such as based on the evaluated magnitude, orientation, other collected data, and weight data. A sixth processing engine, or set of processing engines, may be provided such as for determining a first treatment protocol for administering the focused magnetic stimulation to the neuropathic nerve to be targeted so as to thereby ameliorate neuropathic pain experience, such as where the first treatment protocol may include a proposed orientation of a tMS application device relative to the neuropathic nerve to be treated and/or an amplitude, or other waveform characteristic, of the focused magnetic stimulation to be administered.

Consequently, the sensing and communications units allow the tMS sensing device to sense or otherwise determine one or more changes to one or more nerve fibers, such as in response to a magnetic stimulation applied thereto, and for communicating the results thereof to an associated tMS system computing and/or controller device. The tMS sensing device may also include an amplifier, for amplifying received signal and/or transmitting the same, and may include an analog to digital converter, such as for converting analog signals, e.g., received from the stimulation of an activated nerve fiber, and converting the received signal to a digital representation thereof. Once processed the received data can be used to change one or more system parameters, such as to configure the system, and/or tMS application, so as to more effectively target the treatment area, and more specifically, target the nerve structures of interest.

In an additional aspect, a method for determining a treatment protocol for delivering a focused magnetic stimulation to a target nerve may be provided, such as where the nerve resides in a target area in a body of a subject experiencing neuropathic pain. The method may include one or more of the following steps. First, a transcutaneous sensing and monitoring device, as described above, may be coupled to the body, such as at an area of pain experience. The transcutaneous sensing and monitoring device may be configured for identifying a reaction of a nerve in response to an applied magnetic stimulus so as to produce an identified target nerve, and in some embodiments, the sensing device may include, or otherwise be associated with, a processing element that is configured for accessing sensor element data and determining, based on an evaluation of the sensor data, a proposed orientation for the tMS application device to be in, relative to the target nerve, so as to optimally focus the magnetic stimulation to the target nerve so as to more effectively provoke a therapeutic or prophylactic response in the nerve. In various embodiments, the proposed orientation may characterized by one or more parameters, such as coordinates in an X, Y, and/or Z direction, and/or with respect to latitude and longitude relative to a given marker.

Once the target nerve has been defined within interstitial space and/or a proposed orientation of the tMS applicator within ambient space has been determined, the transcutaneous magnetic stimulation (tMS) application device may be positioned proximate the target area, such as via activation of a robotic or mechanical positioning system. Specifically, the positioning system may include a positioning element that may have articulating arm members, and in such an instance, the method may include articulating one or more of the arm members so that a transcutaneous magnetic stimulation application device coupled to one or more of the arm members is positioned proximate the target area. During the positioning process, the method may further include orienting the tMS application device relative to the target area in accordance with the one or more parameters of the proposed orientation for magnetic stimulation delivery.

Once appropriately positioned and orientated, the tMS application device may be activated so as to generate and deliver a focused magnetic stimulus to the identified target nerve, such as when the tMS application device is positioned proximate the target area and in the determined orientation. Subsequent to the coupling of the tMS sensing device to the target area of the body and administration of the magnetic stimulus, the method may further include detecting, by the transcutaneous sensing and monitoring device, an activation of the identified target nerve in response to the delivery of the magnetic stimulus to the target area. A computing device, having one or more processing engines or elements, may then be employed to characterize the activation of the identified target nerve so as to produce characterization results data. In various embodiments the computing device may be an onboard computing element or may be otherwise coupled to one or both of the tMS sensing and monitoring device and the tMS application device. Additionally, the method may include determining, e.g., by the computing device, based on the characterization results data, a treatment protocol for the delivery of the focused magnetic stimulation to the identified target nerve.

A further aspect of the disclosure is directed to a method for determining one or more delivery characteristics of the focused magnetic stimulation to be administered to the target nerve in the target area in the body of the subject experiencing neuropathic pain, such as for alleviating the neuropathic pain experience. The method may include coupling the transcutaneous sensing and monitoring device to the body at the area of pain experience. As indicated above, in particular instances, the transcutaneous sensing and monitoring device may have a plurality of sensing units such as where each sensing unit includes a plurality of, e.g., at least tow or three, sensing elements that may be arranged so as to form a grid having both rows and columns of sensing elements, such as 2, 3, 4, 5, up to 10 or more rows and columns of sensing elements. Each sensing element may be configured for identifying the reaction of the nerve to the applied magnetic stimulation so as to produce raw reaction data, such as where the raw reaction data may include a direction, an amplitude, a magnitude, and/or an orientation of the response.

Once the sensing device has been coupled to the body, a magnetic stimulation may be applied, e.g., by a mobile tMS application device, to the area of pain experience in a manner so as to provoke a reaction in the target nerve in such a manner that a response thereto by the nerve to be targeted may be sensed by one or more of the sensing elements of the tMS sensing device. Accordingly, subsequent to applying a magnetic pulse to the target area, the transcutaneous sensing and monitoring device will collect the raw reaction data from the plurality of sensing units. The collected data may then be processed and evaluated, such as by a processing element onboard of the sensing device and/or by a computing device associated therewith, and the sensor element and sensor unit data, e.g., from a selection thereof, may be determined and integrated in such a manner that a plurality of integrated sensor unit data is produced. In such an instance, each individual and/or integrated sensor unit data may include an integrated magnitude and an integrated orientation of the response detected by the sensing elements, e.g., of each of the plurality of sensing units.

The computing device may then compare the integrated sensor unit data collected from a selection of the sensing units, one with the other, so as to produce a set of comparison results. The computing device evaluates the results of the comparison and then determines a treatment protocol for the delivery of the focused magnetic stimulation to the targeted nerve. For instance, in various instances, the treatment protocol may define one or more delivery characteristics, such as a set of coordinates defining the nerve to be treated and/or an orientation for orienting the tMS application device relative to the target area and/or target nerve. In particular instances, the computing device may determine one or more application parameters that may be used in generating the magnetic pulse. As indicated, the magnetic pulse may be engineered to have one or more determined waveform characteristics. In such instances, the one or more application parameters may include a voltage level and a current level, such as for generating a desired magnetic pulse, e.g., where the magnetic pulse is defined by a wavelength, frequency, amplitude, and duration of the magnetic pulse, which may all be selectable.

DESCRIPTION OF THE DIFFERENT EMBODIMENTS

Figure 1:
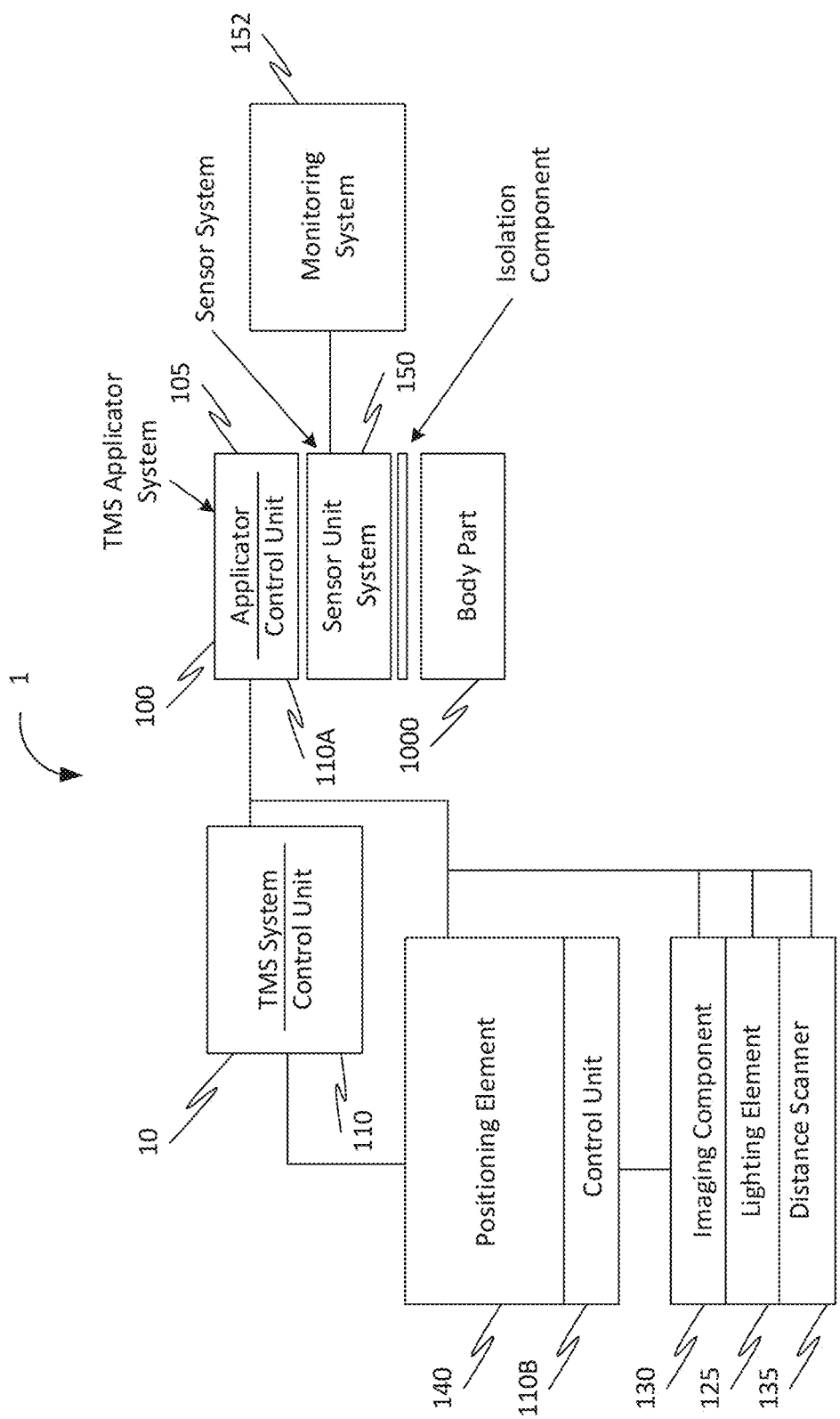
FIG. 1 provides a schematic representation of an embodiment of a system of the disclosure, the system including a Transcutaneous Magnetic Stimulation (tMS) application device that is coupled to a Transcutaneous Magnetic Stimulation (tMS) sensing and monitoring system.

Reference will now be made in detail to various embodiments of the subject matter, examples of which are illustrated in the accompanying drawings. Illustrative embodiments of the disclosure are described below. The details of one or more variations of the subject matter described herein are set forth in the accompanying drawings and the description below. Other features and advantages of the subject matter described herein will be apparent from the description and drawings, and from the claims. In the interest of clarity, not all features of an actual implementation are described in this specification.

It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Accordingly, while various embodiments are discussed herein, it will be understood that they are not intended to limit to these embodiments. On the contrary, the presented embodiments are intended to cover alternatives, modifications and equivalents, which may be included within the spirit and scope the various embodiments as defined by the appended claims. Furthermore, in the following Description of Different Embodiments, numerous specific details are set forth in order to provide a thorough understanding of embodiments of the present subject matter. However, embodiments may be practiced without these specific details. In other instances, well known methods, procedures, components, and circuits have not been described in detail as not to unnecessarily obscure aspects of the described embodiments.

The present devices and systems as well as the methods of using the same are provided for the purpose of reducing and/or ameliorating the sensation of pain, specifically, chronic pain. Particularly, in one aspect, the devices, systems, and their methods of use disclosed herein are effective for reducing peripheral nerve pain, such as resulting from traumatic nerve injury and other types of nerve damage. More particularly, treatment of peripheral nerve injuries by the application of transcutaneous magnetic stimulation (tMS) has been disclosed in U.S. Ser. No. 16/231,249, the contents of which are incorporated herein in their entirety by reference.

Specifically, an aspect of the present disclosure is the treatment of chronic, neuropathic pain typically caused by a reduction in the stimulatory effects of the A-β nerve fiber. However, delivering the desired dose of magnetic field application to the right region of the body, and more specifically to one or more isolated structures within a specific tissue of the body, is extremely difficult. Consequently, presented herein are devices, systems, and methods that are configured for delivering targeted therapeutic doses of magnetic pulses sufficient to increase the stimulation of A-β nerve fibers, while not substantially activating other nerve fibers, such as A-α, A-β, A-δ, and C fibers. This is not easy to accomplish, given that the nerve in need of treatment, A-β, is beneath the skin at some depth, and may be somewhat intermixed with other nerve fibers and/or other tissue structures.

Particularly, as indicated, although effective for lessening pain, the activation of A-β nerve fibers with magnetic stimulation is difficult to achieve. Specifically, in order to generate stimulation of the A-β nerve so as to produce activation therein, and consequently the reduction of the sensation of pain, it is useful for the tMS applicator, and the magnetic stimulation it provides, to be finely tuned, orientated, focused, and directed toward the target tissues of treatment. However, in applying a therapeutic magnetic pulse to a treatment area, it is very easy for the tMS applicator to miss the treatment site, go off of the treatment site, and/or not engage the treatment area with the correct orientation.

To overcome these difficulties, the development and use of magnetic sensing, monitoring, and/or tracking devices, systems, and their methods of use described herein have been advanced. Specifically, the application of tMS therapy relies on the fact that a changing magnetic field interacting with an electrically conductive nerve will induce current flow in the nerve, and thereby effectuate a reduction in the experience of pain. This induced current flow can alter the structure and operation of the nerve. However, the magnetic field needs to be received by the nerve fiber in a sufficient amount and/or quality and with an orientation that generates an appreciable effect in the nerve fiber, such as for pain reduction.

Particularly, in various instances, the magnetic field to be applied may be on the order of 1 to 3 Teslas, which is tens of thousands time more intense than the Earth's magnetic field. So being, to achieve this high level of magnetic field requires a large pulse of current, delivered over a very short time period, such as on the order of 100-500 microseconds. To date, pinpointing the exact location of the nerve in need of treatment often requires multiple attempts that are often random and non-repeatable.

Herein provided, therefore, are mechanisms and systems for determining the appropriate orientation of a tMS application device proximate an active region of pain generation, e.g., a site of acute and/or chronic pain experience, so as to better effectuate the application of a magnetic field to the site of pain by a suitably configured tMS applicator. Additionally provided are methods for administering one or more magnetic pulses to a nerve fiber within the tissues of the treatment area.

Particularly, provided herein are tMS sensing devices and systems including their use in the delivery of a magnetic field that is within a determined range of effective administration of magnetic radiation so as to be successfully received by a targeted pain causing nerve. Also provided are methods for delivering such radiation in the appropriate orientation and with the appropriate characteristics so as to cause activation of the nerve fiber and effectuate a reduction of pain within the nerve. More particularly, a mechanism, system, and method for identifying a treatment area of a subject, orientating a magnetic pulse delivery device to the treatment site, and administering magnetic radiation to the subject, are provided, such as where the mechanism further includes a sensing and/or monitoring device that is configured for sensing and/or monitoring administration of the magnetic field. Specifically, provided are systems and devices for sensing and/or monitoring the application of stimulation to a treatment site.

Accordingly, in one aspect, as illustrated in FIG. 1, a system 1 for delivering transcutaneous magnetic stimulation (tMS) to a treatment site on a body of a subject is provided. The system 1 may include a tMS system 10, a tMS applicator system 100, as well as a tMS sensing and monitoring device 150 of a monitoring system 152. The tMS applicator system 100 is configured for generating and directing a therapeutic magnetic field from a tMS applicator 105 toward a treatment area on a subject's body 1000 in need thereof. Along with the tMS applicator system 100, the system 1 may also include a positioning element 140, such as a robotic arm. Specifically, the tMS applicator 105 may be coupled to a distal portion of the positioning element 140, whereby the positioning element 140 is configured for orienting and/or positioning the tMS applicator 105 and/or magnetic coil 115 proximate the treatment area of the body 1000. The tMS system may include or otherwise be associated with a control unit 110. Additionally, one or more of the tMS applicator 105 and the positioning element 140 may further include individual control unit 110A and 110B.

For instance, the tMS applicator system 100 may include an individual control system 110A and, in various embodiments, the positioning element may include an individual control system 110B. Specifically, the tMS applicator device 105 may be coupled to a proximal portion of the positioning element 140 near the proximal end, and may include a control unit 110A that is configured for communicating with control units of the positioning element 110B and the tMS system control unit 100, and may be configured for controlling one or more of the tMS applicator device 105, the positioning element 140, the tMS system 10, an associated imaging component 130, a lighting element 125, and/or a distance scanner 135.

As indicated, the system 1 may also include a control module 110, for instance, a stand alone desktop or laptop computer, such as where the control module 110 serves as a master control unit for the system and is in communication with one or more of the tMS applicator control system 110A and/or positioning element controller 110B. Specifically, a master control unit 110, such as a computing device, may be included and configured for controlling the operations of one or more of the tMS applicator system 100, tMS applicator 105, and the positioning element 140.

For example, the system control unit 110 may control one or more operational parameters of the tMS applicator device 105 such as with respect to the generation and/or application of the magnetic field to be generated and applied by the magnetic coils 115 of the tMS applicator 105. In various instances, the system controller 110 performs this function by interacting cooperatively with the an onboard controllers of the tMS applicator 110A and/or the positioning element controller 110B, but in other instances, the system controller 110 provides direct control of the tMS applicator 105 and/or positioning element 140. Specifically, the control unit 110 may control the positioning element 140 with respect to its movements in three-dimensional space to finely determine and implement the appropriate orientation and configuration of the tMS applicator 105. This fine control may be exerted for the purpose of more effectively delivering a magnetic and/or electric pulse to an identified and targeted nerve tissue of interest.

Figure 3A:
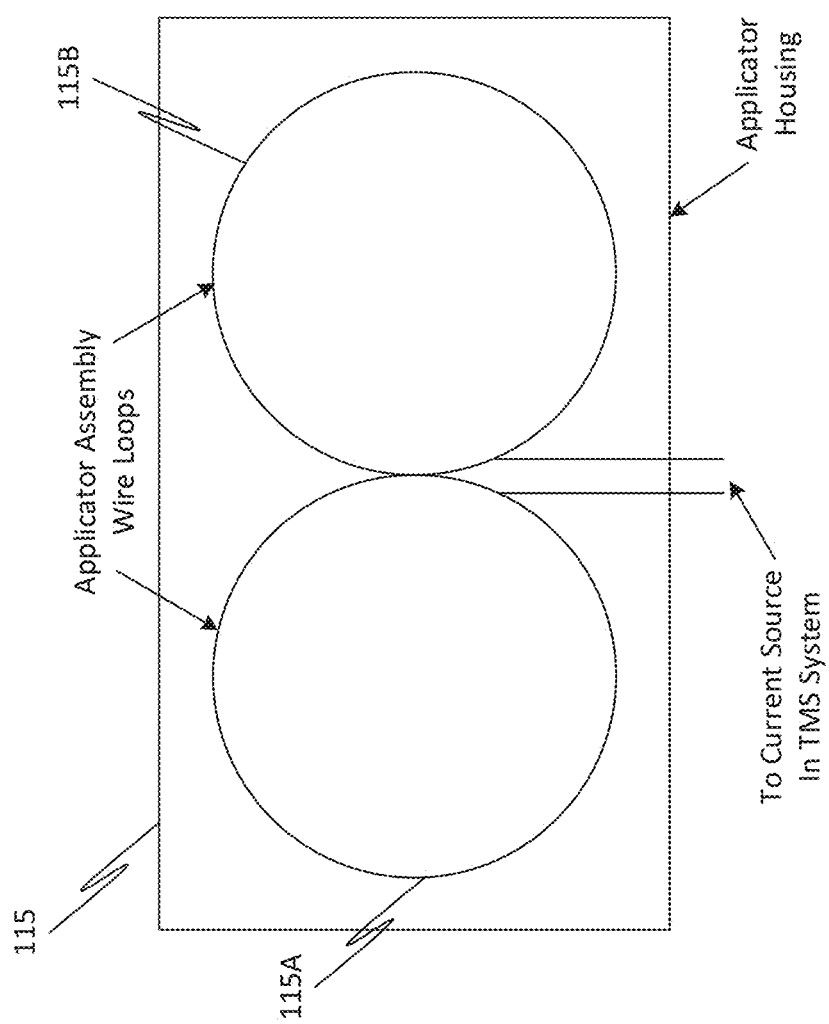
FIG. 3A provides a bottom up view of the magnetic coil of the tMS device of FIG. 2, where the magnetic coil has a figure-8 configuration.
Figure 3B:
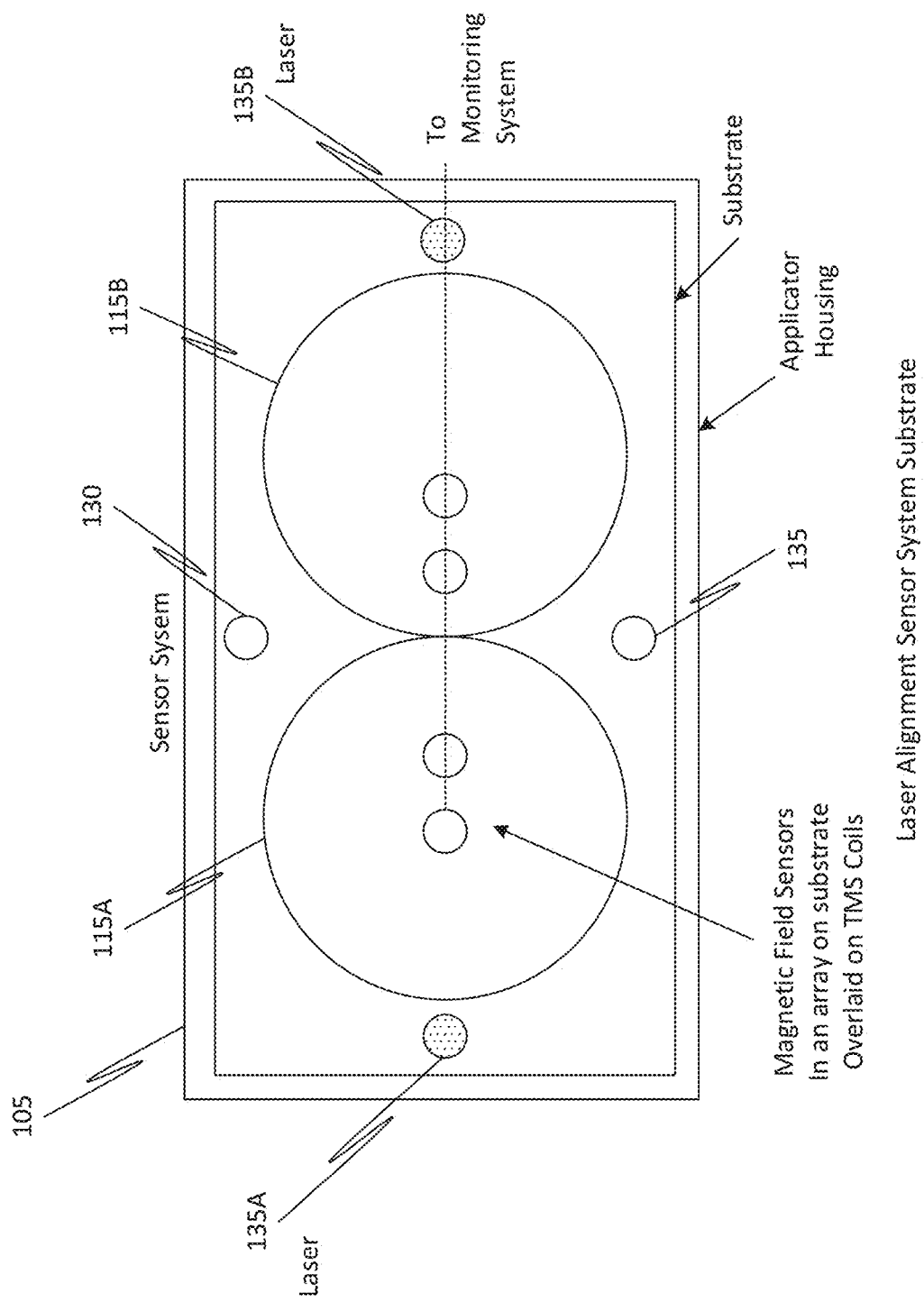
FIG. 3B provides a bottom up view of the magnetic coil of FIG. 3A, where the housing of the tMS applicator includes a plurality of laser tracking elements, and a plurality of magnetic field sensors, where the magnetic field sensors are overlaid on the magnetic coils.
Figure 3C:
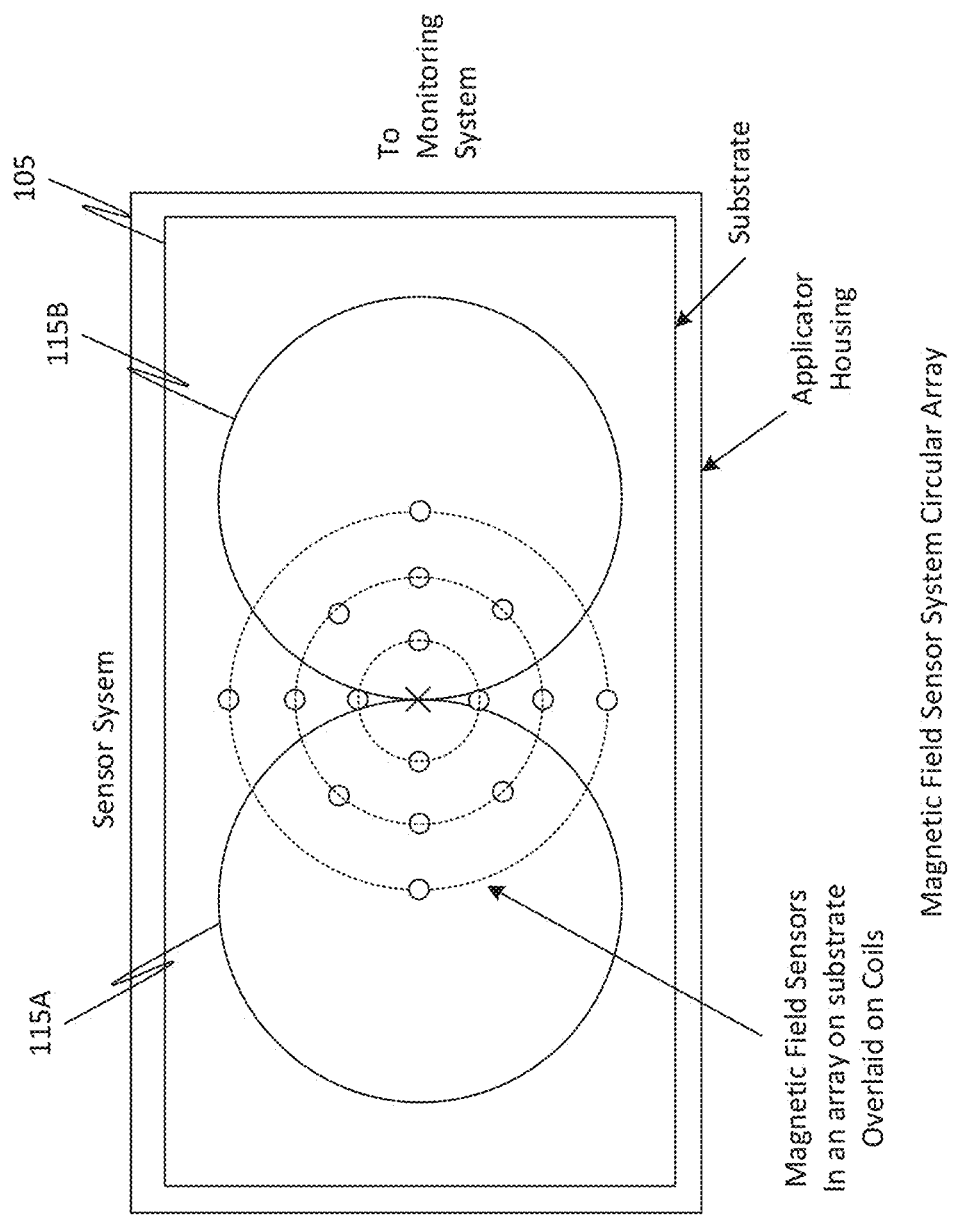
FIG. 3C provides a bottom up view of a magnetic coil having a plurality of magnetic field sensors, where the magnetic field sensors are arranged in a circular array.

To better effectuate delivery of the applied magnetic field, as can be seen with respect to FIGS. 3B and 3C, in various embodiments, the tMS applicator system 100 may include a distance determining device 135A and 135B and/or an imaging component 130, such as where the distance scanner 135 is configured for determining a distance between the tMS applicator 105 and the treatment area of the body 1000. In various instances, the distance scanner 135 may include one or more lasers for measuring distance and time. For instance, in certain instances, the distance scanner 135 may be a time of flight sensor.

Likewise, the tMS applicator 105 may include a lighting element 125 and an imaging capturing device 130, whereby the lighting element 125 may be configured for illuminating the targeting, while the imaging device 130 may be configured for capturing images of the illuminated structures within the tissues of the body in the target area. Likewise, as can be seen in FIG. 3C, a bottom up view of a magnetic coil 115 having a plurality of magnetic field sensors is provided, where the magnetic field sensors are arranged in a circular array. In various instance, this sensor array may be part of the tMS applicator 105, and/or may be a part of a cover 108 thereof, or part of a tMS sensing and monitoring device 150.

In various instances, the images being captured may be used by a computing device of the system for determining a condition of the surface area of the body 1000 in the target area. Further, in some instances, the images being captured may be employed for determining a condition of an interior structure within the tissue of the target area. In such instances, the placement, positioning, and orientation of the tMS applicator 105 and/or magnetic coil 115 may be accomplished through the cooperative interaction of one or more of: the positioning element 115, an image capturing device, 130, e.g., stereoscopic camera, a distance measuring device 135, e.g., micro laser and/or TOF distance scanner, and proprietary software instructions that are implemented by the system computing device 110 operating cooperatively in communication with the various other components of the system, such as the tMS device controller 110A, positioning element 140 and controller 110B, and tMS applicator 105.

As disclosed herein, it is useful to be able to modulate the generated magnetic pulse so as to optimize the treatments being applied to a subject in need of treatment. For instance, in configuring the magnetic pulse to be generated, there are many parameters that can be modulated within respect to the wave characteristics of the magnetic pulse and its mechanism of generation, such as the current running through the device, the voltage employed to push that current, the resistance incurred, and the duration of the current flow, as well as the frequency of the magnetic pulse and the amplitude of the wave. Other factors that can be adjusted with respect to configuring the system components, e.g., the voltage, current, etc., include both the inductance and capacitance as well as the resistance of the magnetic coils of the tMS application device.

Additionally, the positioning and the orientation of the tMS applicator, e.g., the magnetic coils, vis a vis the target site, can all be modulated so as to generate optimal administration conditions and/or for generating and delivering an optimal waveform. Consequently, the devices, systems, and their methods of use of the present disclosure will greatly improve application of non-invasive chronic pain relief therapy.

Accordingly, in various embodiments, the tMS applicator may include one or modulation units for modulating one or more of the voltage, the current, the amplitude, the frequency, duration, and the like, so as to allow more fine, rapid control of the pulse characteristics and/or delivery parameters. In certain embodiments, the modulation unit may work in conjunction with the tMS applicator controller so as to modulate the waveform, such as with respect to the amplitude of the magnetic stimulus, of the generated tMS stimulation. In various embodiments, the tMS applicator modulator may be a mechanical element to be pressed or scrolled.

However, in other instances, it may be a digital element configured for allowing a user of the tMS applicator to easily and rapidly modulate the various wave characteristics being applied by the application device, such as with the push of a button or toggle. In such a manner as this, the voltage, current, amplitude, frequency, wavelength, duration, and the like of the waveform can be changed, e.g., up or down, directly from the applicator device itself, without having to access the main control unit. For example, in particular instances, the power ranges to be employed in generating the current used in producing a magnetic field to be applied to a target nerve of interest may be variable.

For instance, pulsed voltage may range anywhere from 0, at rest, to about 4000V, such as from about 1000 or about 1500V to about 3500 or about 3000V, including about 2800V, which may be employed to drive currents, which currents may themselves range from 0 to about 6000 Amps, such as from about 1000 or about 2000 Amps to about 5000 or about 3000 Amps, including about 4,800 Amps in the Axon Coil. Likewise, the system may be configured, with respect to its component parts, e.g., the magnetic coil, includes inductance to be employed may range from about 5 or 10 Henries to about 40 or 30 Henries, such as from about 15 to about 20 Henries, including about 15.36E-6 Henries. Additionally, the coil may be configured, such as with respect to its composition and/or braiding, such that the resistance may range from about 400 to 1000 Ohms, such as about 600 to about 800.0E-6 Ohms, including about 700 Ohms. Additionally, the capacitance may range from 50 to about 200 farads, such as from about 100 to about 150 farads, including about 132E-6 farads, such as all while delivering a 282 microsecond pulse period. More specifically, modulating the voltage range may directly change the amplitude as a function of current while resistance remains constant. Changing the duration and frequency range of the firing of the SCR (silicon controlled rectifier) or similar thyristor, modifies the waveform characteristics.

Hence, if the depth of penetration of the magnetic pulse is desired to be increased or decreased from a current setting, there are a multiplicity of ways this can be achieved, one is by configuring the position and orientation of the applicator device, as explained in detail below. Another way the amplitude can be adjusted is by adjusting the waveform, such as by engaging with the aforementioned modulation units, such as to increase the amplitude, thereby making the penetration deeper, or decreasing the amplitude, thereby making the penetration more shallow. Specifically, the penetration can be modulated to increase the depth of penetration from the surface of the skin to about 1 or 2 cms deep, such as from 0.2 mm to 8 mm, including about 4, 5, or 6 mms deep, as described in greater detail herein below.

In certain embodiments, the voltage may be modulated such as from about 20 to about 100 mV, from about 40 to about 80 mV, including about 50 to 60 mV, such as over about 100 to about 500 micro seconds, such as about 200 to about 400 micro seconds, including about 300, e.g., 283 microseconds. Likewise, the amperage may be modulated such as from about 2000 to about 10,000 amps, such as from about 4000 to 6000 amps, including about 5000 amps, e.g., 5,500 amps, may be employed to push current through the treatment coils.

Additionally, as disclosed herein below with respect to FIGS. 5A-5C, the system 1 may additionally include one or more sensor systems 150 having one or more sensor devices or units 152, which sensor units 152 may include a plurality of sensor elements 160, such as magnetometers, atomic magnetometers, skin electrodes, and the like. Accordingly, in various embodiments, the tMS applicator device 105 may be employed in conjunction with, or otherwise include, one or more of a sensor and/or monitoring and/or tracking system 152. Particularly, a sensor system 150 may be provided, which sensor system 150 may include a number of different sensor elements 160 that may be configured for collecting data and feeding the same to one or more system control elements 110, such as for facilitating the targeting of a tissue to be treated, and directing the application of magnetic and/or electric stimulation to the targeted tissue 1000. In various embodiments, the sensor elements 160 may be configured for collecting biological and/or other data whereby one or more conditions of the body, e.g., nerves, of the subject being treated may be monitored and tracked.

Any suitable sensor capable of collecting and communicating collected data may be employed, and may include a magnetometer, atomic magnetometer, skin electrode, and the like, a light or sound emitter, an image capturing device, a light sensor, a temperature sensing device, a movement sensor, an orientation sensor, an accelerometer, and/or a number of other different sensing elements, which can be employed individually or collectively to assist in positioning the tMS applicator proximate a treatment site for the delivery of a therapeutic and/or prophylactic magnetic and/or electric impulse.

Accordingly, the system 1 may additionally include a positioning element 140, wherein the positioning element 140 is configured for assisting in the positioning and/or orientating of the tMS applicator 105 so as to be proximate the site of treatment and in the appropriate orientation to deliver one or more magnetic and/or electric pulses to the treatment area. This positioning may be performed manually or autonomously, such as through an associated controlling devices 110. For instance, the positioning element 140, may have a proximal portion including a proximal end, and a distal portion including a distal end, such as where the distal portion may be coupled to the tMS applicator 105, e.g., magnetic coil 115.

In such an instance, one or more of the proximal and/or distal portions may be associated with a controller 110B for effectuating the movements of the tMS applicator 105. In particular embodiments, the positioning element 140 may be composed of a plurality of articulating arm members, where the plurality of the arm members may be coupled together by an automating element, e.g., a motor in communication with the controller 110B. In various embodiments, the automating element may be configured for assisting in the positioning of the tMS applicator 105 proximate the treatment site.

Figure 2:
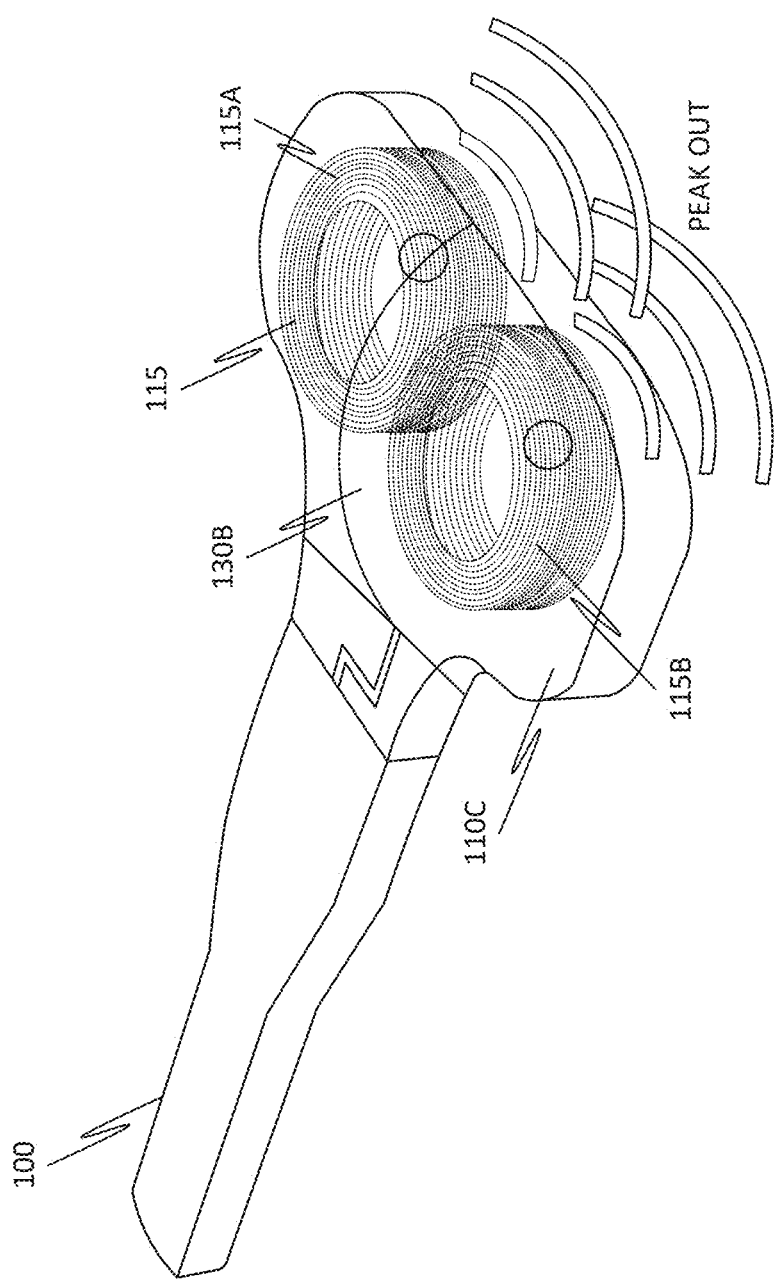
FIG. 2 provides illustrations of an transcutaneous magnetic stimulatory applicator of the disclosure having a plurality of magnetic coils in a figure-8 configuration.

Accordingly, in view of the above, as can be seen with respect to FIG. 2, herein presented is a transcutaneous magnetic stimulation (tMS) application device 105 for the delivery of a magnetic field to a target tissue. The tMS system 100 includes an applicator 105 that is configured as a magnetic stimulator, and therefore, includes a magnetic coil 115. Specifically, the tMS applicator system 100 is configured for delivering a focused magnetic flux to a treatment site of a subject when positioned proximate the body of the subject.

Hence, in one aspect, as summarized above, presented herein is a transcutaneous magnetic stimulation (tMS) system 100 including a tMS application device 105 for delivering focused magnetic stimulation to a treatment site on a body 100 of a subject. In various embodiments, the tMS application device 105 may include one or more of the following. For example, the tMS application device 105 may include a housing. The housing may have an extended body that includes a proximate portion having a proximate end, and a distal portion having a distal end. The extended body defines a cavity for retaining one or more components of the tMS application device 105.

The tMS applicator device 105 includes a magnetic coil 115, such as an insulated magnetic coil disposed within the cavity of the proximate portion of the extended body of the housing. In particular embodiments, the magnetic coil 115 may have a figure-8 arrangement and may include braiding wrapped around the figure-8 arrangement of the coil 115, as depicted in FIG. 3A. The insulated magnetic coil 115 may be configured for generating and delivering a focused magnetic stimulus at a determined pulse rate and having a determined amplitude. Likewise, the magnetic coil 115 may be configured for receiving a determined voltage to push a selected current through the coil so as to generate the magnetic stimulus in a manner so as to produce a waveform having the chosen wave characteristics, e.g., amplitude, wavelength, and frequency, etc.

In various embodiments, the tMS applicator system 100 may include a cooling mechanism having a cooling element that is in communication with the magnetic coil 115 of the tMS applicator 105. Particularly, the tMS system 100 may include a cooling element for translating a fluid, such as from a reservoir of the cooling mechanism, to and from the magnetic coil 115 in a manner sufficient to remove heat therefrom. Any suitable cooling agent may be used to flow through the cooling mechanism so long as it is capable of flowing through the translation conduits, e.g., tubing, and contacting the magnetic coil 115 without breaking down, in a manner to absorb and translate generated heat away from the coils and into the reservoir. Likewise, the reservoir may be associated with one or more cooling elements, such as one or more fans, such as 1, 2, 3, 4, or 5 or more fans, or other cooling elements that are capable of rapidly cooling the fluid in the reservoir prior to its return towards the magnetic coil 115.

In particular embodiments, the cooling system may include one or more temperature sensors, e.g., thermometers, that are configured for detecting the temperature of the coils, and sending such coil temperature related data to the system control module so as to regulate the temperature of the coil. Specifically, the temperature may be regulated within a range of from about 15 degrees to about 60 degrees C., such as from about 20 degrees to about 40 degrees C., such as within a range between 25 to about 35 degrees C., including maintaining a temperate of about 30 to 35 to 40 degrees C. More specifically, the cooling system may be given a set point and may function to keep the temperature within the coil at the set point, such as below 46 degrees, or below 40 degrees C., or may be set to keep the temperature within a range, such that as the higher limit within the range the cooling system and/or other system parameters, e.g., voltage applied, current run, and/or duration of pulse length can all be modulated to keep the temperature within the set limits.

In particular embodiments, an imaging device 130 may also be included with the applicator 105. For instance, the tMS system 100, specifically, the tMS applicator 105 may be associated with an imaging device 130B, such as where the imaging device 130B may be positioned proximate the housing of the tMS application device 105. The imaging device 130B has a field whereby an image of a treatment site of the body to be treated relative to the tMS application device 105. Furthermore, in various embodiments, the imaging device 130 may include a processing element 110C for processing the captured images to produce processed image data, and may further include a communications module for transmitting the processed image data.

Additionally, the tMS application system 100 may include a control module 110A that may have a computing device that is configured to generate and control the generation of the magnetic stimulus. For instance, the control module 110A may control the tMS applicator 105 with respect to one or more of the voltage and current being employed in generating the magnetic stimulus as well as the pulse rate and amplitude of a waveform of the magnetic stimulus to be delivered by the magnetic coil. In such a manner as this, a finely catered tMS stimulus may be generated and delivered in a focused manner to the treatment site of the body of the subject.

Accordingly, in one embodiments, as depicted, a handheld tMS applicator 105 may be provided and include a housing having an extended body, which includes a proximate portion having a proximate end, and a distal portion having a distal end. The extended body defines a cavity for retaining a plurality of components of the tMS device, such as a current generator positioned in the proximal portion of the applicator 105. As depicted, the a proximal portion of the tMS applicator 105 is configured as a handling portion that is adapted to be grasped by a handle positioned at an end section of the proximal portion. However, in various embodiments, the proximal portion is configured for being coupled to a positioning element 140, such as a robotic arm that functions to move and/or orientate the tMS applicator 105 and/or one or more of its coils 115.

Likewise, the insulated magnetic coil 115 may be disposed within the distal portion of the extended body of the housing, and may be configured for generating and delivering a focused magnetic flux with one or more determined characteristics, such as at a determined pulse rate. In various embodiments, a plurality, of magnetic coils 115A and 115B for generating and delivering the magnetic field may be provided. The plurality of magnetic coils may be spaced apart from one another by a distance sufficient to generate an electric field having an amplitude that is dimensioned to have a focal point whose peak output is centered proximate the center of the device, between the two coils.

The tMS system and/or applicator may also include a control module 110A and 110C that is in communication with the magnetic coils 115, which control module may be configured to control the focused magnetic flux, the pulse rate to be delivered by the magnetic coil 115 of the tMS applicator 105, and other waveform characteristics, so as to deliver a magnetic flux to the treatment site of a subject to be treated in a predetermined form. In various instances, the distal portion of the tMS applicator may have a right hand wing, having one magnetic coil 115A positioned therein, and may further include a left hand wing, having another magnetic coil 115B positioned therein, and may further include an articulating junction between the left and right hand coils, such as for moving the coils 115 one with respect to the other so as to adjust the focal point of the generated magnetic field and/or to control the configuration of the applicator 100, e.g., with respect to the body portion to be treated. Likewise, an articulating region may be positioned between the proximal and distal portions of the tMS applicator 100 so as to allow the distal portion to move relative to the proximal portion, so as to more precisely control the configuration of the applicator 105 coils 115. In particular embodiments, one or more of the articulating regions disclosed herein may include a motor unit, such as in communication with a controller of the system 110, such that the various configurations of the devices disclosed herein can be autonomously and/or automatically configured, such as in response to feedback received from a communicably coupled sensing device 150 of the system 1.

Figure 3D:
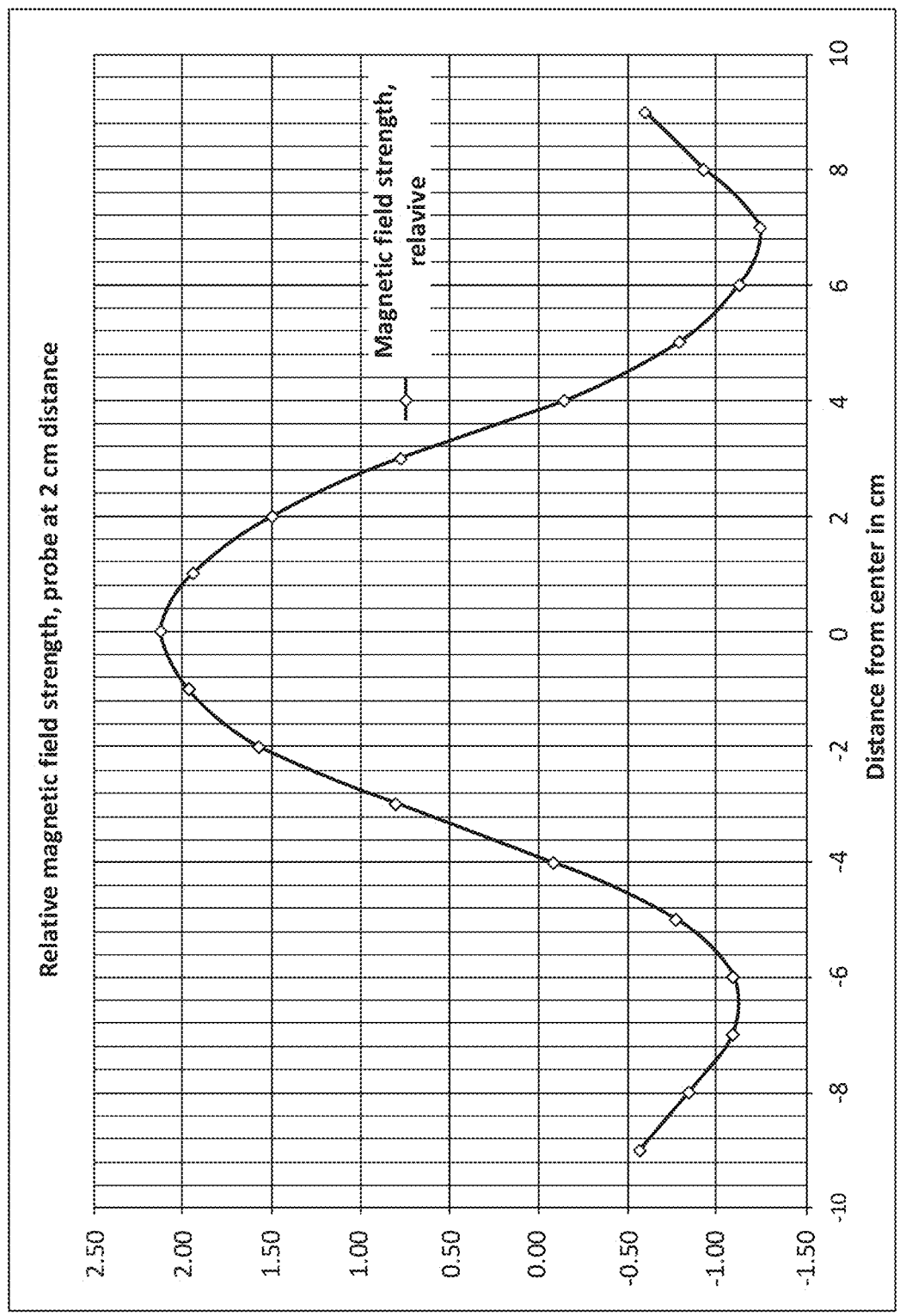
FIG. 3D provides a graphical representation of a representative magnetic pulse generated by the tMS device of FIG. 2.

As can be seen with respect to FIG. 2, in various embodiments, the distal portion of the tMS applicator 105 includes an applicator assembly having two conductive, e.g., wire, loops 115A and 115B through which a current may be run in a manner to generate individual magnetic fields. However, as can be seen with reference to FIGS. 3D and 3E, because there are two magnetic coils positioned proximate one another, as depicted in FIG. 3A, the two individual magnetic fields are generated such that a waveform having a centralized amplitude is created between them whereby the central amplitude may be focused and directed to a target treatment site, as depicted in FIG. 3D. For instance, the graphical representation of the magnetic field generated by the two coils 115A and 115B of the tMS applicator 105 includes two nadirs denoting the position of the center of each magnetic coil 115. Each magnetic coil generates an individual pulse in such a manner that the two respective magnetic fields reinforce and strengthen one another thereby forming an apical waveform that is centered midway between the center of the two coils, and thus, has an amplitude that is greater than could be produced by either coil alone.

Figure 3E:
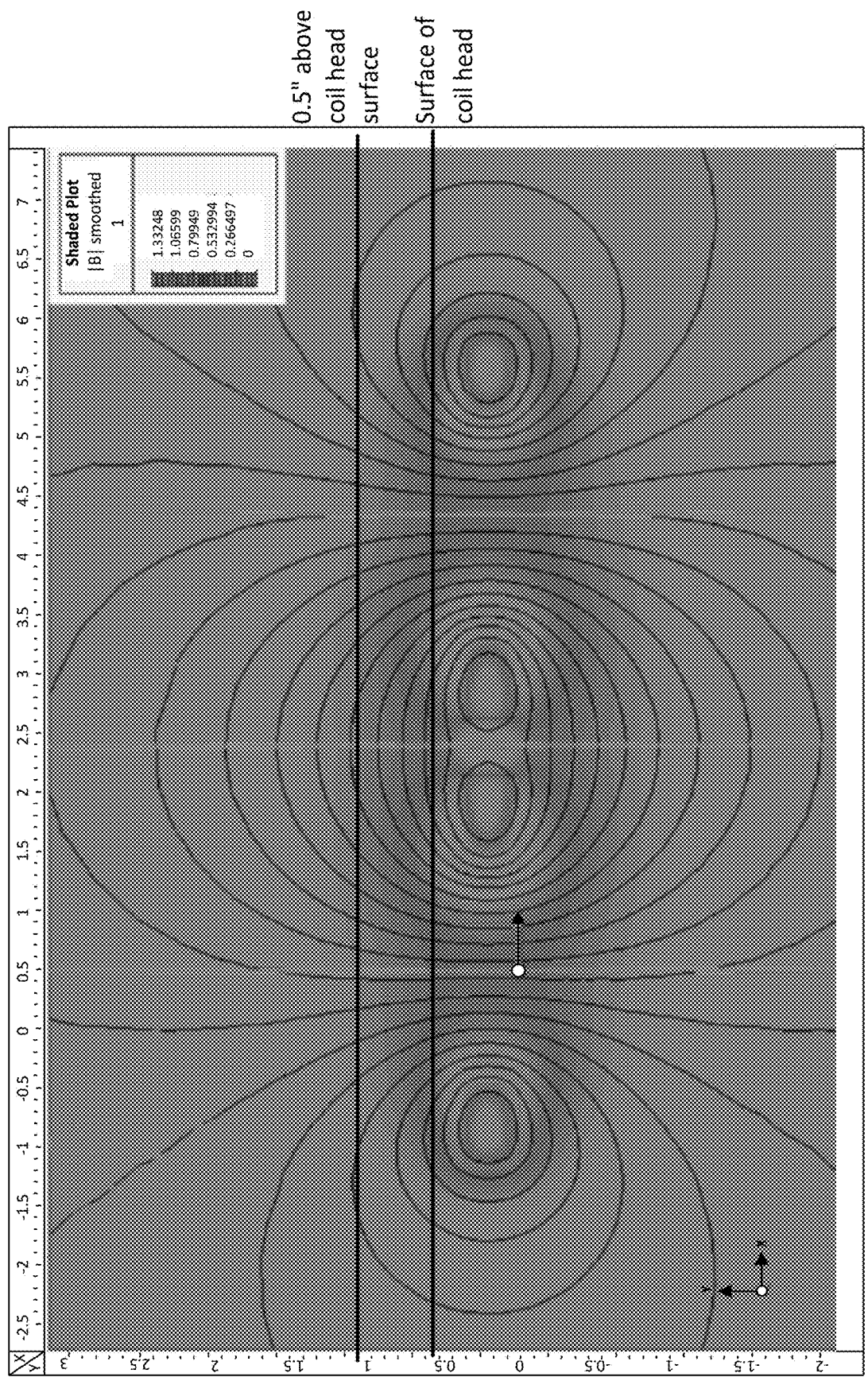
FIG. 3E provides a representation of the tMS device of FIG. 2 with regard to its generation of the magnetic pulse.

Particularly, FIG. 3E presents an image of the magnetic flux produced by the configuration of the figure-8 magnetic coil. Accordingly, in this manner, the waveform characteristics of the magnetic impulse, such as with respect to its amplitude, frequency, wavelength, and the like, may be controlled so as to deliver a focused magnetic pulse to an identified target tissue. Therefore, depending on the depth of the neuropathic pain causing nerve within the tissue, the amplitude, and other waveform characteristics of the generated waveform, may be modulated so as to target and provoke an optimized response from the targeted nerve cell. The configuration of the tMS applicator device and coil can also be manipulated, such as with respect to three-dimensional space, so as to also affect the waveform and/or penetration depth of the generated impulse.

Accordingly, as indicated, the system 1 may be configured for generating and delivering a magnetic impulse to a targeted area, and in some instances, an electromagnetic pulse may also be delivered, such as proximate an identified treatment target site. Particularly, in particular embodiments, a pulse may be generated and directed, e.g., in a diffuse or focused manner, to an area experiencing pain, such as pain caused by aberrant nerve activity. In some instances, however, in order to penetrate within the tissue and provoke the desired reaction in the target nerve, the tMS applicator may need to be positioned very nearly proximate, e.g., almost or actually touching, the target area. In such an instance, as can be seen with respect to FIGS. 4A and 4B it may be useful to include a sanitary covering, e.g., intelligent or smart cover, on the tMS applicator so as to ensure a sterile treatment administration. Hence, prior to the administration of the magnetic field to the area of pain sensation, a protective covering 108 may be positioned over the tMS applicator 105, such as shown between FIG. 4A, where the cover 108 has not been applied, and FIG. 4B, where the cover 108 has been applied.

In various embodiments, the cover 108 may be a smart cover configured as a single use hygienic covering that may serve to provide a protective sheath for covering a distal portion of the applicator 105, e.g., coil containing portion, which comes into proximity and/or contact with the body thereby ensuring sanitary conditions during use of the applicator 105. Further, the protective cover 108 may serve as an activator for the tMS device and system 1, such that prior to use, the covering 108 is required to be positioned over the distal portion head of the tMS applicator 105. Particularly, in various instances, the system 1 may include a tMS applicator 105, a sensor module 150, and/or protective covering 102 may be packaged as one or more collective or individual units.

For instance, in various instances, the tMS applicator 100 and/or sensor module 150 may include a covering element 108, e.g., a plurality of covering elements, one, which is configured to protect the one or more coils 115 of the tMS applicator, and another configured for covering the sensor elements 160 of the tMS sensing device 150. In this manner, the subject being treated may be protected in a hygienic routine. Accordingly, in a particular implementation, the covering 108 is configured for being coupled to the tMS applicator 105, and so being, serves to provide a hygienic interface between the tMS applicator 105 and the body tissues 1000 of the treatment area, so as to ensure any bodily contact with the tMS applicator 100 is performed in a sanitary manner.

Additionally, in various embodiments, the protective covering 108 in conjunction with the tMS applicator 105 and/or tMS sensor device 150 may be configured so as to ensure a one-time use functionality of the system 1, such as a one-time use of the tMS applicator 100 and/or tMS sensing device 150. For instance, the smart cover 108 may include circuitry 109 that is configured such that removal of the cover 108 from applicator 105 allows it to effectively operate, such as by switching it from an off or dead to an on or alive configuration. In a manner such as this, the system 1 may be configured for executing a pay-per-use model, such as for the tMS applicator 105 and/or sensor 150. For example, in particular embodiments, a one-time use functionality is implemented whereby the sensor 150 and/or applicator 105 may be used for a one treatment regime, and once employed cannot be deployed again until refurbishment.

In various other embodiments, the protective cover 108 may include a computer or machine activator 109 that is configured for authenticating the tMS applicator 105 and/or sensor device 150, such that when the cover 108 is placed over either of these devices, the cover 108 receives and/or transmits an access code, e.g., from the cover 108 to the device (or vice-versa), which access code authenticates the various system components thereby authorizing usability, e.g., for as long as the cover is coupled to the device. For example, one or more of the protective cover 108, the tMS sensor 150, and/or that applicator 105, may include an active and/or passive authentication coil 104 that is communicably coupled to a corresponding coil in the applicator and/or sensor such that when the two corresponding coils come into proximity with one another, a current is initiated, which current causes the authentication code to be transmitted, such as to a controller of the system thereby authorizing use.

In various embodiments, the protective cover 108 may include a battery, microprocessor, and/or transceiver such that in response to a received signal initiates a response, which in turn signals the activation of the system. More particularly, the protective cover 108 can include one or more engraved and/or wound-up mini-coils that form a circuit, which circuit can be activated to provide a current so as to power up the microprocessor and/or transmitter 109 to send an authentication code to the system controller 110. In a manner such as this, the protective cover 108 may be configured to not only authenticate and authorize use, but may further be configured to determine when a treatment regime is being administered as well as the nature of the magnetic and/or electric pulse being delivered.

In certain embodiments, the wound and/or engraved coil or other circuit within the protective cover 108 can be configured to burnout once a treatment pulse is delivered through the cover to the body thereby preventing further use of the sensor module and/or applicator after this one use. For instance, the coil can be electrically coupled to the transmitter, such as through a wired interconnect, which wire is configured to burnout, e.g., with the application of 30 mA, during first use, such that it can no longer activate the system during a subsequent use.

Likewise, one or more of the tMS applicator 100, the tMS sensor unit 150, and the protective cover 108 may include one or more magnetic field sensors. For example, the protective cover 108 may include a sensor configured for sensing the application of a magnetic and/or electric field impulse. And in various embodiments the sensing and monitoring unit 150 and/or applicator 105 and/or protective covering 108 may include a memory component.

Figure 4A:
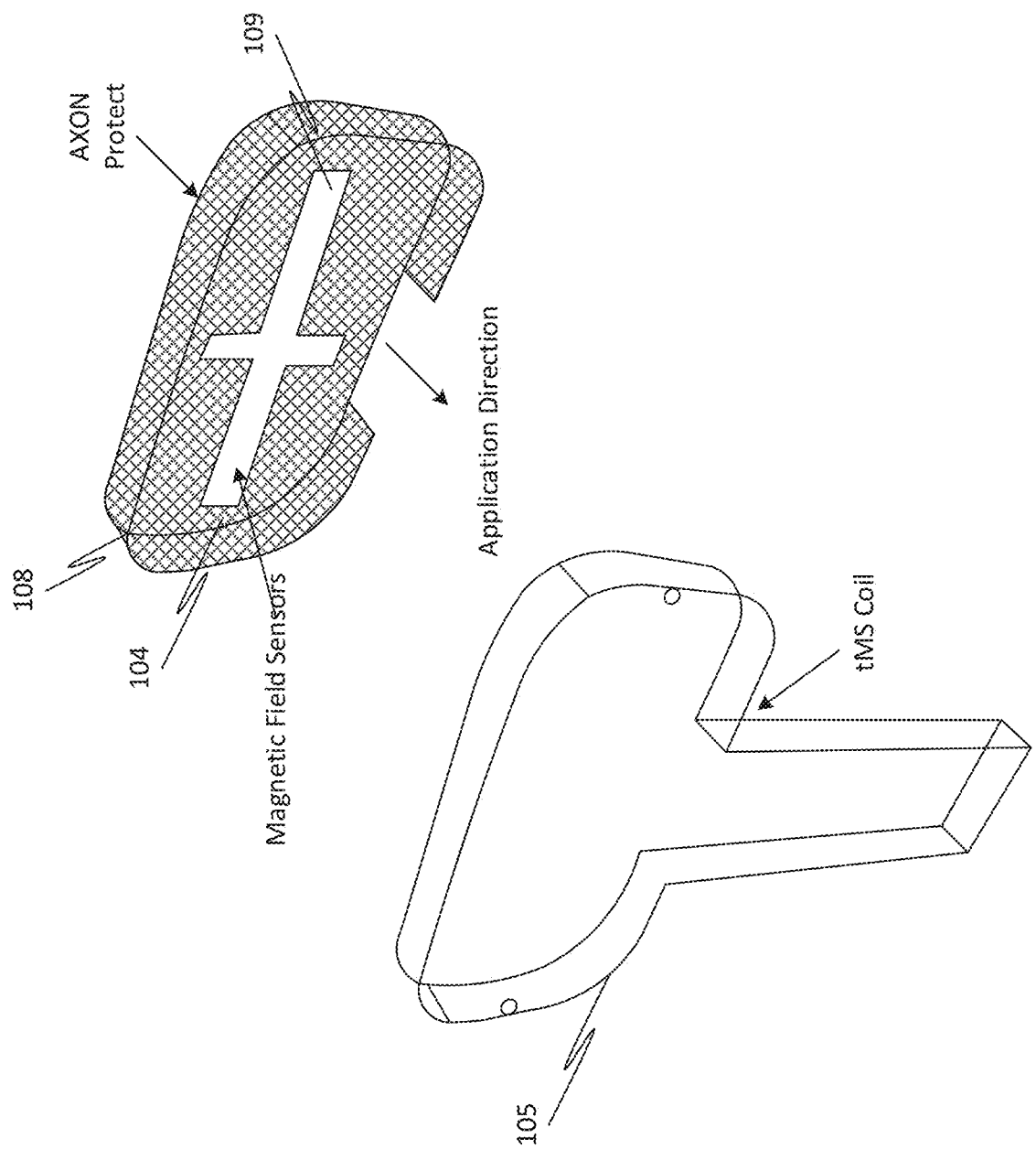
FIGS. 4A and 4B provides a perspective view of a smart cover for the tMS applicator of FIG. 2, in both an on and off configuration.
Figure 4B:
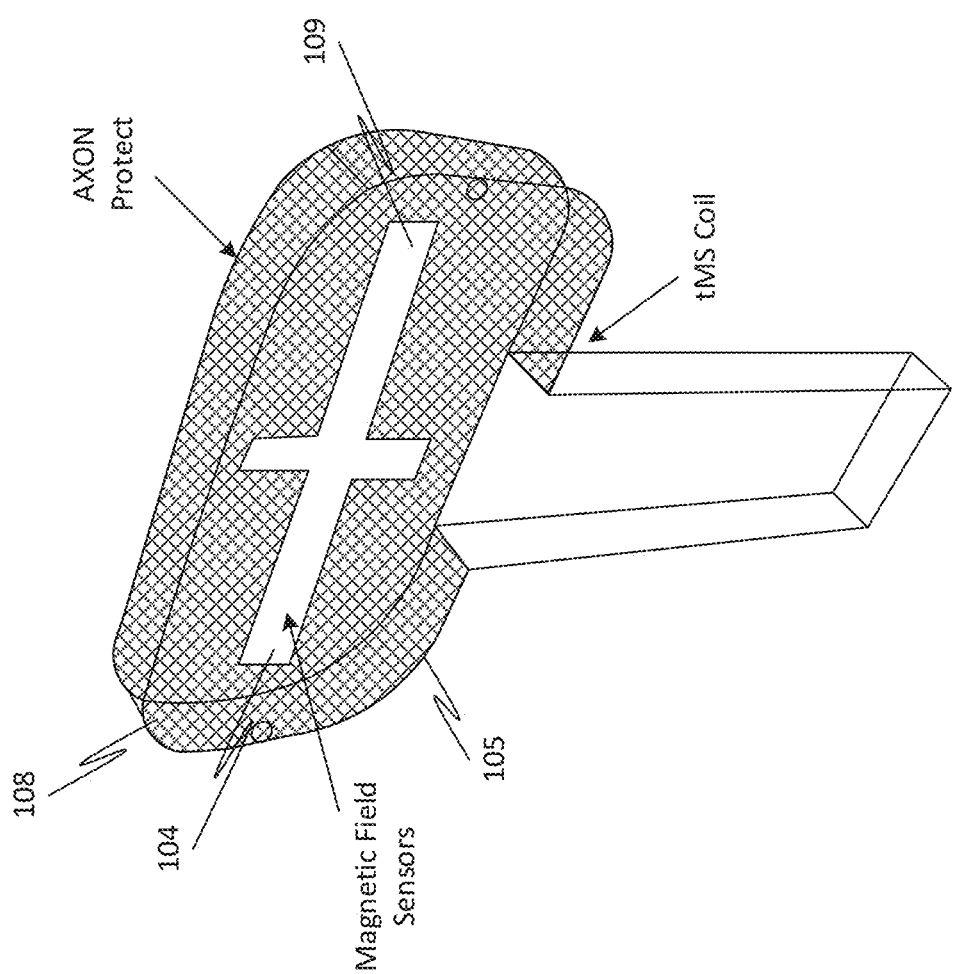

Accordingly, as can be seen in FIGS. 4A and 4B, in one use model, prior to application of the magnetic and/or electric field treatment, the protective cover 108 can be applied to the tMS applicator 105 (or tMS sensor 150), such as proximate the one or more coils 115 thereof, so as to form a protective, hygienic layer over the applicator between the treatment coils 115 and the tissue 1000 of the target area. Hence, once the protective cover 108 is positioned on the tMS applicator 105, one or more pulses may then be applied by the tMS applicator 105 so as to verify the quality and/or characteristics of the applied pulse, and/or to authenticate use parameters.

If an authenticating use is recognized, such as by activation of the passive coil, then the system can be authorized for treatment use. Consequently, the sensed magnetic pulse can be employed to authenticate the use of the tMS device 105, such as in a pay per use regimen. In such an instance, every time the device 105 is to be used, a new cover unit will need to be applied, such as to re-authenticate and unlock the next use, such as where the user must pay for each new protective cover to be used. Additionally, the cover 108 may include one or more sensors 104 that is configured for sensing and characterizing the applied pulse, such as to calibrate the magnetic field application.

In various embodiments, a tracking element may also be provided. The tracking element may be any element configured for facilitating the tracking of one or more components of the system 1, such as the sensing and monitoring 150 and/or tMS 105 devices. For instance, in various instances, the tracking element may be a reflective marker, such as provided by a marking pen or tape or the like. Particularly, in one embodiment, the tracking element may be a reflective tape of an appropriate size and dimension and/or formed in a selected configuration. For example, the tape may be a 3 mm×1 or 2 mm strip, which may be placed on an element, e.g., a sensor 10 or body portion of the subject to be tracked.

Accordingly, in view of the above, what is s needed is a sensing and/or monitoring system 100 for use in conjunction with and/or as a component of a tMS therapy system 1. Particularly, provided herein is a tMS application system 1 that includes a tMS applicator 105 that is configured for working in cooperation with a tMS sensor unit 150 and monitoring system 100, which devices function together for applying magnetic stimulation to a part of a subject's body in need thereof for the amelioration of pain, where the system is configured for targeting, efficacy monitoring, and fine-tuned control of tMS application. A benefit of this system 1 is greater observability of treatment activity, which increases control, so as to achieve better treatment outcome. Consequently, in one aspect, provided herein is an efficacy measurement and/or sensor system 100 and sensing device 150 that aids in the administration of transcutaneous magnetic stimulation (tMS) therapy.

Figure 5A:
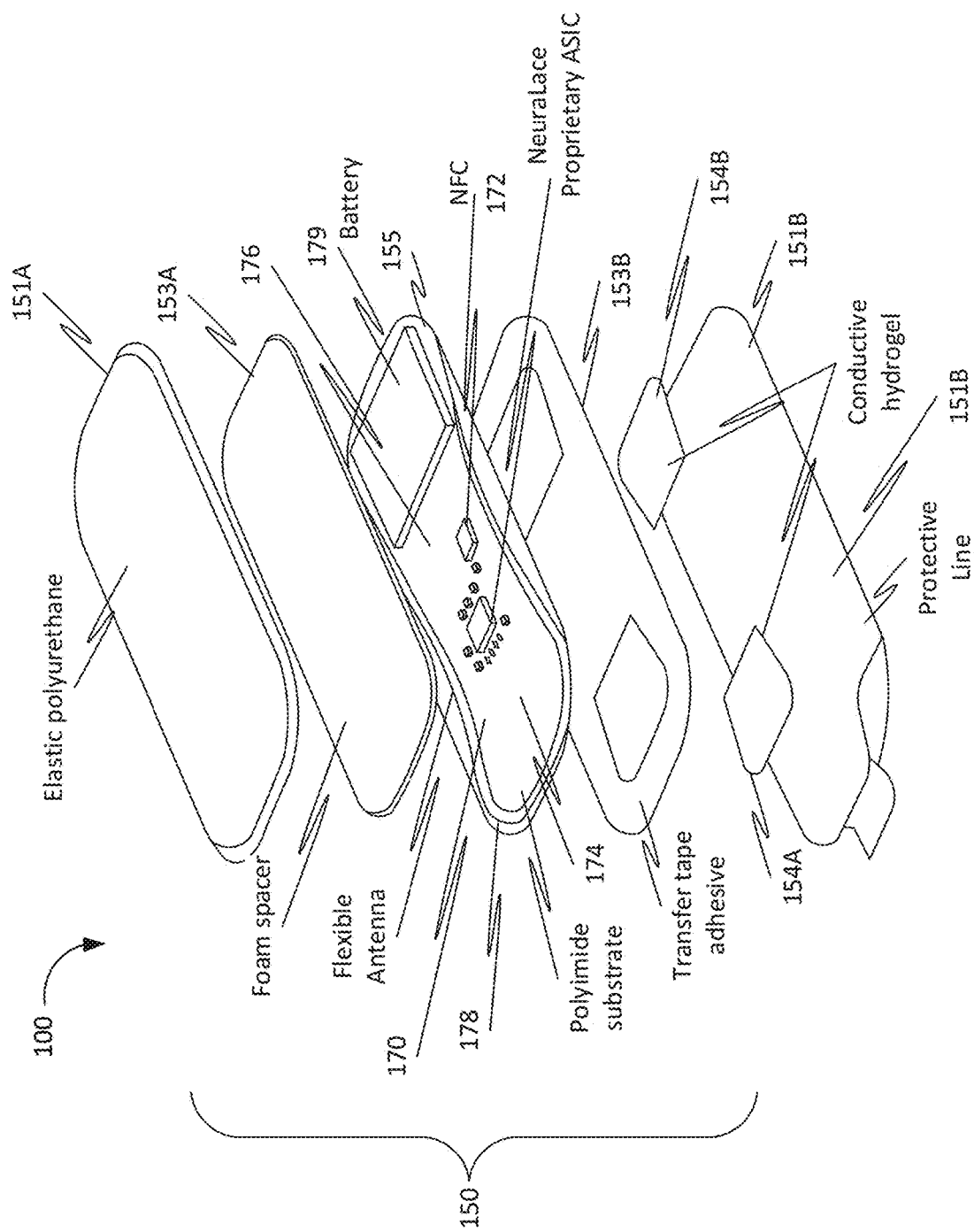
FIG. 5A provides an exploded view of a tMS sensing device of the system.

Specifically, as can be seen with respect to FIG. 5A, a transcutaneous sensing, imaging, tracking, and/or monitoring device 150 is provided, wherein the tMS sensing device 150 is configured for one or more of identifying a target site within a treatment area 1000, determining a nerve of interest for the receipt of treatment, defining a topographical morphology of sub-cutaneous structures and/or vessels within a given region of the body 1000 surrounding the target nerve of interest, and communicating the same to a system controller 110, so as to more effectively target and deliver the application of a magnetic field to the identified nerve fiber by a suitably configured tMS application device 105.

Particularly, the tMS sensing device 150 may be configured for interacting with a tMS applicator device 105 for the purpose of identifying a response of a target nerve to an applied stimulation from the tMS applicator 100, and further configured for identifying one or more characteristics of the responding structure. For instance, in various embodiments, the tMS sensing device 150 is configured for identifying the suspected morphology of one or more of an A-α, A-β, A-δ, and C nerve fiber. Particularly, in various embodiments, tMS sensing system 100 can distinguish A-β from A-α, A-δ, and C fibers, such as by their responsiveness to a magnetic pulse, and thus, can make targeting of an applied pulse from a tMS applicator to an A-β nerve fiber easier and more effective.

Hence, in one aspect, as can be seen with respect to FIG. 5A, the disclosure is directed to a tMS sensing device 150, whereby the sensing device 150 may be configured for operating in cooperation with a tMS applicator 105. Further, in some embodiments, the sensing device 150 may be adapted for being directly associated with the body of the subject, e.g., person, receiving treatment, such as by being attached to the skin of the body 1000 proximate a treatment area. In one embodiment, therefore, an attachable and wearable tMS sensing device 150 is provided, where in one implementation the tMS sensing device is disposable, whereas, in another implementation, the tMS sensing device 150 is configured for mid- to long-term use.

In either instance, the tMS sensing device 150 may include one or more of the following: one or more protective 151 and/or substrate layers 155, one or more insulating and/or spacer layers 153, along with one or more sensing and/or data collecting layers 155, which sensing layers may include one or more sensor units 160, or other data collection units, and may further include a communications module 170. Particularly, where the sensing and monitoring device 150 is a wearable device configured for long term use, the data collecting layer 155 may further include one or more processing elements 172 that is communicably coupled to the one or more sensing elements 160, whereby the processing elements 172 are configured for receiving and processing obtained, e.g., sensed, data. However, where the sensing device 150 is an attachable device configured so as to be disposable, the processing layer and/or processing elements 172 may be omitted from the device configuration.

For instance, in various embodiments, the processing function may primarily be performed by the tMS applicator controller 110A and/or an associated control unit 110, in which case the onboard processing functionality of the sensing device 150 may be minimized. In various instances, the sensing unit 150 and communications 174 unit may be included so as to allow the device 150 to sense or otherwise determine one or more changes to one or more nerve fibers, such as in response to a magnetic stimulation applied thereto, and for communicating the results thereof to an associated tMS system controller 110 to which the data may be offloaded and processed by the system 1.

Once processed the received data can be used to change one or more system parameters, such as to configure the system 1, and/or tMS applicator 105, so as to more effectively target the treatment area, and more specifically, target the nerve structures of interest. Particularly, the tMS sensing and/or monitoring device 150 may be configured for sensing a response of a targeted nerve fiber receiving treatment, and communicating response data to an associated tMS system controller 110, so as to configure one or more system components to better effectuate the application of treatments.

Accordingly, in certain instances, the tMS sensing device 150 may be configured for sensing a condition in the tissues 1000 being treated, and communicating data pertaining to that condition to an associated system controller 110 for processing thereby. This configuration is useful where the sensing device 150 does not include a processing unit 172, and is configured for being disposable. In such an instance, the sensor device 150 may include an adhesive, a biological glue, a clip on fastener, or other attachment mechanism.

However, in certain other instances, it is useful to have the processing functionality 172 closer to the wearable device itself, such as onboard, particularly, when the signals to be detected are weak and/or it is difficult to transmit. In such an instance, the device 150 may be configured for being worn for a prolonged period of time, such as one week to one month or more, and may include an onboard processing unit 172, and/or may include an amplifier so as to not only better effectuate the receipt and/or processing of sensed nerve activity, e.g., in a weak state, but for amplifying the received signal and/or transmitting the same, such as in an amplified state, to the system controller 110. For instance, in various instances, the received data may be in analog form, and the tMS sensing and monitoring device 150 may include an analog to digital converter, such as for converting analog signals, e.g., received from the stimulation of an activated nerve fiber, and converting the received signal to a digital representation thereof such as for transmission from the sensor device 150 to the controller.

As can be seen with reference to FIG. 5A, in various embodiments, a disposable, and in this instance wearable, tMS sensing, data collecting, monitoring and/or tracking device 150 is provided. In various embodiments, the tMS sensing device 150 may include a body forming a housing, such as where the body of the housing includes one or more, e.g., a plurality of, elongated, planar surface members 151A and 151B. For instance, the surface members 151A and 151B may be offset from one another by a circumferential surface member so as to form a thickness between the two planar surface members, e.g., a top surface 151A and a bottom surface 151B member, such that a cavity is produced between the top and bottom elongated surface members. In a particular embodiment, the top 151A and bottom 151B surface members may be configured for being coupled together so as to form a protective and/or waterproof housing for the device, such as where each housing member is composed of an organic polymer, such as a plastic, polycarbonate, polypropylene, polyurethane. In various instances, the housing may be composed of a rubber material.

For instance, as can be seen with respect to FIG. 5A, in various instances, a transcutaneous sensing and monitoring device 150 is provided. Particularly, the transcutaneous sensing device 150 may be configured for determining a reaction of a nerve to receipt of a magnetic stimulation applied to a target area. In particular instances, the transcutaneous sensing device includes a housing 151. The housing 151 may have a plurality of sets of opposed surfaces that may be offset from one another by a boundary member. In such an instance, one of the surfaces of a pair of opposed surfaces may be configured to form a top surface 151A and a corresponding other of the opposed surfaces forms a bottom surface 151B. Together the plurality of sets of opposed surfaces and boundary member bound a cavity, such as where the cavity is configured for retaining one or more components of the sensing device.

For example, within the housing 151 the sensing device may include one or more insulation 153 and/or one or more sensor layers 155, such as where the sensor layer includes a number of sensing units 152 formed of one or more sensor elements 160. Specifically, a first and second extended insulation layer 153A and 153B may be included, such as where the first insulation layer 153A may be positioned proximate the top surface of the housing 151A, and the second insulation layer 153B may be positioned proximate the bottom surface of the housing 151B. Likewise, an extended substrate layer 155 may be provided such as where the substrate layer is positioned between the first and second insulation layer 153. The substrate 155 is configured for determining the reaction of the nerve to receipt of the magnetic stimulation.

More specifically, the substrate layer 155 includes a plurality of sensing elements 160, which may be positioned along one or more surfaces of the substrate layers 155. Each sensing element 160 may be configured for detecting a reaction in one or more nerve fibers to magnetic stimulation being applied by the tMS applicator to the target area so as to produce a response. The substrate 155 may be in a variety of configurations and may include a plurality of components. For example, the substrate 155 may include a printed circuit board that is coupled with the plurality of sensing elements. The printed circuit board contains one or more processing units 172, one or more memories 176, and a communications module 174.

In particular embodiments, the processing unit 172 is configured for receiving and processing the response data so as to produce processed response data. Further a communications module 174 may be provided whereby the communications module is configured for transmitting the processed response data. An antenna 178 unit may also be provided for enhancing data collection and transmission. Additionally, a surface member, such as a bottom surface of the housing 151B, may include, or otherwise be associated with an attachment mechanism that is configured for coupling the transcutaneous sensing and monitoring device to a portion of a subject's body such as proximate the target area.

Accordingly, in various embodiments, the sensing, data collecting, and/or monitoring device 10 may be configured for being wearable. For instance, the top 151A or bottom 151B surface member of the housing 151 may be configured for being coupled, e.g., attached, to a body portion 1000 of the subject being treated via the application of a magnetic pulse. Accordingly, one or more of the housing members 151 may include an attachment mechanism, such as an adhesive, for attaching the sensing unit to the body. Where the tMS sensing device 150 is disposable it may include a removable attachment member, such as an adhesive, tape, clip, or other attachment. In particular embodiments, the tMS sensing device 150 may include one or more additional layers, such as intermediate layers 153, for instance, a spacer 153A and/or transfer layer 153B may be housed between the two protective housing members 151.

In various embodiments, one or more of the intermediate layers may further include or otherwise be configured as an adhesive layer. For instance, in one embodiment, one intermediate layer may be a foam or rubber spacing layer 153A, and another intermediate layer may be an adhesive transfer layer 153B. One or more of these intermediate layers may further serve as a non-conductive insulation layer, such as an insulation layer positioned proximate a top and/or bottom surface of the silicone PCB layer. In various embodiments, these layers are flexible and/or elastic, and are configured for making the device flexible and/or elastic.

Accordingly, a first, second, third, or more intermediate layers may be present. Particularly, in one instance, at least one of the intermediate layers includes one or more sensor units 152 thereby forming a sensor layer 155, which sensor unit 152 may be configured for sensing one or more conditions present within the tissue of the body to which the tMS sensing device 150 is coupled. More particularly, as can be seen with respect to FIG. 5B, the sensor device 150 may include a sensor unit 142 having one or more sensors 160 positioned on one or more of the intermediate layers 155. The sensor unit 152 may include one or more sensing and/or other data collecting elements 160.

In particular embodiments, at least one sensing and/or data collecting element 160 can be completely retained within an intermediate sensing layer 155, and/or in other instances, at least one sensing or data collecting element is coupled to one or more of the other layers, such as a top 151A or bottom 151B surface layer of the device 150. Particularly, in one embodiment, a portion of the sensor element 160 may be retained within the cavity, whereas another portion of the sensor element may be positioned at the top 151A or bottom 151B surface member. In various instances, a sensor portion may be positioned along a circumferential member.

The sensing element may be any sensing component that is capable of receiving data characterizing a response of a nerve to the application of a magnetic pulse applied thereto. Particularly, at the cellular level, neurons have electrochemical properties that when activated, such as by stimulatory encounter, lead to the flow of electrically charged ions, e.g., current, and subsequently generation of electromagnetic fields. The magnetic field generated by individual neurons, in a specific area, produces a field that is capable of being detected and measured, such as at the periphery. Accordingly, a useful sensing element for use in accordance with the descriptions provided herein is capable of making such measurement and determination. More specifically, in various embodiments, this neuromagnetic fields generated by a nerve fibers response to a stimulatory impulse may be in the range of 10-15 T (femtotesla, fT) for peripheral activities, and thus, the appropriate sensing elements should be finely tuned and very, very sensitive.

For these purposes, the tMS sensing and monitoring devices, disclosed herein, include an array of sensing elements that constitutes the backbone of a processing pipeline that forms a non-invasive assessment platform that is configured for detecting and determining an amplitude in a pain fiber in response to an applied magnetic field. In particular embodiments, the array of sensing elements are formed of an array of magnetometers, atomic magnetometers, skin electrodes, a combination of the same, and the like that are configured for measuring the direction, strength, magnitude, and/or relative change of a magnetic field associated with the electrical activity of the targeted A-β nerve fiber.

Accordingly, the sensor arrays and/or units disclosed herein provide a direct quantification and/or qualification of sensory nerve action potential amplitudes, sensory latency, and conduction velocity. The sensory nerve action potential amplitude may be measured in microvolts, and represents a measure of a number of axons conducting between the stimulation site, e.g., at the target area, and the recording site, e.g., where tMS sensing and monitoring device is positioned. Sensory latency, which may be measured in milliseconds, is the time that it takes for the action potential to travel between the stimulation site and the recording site of the nerve. Likewise, the conduction velocity, e.g., measured in meters per second, may be obtained by dividing the distance between stimulation site and the recording site by the latency: Conduction velocity=Distance/Latency. In view of the forgoing, in particular embodiments, an array of unit of sensing elements may be formed of at least three sensing elements, e.g., magnetometers, atomic magnetometers, skin electrodes, and the like, that are configured for receiving sensed data, which sensed data may be employed by one or more processing engines, so as to identify a pain causing target nerve, such as by performing one or more trilateration functions.

In various embodiments, the intermediate sensing layer 155 may be formed as a substrate layer, such as a polyamide substrate, where the substrate layer includes a printed circuit board member, e.g., flexible PCB, having one or more traces for creating one or more electric circuits between the various electronic components of the sensing, data collecting, and/or monitoring device 150. A variety of electronic components may be included, such as a processing unit 172, a memory 178, a communications module 174, a power source 179, and the like. For instance, a processing unit 172 including one or more integrated circuits may be included where the processing unit includes one or more processing elements, such as one or more of an application specific integrated circuits (ASICs) or field-programmable gated array (FPGA).

Particularly, the tMS sensing and monitoring device 150 may include a micro-controller or controller 172, such as a central processing unit (CPU), a graphics processing unit (GPU), a digital signal processor (DSP), one or more ASICs or FPGAs, one or more radio-frequency integrated circuits (RFICs), or any combination of these. This implementation is useful where processing is to be performed onboard. However, in various embodiments, the processing function 172 may primarily be performed off board by the tMS device 105 and/or an associated control unit 110, in which case the onboard processing functionality of the tMS sensing device 150 may be minimized, but the communications module 174 may be present for transmitting one or more of the sensed conditions to the control unit 110, such as via a WIFI, Bluetooth, NFC, or other wireless communications protocol.

Accordingly, a communications module 174 may be provided so as to allow communications, e.g., wired or wireless communications, between the sensing, data collecting, and/or monitoring device 150 and one or more of the tMS applicator 105, a control unit 110, and/or other computing device, such as via an internet and/or cellular (3G, 4G, and 5G) and/or WIFI, and/or Bluetooth, and/or NFC network connection. Consequently, in various embodiments, the tMS sensing and/or applicator devices and system may include a SIM card. A suitably configured router unit may also be included. In various embodiments, the communications module may be configured for implementing a Near-Field Communications (NFC) protocol. In particular instances, an analog to digital and/or digital to analog converter may be included. A signal amplifier may also be included.

A memory 178 device may also be included such as where the memory may be configured for storing the received data, and/or instructions for processing the same. In various instances, the memory may include any suitable type of storage device including, for example, ROM, such as Mask ROM, PROM, EPROM, EEPROM; NVRAM, such as Flash memory; Early stage NVRAM, such as nvSRAM, FeRAM, MRAM, or PRAM, or any other type, such as, CBRAM, SONOS, RRAM, Racetrack memory, NRAM, Millipede memory, or FJG. Other types of data memory can be employed as such are available in the form factor desired.

One or more antennas 178 may be included, such as a flexible, elongated antenna array, where the elongated antenna array includes one or more antennas that circumscribes at least a portion, e.g., the entire, circumference of the tMS sensing device 150. In various instances, at least one of the antennas in the array is configured for participating in wireless communications and/or signal amplification, and in particular instances, the antenna array may include one or more inductive coils, such as for charging a power source for the device.

Hence, a power source 179 may also be included such as where the power source includes a battery. For instance, the battery can be any type of battery, such as a rechargeable battery. The battery can be a thin, flexible lithium ceramic chemistry battery. In one embodiment, the battery can be a curved or otherwise formed lithium polymer or lithium ion battery. The battery is adapted so as to provide power to the other components of the device. In one example, the battery can be a lithium cell integrated directly with the flexible PCB 155 described above. In various instances, the battery is configured for being charged wirelessly. For example, in various embodiments, a power generation mechanism may be provided, such as where the power generator includes an electromagnetic induction charging coil, e.g., antenna, that is coupled to the battery and configured for performing inductive charging thereof.

Figure 5B:
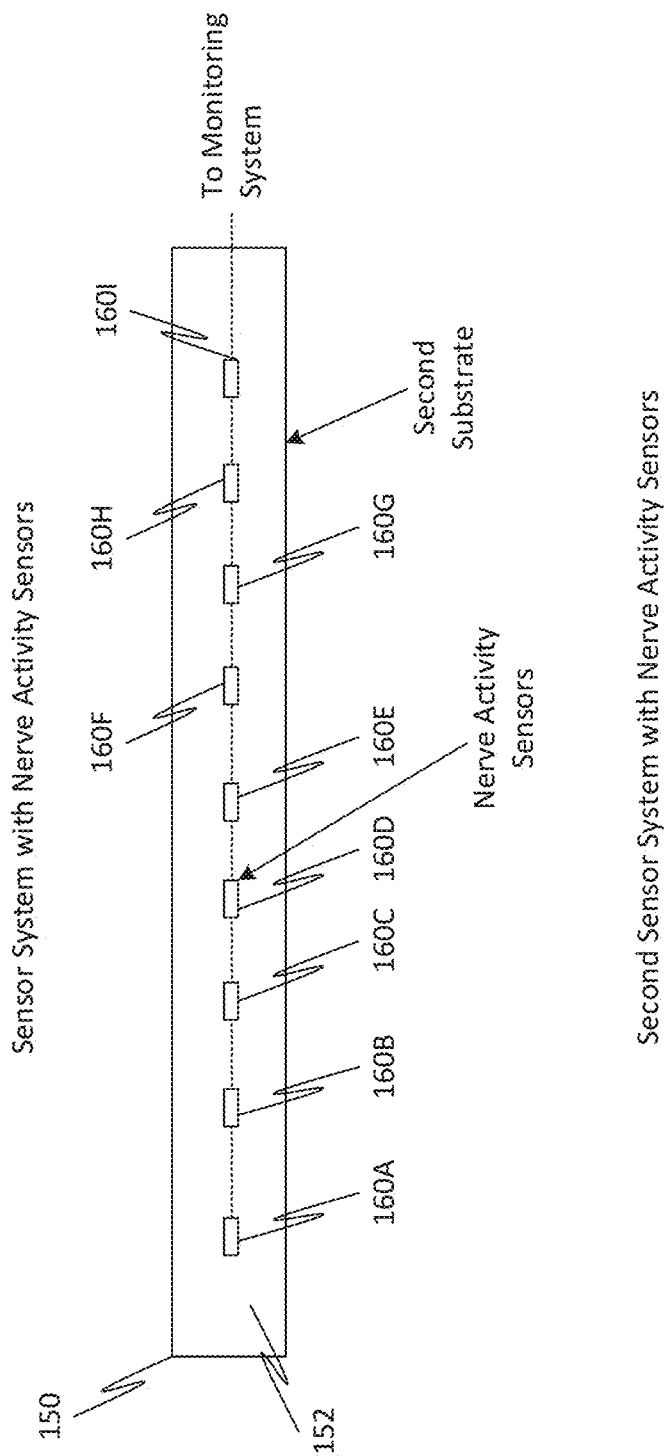
FIG. 5B provides a view of a sensor layer of a tMS sensing device, where the sensor layers includes a linear array of sensors.

Accordingly, as can be seen with reference to FIG. 5B, in various instances, a transcutaneous sensing and monitoring device 150 is provided. Particularly, the transcutaneous sensing device 150 may be configured for determining a reaction of a nerve to receipt of a magnetic stimulation applied to a target area. In particular instances, the transcutaneous sensing device 150 includes a housing 151. The housing may have a plurality of sets of opposed surfaces that may be offset from one another by a boundary member. In such an instance, one of the surfaces of a pair of opposed surfaces may be configured to form a top surface 151A and a corresponding other of the opposed surfaces forms a bottom surface 151B. Together the plurality of sets of opposed surfaces and boundary member bound a cavity, such as where the cavity is configured for retaining one or more components of the sensing device.

For example, within the housing 151 the sensing device 150 may include one or more insulation 153 and/or one or more sensor layers 155, such as where the sensor layer 155 includes a number of sensing units 152 formed of one or more sensor elements 160. Specifically, a first and second extended insulation layer 153 may be included, such as where the first insulation layer 153A may be positioned proximate the top surface 151A of the housing, and the second insulation layer 153B may be positioned proximate the bottom surface 151B of the housing. Likewise, an extended substrate layer 155 may be provided such as where the substrate layer is positioned between the first and second insulation layer. The substrate 155 is configured for determining the reaction of the nerve to receipt of the magnetic stimulation.

More specifically, the substrate layer 155 includes a plurality of sensing elements 160, which may be positioned along one or more surfaces of the substrate 155 layers. Each sensing element 160 may be a magnetometer or other sensing element that is configured for detecting a reaction in one or more nerve fibers to magnetic stimulation being applied by the tMS applicator 105 to the target area so as to produce a response. The substrate 155 may be in a variety of configurations and may include a plurality of components. For example, the substrate may include a printed circuit board 170 that is coupled with the plurality of sensing elements 160. The printed circuit board 170 contains one or more processing units 172, one or more memories 178, and a communications module 174.

In particular embodiments, the processing unit 172 is configured for receiving and processing the response data so as to produce processed response data. Further a communications module 174 may be provided whereby the communications module is configured for transmitting the processed response data. An antenna 179 unit may also be provided for enhancing data collection and transmission. Additionally, a surface member, such as a bottom surface of the housing 151B, may include, or otherwise be associated with an attachment mechanism that is configured for coupling the transcutaneous sensing and monitoring device to a portion of a subject's body such as proximate the target area.

One or more additional components, e.g., electronic components, may also be included, such as a temperature sensing element, a lighting element, an optical and/or/or sound generating element, an imaging element, and the like. For instance, a temperature sensor may be included. Particularly, a temperature sensor, such as one or more thermometers may be included, such as to determine and track temperature increases and/or drops before, during, and after treatment application, such as where the treatment area moves from being cold to being warm, such as mimicking the temperature of a healthy body part not in need of treatment, such as where the change in temperature to the injured body site can be due to an increase in circulation and perfusion. In various embodiments, the temperature sensor can be any type of sensor that detects temperature, such as a thermistor, PTC, NTC, etc. In particular instances, the temperature sensor can use light, such as IR light, emitted from one or more subdermal structures within the skin, for one or more of a variety of purposes, such as to calculate skin or core temperature of the wearer, to illuminate subdermal cell structures, and/or for capturing images thereof, such as to determine a change in subdermal structure temperature preceding, during, and/or after the application of magnetic stimulation and/or nerve conduction.

A lighting unit 125 including one or more light emitters and/or light sensors may also be included, such as where the lighting element includes one or more light sources. Any suitable light source may be provided, such as one or more diode units, e.g., a light emitting diode (LED), may be included and positioned within or about the housing of the device, such as for illuminating a tissue, for instance, the skin and/or a structure within the skin. For example, in one or more embodiments, the lighting unit may include a red, green, and/or blue light emitting diode, an infra-red or near infra-red light emitting diode, and/or a light sensor. In various embodiments, a combined temperature, LED sensor, and/or a near-infrared (NIR) spectrometer may be employed.

Additionally, in various instances, an imaging module 130, such as including an optical and/or image capturing element may be included. For instance, in particular embodiments, any suitable imaging element may be employed. The imaging element may be an optical imaging or a sonic imaging or other imaging element capable of distinguishing between structures in the tissues of the target areas, but in particular instances, the imaging device may include a CMOS or CCD camera. Further, as described above, the imaging module may include a light and/or sound emitter and/or a lens and/or an antenna for focusing the emitted energy and directing it into the tissues of interest, a transmitting element, e.g., a transceiver, may also be included. Likewise, the imaging module may include a receiver for receiving reflected and/or refracted light and/or sound energy back from the tissues so as to thereby generate an image of the tissues, such as on a structural and/or cellular level.

In a particular embodiment, the image capturing element 130 may include one or more micro cameras, which may further include a laser output, such as for tracking. Particularly, the image capturing and/or laser elements may be included within or be mounted to one or more of the sensor device and/or the tMS applicator, which cameras can be employed to take stereoscopic images of the treatment area and/or the internal structures of the treatment area tissue, so as to derive 3-D images of the target area and/or target nerves of interest. For instances, the imaging element may allow for 2-D or 3-D scanning of the target area, both with respect to the surface and sub-surface structures within the skin.

Consequently, the sensing and monitoring device 150 (and/or the tMS applicator 105) may include an optical module 130 that includes an illuminating and imaging element, e.g., one or more depth cameras, a depth and/or tracking unit, and a vision processing component that is configured for processing the viewed and/or captured images, such as of sub-dermal structures and vessels. More particularly, in one particular embodiment, the optical module may include dedicated vision and image processors, a depth module, and two or more, e.g., stereoscopic, depth cameras, and may be coupled to one or both of the tMS applicator, such as for determining a field of view such as for orientating the positioning element and/or the tMS applicator with respect to the target area, and/or may be coupled to the tMS sensor, such as for visualizing the tissues and structures therein within the target area. In various instances, the camera can be configured for taking infra-red, red, orange, yellow, green, blue, indigo, violet, near ultra-violet, and UV images, e.g., alone or in combination with one another, of the target area, so as to generate one or more images of the nerves, vessels, and other sub-tissue structures of the tissues of the target area, including the nerve fiber of interest. An appropriate wavelength of light may be selected so as to assure the appropriate depth of penetration for illuminating the desired sub-surface structure, such as via green light emission.

In various embodiments, a lighting module 135 may be included, such as where a light element may be employed in conjunction with one or more data collectors, such as a photodiode collector and/or an imaging element, such as for working in conjunction with the lighting element, so as to collect data and/or one or more images of the illuminated structures. Any suitable lighting element may be employed, but in some instances, the lighting element may include one or more diode units, such as a light emitting diode (LED). The lighting element may be positioned about the housing of the tMS sensing device 150, e.g., proximate the skin, such as for illuminating and/or indicating one or more usage parameters and/or conditions. For instance, in various instances, the lighting module may include both a light emitter, e.g., a yellow or green light emitter, and a light sensor. The lighting element may be configured for emitting an infra-red, near infra-red, red, orange, yellow, green, blue, indigo, or violet light, for instance, a near or infrared light, such as for illuminating structures within the tissues of the target area.

In various instances, the data and/or images collected may be used, e.g., by a processing element of the sensor device and/or system controller, so as to determine one or more system parameters, such as a depth, direction, and/or orientation of the tMS applicator in relation to the treatment site, as well as one or more wave characteristics of the magnetic field to be applied, such as a magnitude, a frequency, a wavelength, an amplitude, or other wave characteristics of the applied magnetic field and/or one or more pulses thereof. More particularly, an optical or lighting 125 and/or sound generating element, data collector, and/or image capturing element 130 can be provided, such as within the tMS applicator 105 and/or as part of the tMS sensor 150, wherein these elements are configured for working in concert together to define one or more nerves to be treated in the target area. In various embodiments, a laser 135 may also be provided, such as for tracking movements of the body in relation to the applicator device 105.

In particular instances, the light 125 and/or sound generating module may include a light emitting and/or sound generating element, image capturing device 130, e.g., stereoscopic camera, and/or a laser 135, which may be positioned such as for tracking movements of and/or within the body in relation to the sensing 150 and/or applicator devices 105, so as to ensure proper administration of the magnetic flux to the subject despite any movements of the subject, which will facilitate proper reading of the signal, approximate the treatment site, such that the target nerve cell can be identified, targeted, and treatments administered to the selected nerve, at the determined location and in the appropriate configuration.

In a manner such as this, the proper targeting, orientating, and/or administrating of the magnetic flux to the subject can be assured despite any movements of the subject. This may be accomplished by the system facilitating proper reading of the signal, identifying the target nerve, aligning the applicator 105 approximate to the treatment site 1000 in the target area, such that the target nerve cell can be identified, targeted, and treatments administered to the selected nerve, at the determined location and in the appropriate configuration. Likewise, various of the structural elements within the target area may also be identified, mapped, and/or monitored, such as through the optical or sound generating system.

Figure 6:
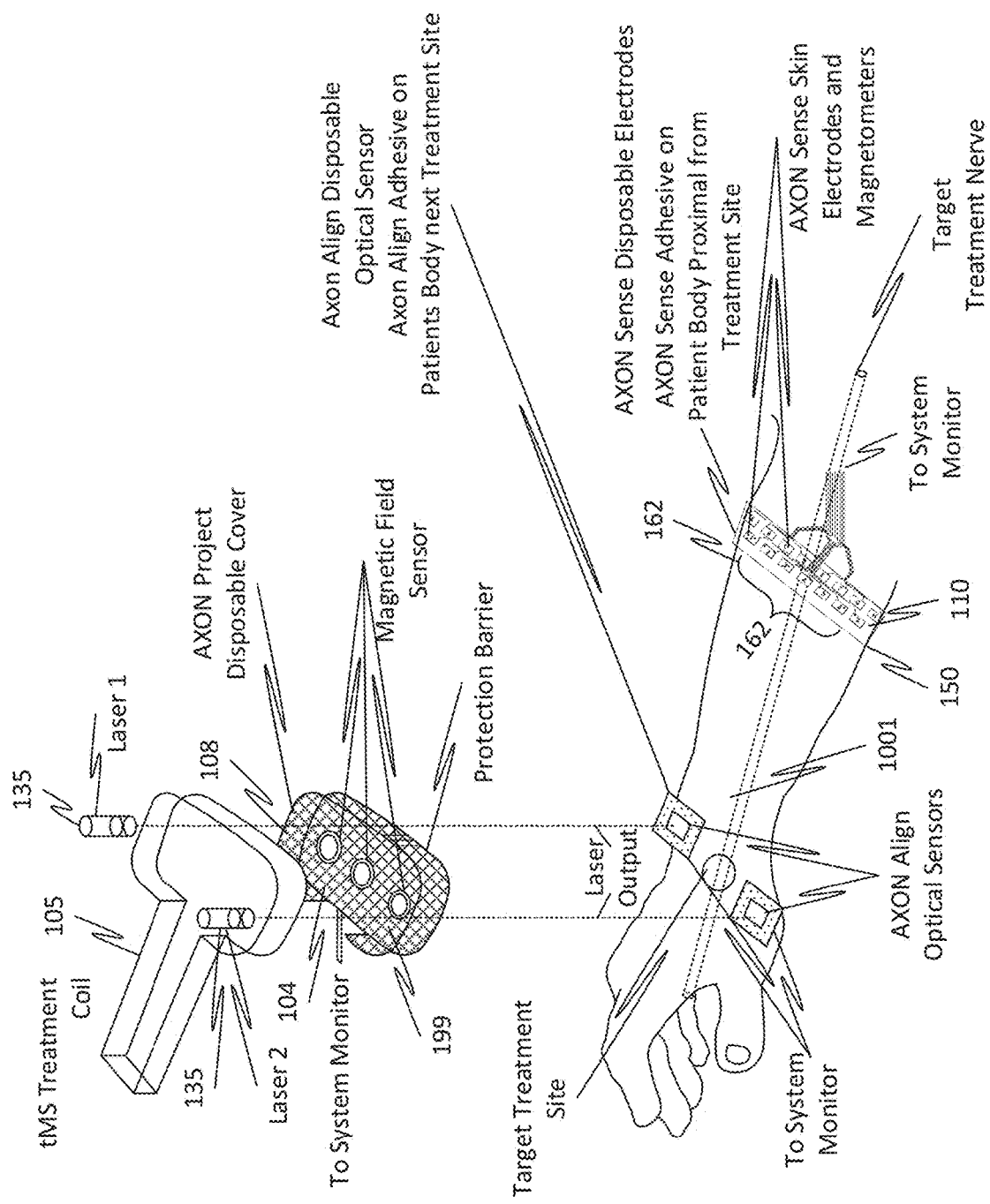
FIG. 6 provides an alignment procedure for the delivery of tMS to a target site of a treatment area on a subject in need of treatment.

Accordingly, in one aspect, as can be seen with respect to FIG. 6, the system 1 may be employed in a method for determining a location of a target nerve and/or a treatment protocol for delivering a focused magnetic stimulation to the targeted nerve may be provided, such as where the nerve resides in a target area in a body 1000 of a subject experiencing neuropathic pain, in this instance, the wrist of the body 1000. The system 1 may include a tMS application device 105, an activating protective cover 108, which must be removed so as to allow the activation authorization of the application device 105, and a tMS sensing and/or monitoring device 150.

The method may include one or more of the following steps. First, a transcutaneous sensing and monitoring device 150, as described above, may be coupled to the body 1000, such as at an area of pain experience. The transcutaneous sensing and monitoring device 150 may be configured for identifying a reaction of a nerve 1001 in response to an applied magnetic stimulus so as to produce an identified target nerve 1001.

In some embodiments, the sensing device 150 may include, or otherwise be associated with, a processing element 110A that is configured for accessing sensor element 160 data and determining, based on an evaluation of the sensor data, a proposed orientation for the tMS application device 105 to be in, relative to the target nerve 1001, so as to optimally focus the magnetic stimulation to the target nerve 1001 in order to more effectively provoke a therapeutic or prophylactic response in the nerve 1001. In various embodiments, the proposed orientation may characterized by one or more parameters, such as coordinates in an X, Y, and/or Z direction, and/or with respect to latitude and longitude relative to a given marker.

Once the target nerve 1001 has been defined within interstitial space and/or a proposed orientation of the tMS applicator 150 within ambient space has been determined, the transcutaneous magnetic stimulation (tMS) application device 150 may be positioned proximate the target area 1000, such as via handheld manipulation of the applicator 105 or via activation of a robotic or mechanical positioning system 140 (not shown). Specifically, the positioning system 140 may include a positioning element that may have articulating arm members, and in such an instance, the method may include articulating one or more of the arm members so that a transcutaneous magnetic stimulation application device 105 coupled to one or more of the arm members is positioned proximate the target area. In either instance, during the positioning process, the method may further include orienting the tMS application device 105 relative to the target area in accordance with the one or more parameters of the proposed orientation for magnetic stimulation delivery.

Once appropriately positioned and orientated, the tMS application device 105 may be activated so as to generate and deliver a focused magnetic stimulus to the identified target nerve 1001, such as when the tMS application device 105 is positioned proximate the target area 1000 and in the determined orientation. Subsequent to the coupling of the tMS sensing device 105 to the target area of the body 1000 and administration of the magnetic stimulus, the method may further include detecting, by the transcutaneous sensing and monitoring device 105, an activation of the identified target nerve in response to the delivery of the magnetic stimulus to the target area. A computing device 110A associated with the tMS sensing device 150, or a computing device 110 coupled through a network interface, having one or more processing engines or elements, may then be employed to characterize the activation of the identified target nerve 1001 so as to produce characterization results data. In various embodiments the computing device 110 may be an onboard computing element 110A or may be a stand alone computing device 110 otherwise coupled to one or both of the tMS sensing and monitoring device 150 and the tMS application device 105. Additionally, the method may include determining, e.g., by the computing device 110 or 110A, based on the characterization results data, a treatment protocol for the delivery of the focused magnetic stimulation to the identified target nerve.

In this manner the system 150 and its component parts may be configured for monitoring one or more tissues of the body 1000, as well as for monitoring one or more structures therein such as a nerve 1001 or a vessel to be or having been treated. For instance, in various embodiments, the tMS sensing and monitoring device 150 may be adapted for use as a wearable medical and/or health monitoring device, such as where the sensing device 150 includes one or more biological sensors, such as where the biological sensors are configured for sensing and/or monitoring one or more biological signs related to one or more biological conditions of the subject to be treated. For example, in one implementation, a sensor element 160 in addition to a near-infrared (NIR) spectrometer 125 may be configured for collecting data from which the processing element 110A of the device 150 may make one or more measurements regarding: light absorption, pulse oximetry, $O_2$ and/or $CO_2$ content, blood flow and/or pressure, heart rate, and the like.

And from the results of this processing, the sensor and monitoring device 150 may derive one or more conditions of the body of the subject, such as with respect to body temperature, blood pressure, blood glucose and/or alcohol levels, and/or the condition of one or more vessels, or other structures, in the tissues of the target area. Likewise, the sensor and monitoring device 150 may include a Galvanic skin response sensor, such as for measuring sweat (e.g., nervousness), such as at the target area, and/or the sensor device 105 may include an electrocardiogram (ECG or EKG) sensor, and so forth. Additionally, the one or more biological sensors may include a heart rate sensor and/or other sensors for determining blood pressure such as configured for determining a heart rate and/or blood pressure of the wearer.

One or more other non-biological sensors may be included, such as where the sensor unit 150 (or tMS applicator device 105 itself) may include one or more other non-biological sensors such as: an accelerometer, a pedometer, an inertial measurement sensor, an orientation sensor, and/or a gyroscope, a vibration sensor, a magnetometer, atomic magnetometer, skin electrode, and the like or a digital compass, or other suitable sensor. Where a magnetometer is included, e.g., in the sensing device 150, it may be configured for measuring the strength and/or direction of an applied magnetic field. In this regard, the magnetometer can be used to determine one or more characteristics, such as direction and/or orientation and/or magnitude, or intensity, of an applied magnetic field.

Where an accelerometer and/or gyroscope is provided, the accelerometer can detect movements in multiple, e.g., 3-dimensions or axes. The accelerometer and/or gyroscope can measure force of acceleration of the body part to which the tMS sensor 150 is attached, and can measure the movements and direction thereof, can detect acceleration of the user while wearing the device, and/or can track an activity level of the wearer. Particularly, in some embodiments, the tMS sensor device 150 can utilize the accelerometer to measure the activity level such as in conjunction with a measured heart rate and/or blood flow and/or blood pressure to determine the level of activity of the wearer.

One or more other elements may also be provided, such as electrodes, diodes, odometers, and the like may be included. For instance, one or more electrodes may be included, such as by being coupled to the housing of, or otherwise associated with, the sensing and monitoring device 150. In such instances, the electrodes may be employed such as in conjunction with a magnetometer of the device, such as for performing one or more conduction studies, such as for performing an EEG or EKG process, so as to determine the conductance characteristics and/or patterns of a tissue, e.g., nerve tissue, of interest. For example, one or more electrodes, e.g., two, can be placed proximate the identified tissue of interest, a stimulatory event can be induced, such as by the application of a magnetic or electric pulse, and the conductance through the tissue, e.g., nerve fiber, may be measured. Accordingly, in various instances, the sensor elements may include magnetometers, atomic magnetometers, skin electrodes, e.g., EEG or EKG skin electrodes, combinations thereof, and the like. In particular embodiments, the sensing elements may be configured as an array of sensors.

In view of the above, in one aspect, the disclosure is directed to a system for identifying a target nerve and/or for administering magnetic stimulation to that target nerve, once identified, for the purpose of treating neuropathic pain in a subject's body via the administration of catered magnetic stimulation. For instance, the system may include one or more of a transcutaneous sensing and monitoring device 150, such as for identifying and/or mapping out a position of a nerve to be targeted, as well as a transcutaneous magnetic stimulation (tMS) application device system 100 for delivering focused magnetic stimulation to the identified target nerve, as described above. In particular instances the tMS application device system 100 is a tMS applicator 105 that is part of a tMS application system 1. For instance, along with the tMS applicator 105, the tMS application system 1 may include one or more control modules 110, having a memory, a processing element, and a communications module having one or more communications elements. Further, the tMS application system 1 may include a positioning element 140.

Accordingly, in one aspect provided herein is a tMS application system 1 for treating neuropathic pain in a subject's body via the administration of magnetic stimulation that includes, along with a tMS sensing and monitoring device 150 and tMS applicator device 105, a control module 110 and a positioning element 140. Specifically, the tMS system 1 includes a transcutaneous sensing and monitoring device 150 for identifying a nerve to be treated with magnetic stimulation, and a transcutaneous magnetic stimulation (tMS) application system 1 for delivering focused magnetic stimulation to the identified nerve to be treated with magnetic stimulation. A control module 110 and a positioning element 140, such as an automated positioning element may also be included.

For example, the control module 110 may include a communications module for receiving the processed response data from the sensor module 150 as well as the data therefrom that identifies and characterizes the identified nerve. A memory may also be included, such as a memory that is coupled to one or more of a processing element and the communications module, such as for storing the processed response data, the characterization of the nerve data, and one or more treatment protocols. The memory may be any form of onboard or detached memory.

The control unit 110 includes one or more processing elements that are coupled to one or more of the communications module and the memory. The processing elements are configured for accessing the response data and the data characterizing the identified nerve from the sensing elements, and determining a treatment protocol to be administered to the subject for the treatment of neuropathic pain experience. The treatment protocol defines the application parameters and the delivery characteristics.

For instance, the one or more application parameters may include the voltage and current levels for generating the magnetic pulse of the magnetic stimulation. Further, the application parameters may include various parameters that characterize the waveform of the magnetic pulse to be generated, such as with respect to its wavelength, frequency, and duration. Likewise, the feedback received from the sensing elements of the various sensing units may be used to determine the one or more delivery characteristics.

Specifically, based on the degree, amplitude, and direction, e.g., magnitude, of the response of the nerve to the magnetic stimulation, the orientation and/or boundaries of the nerve may be determined and mapped out. Other waveform characteristics may also be measured and determined, including sensory conduction velocity (CV) as well as increases or decreases to sensory onset latency, nerve conduction, action potential strength, ionic flux, and the like. For example, the processing elements may employ received sensor element data and perform a plurality of triangulation and/or trilateration functions so as to define a set of coordinates that define an area including at least a portion of the nerve to be targeted for treatment. More specifically, in addition, to the delivery characteristics, e.g., defining the location of the nerve to be treated, the one or more processing elements of the control unit 110 may process the various sensed data from the response of the nerve to the applied magnetic pulse, e.g., its amplitude and magnitude, may perform one or more triangulation operations on the data, and may not only identify a nerve to be targeted but may map out the coordinates, e.g., with respect to latitude and longitude, and determine one or more proposed orientation parameters that may define or otherwise be used for orienting the tMS application device 105 relative to the target area 1000. Other locating operations may be included within the context of triangulation, including trilateration.

Once one or more orientation parameters have been defined, a positioning element 140 may be employed so as to position the tMS applicator 105 proximate the target area 1000, and to orientate the applicator 105 to the target nerve, such as in accordance with the determined orientation parameters. Accordingly the tMS application system 1 may include a positioning element 140. The positioning element 140 may have a proximal portion including a proximal end, and a distal portion including a distal end. In particular configurations, the distal portion may be coupled to the transcutaneous magnetic stimulation (tMS) application device 105, such as proximate the distal end, while the distal end may be coupled to a control module 110 and/or to a support or grounding member.

The positioning element 140 is composed of a plurality of articulating arm members that are configured for being moved and configured as necessary so as to position the tMS applicator in the determined orientation so as to achieve optimal activation of the target nerve. Further, in various embodiments, an automating element, such as one or more motors may be employed. Specifically, a plurality of the arm members may be coupled together by an automating element, which may be employed for automating the process of positioning and orienting the tMS application device 105 proximate the treatment area in accordance with the determined orientation parameters of the treatment protocol.

Accordingly, once alignment has been determined, the result will be a set of data defining the coordinates, such as along a length, of an A-β nerve. The coordinates define the depth and orientation of the target nerve, such as with respect to defining X, Y, and Z coordinates, which coordinates may then be employed by the tMS applicator 105 so as to deliver therapeutic magnetic pulses that are directed to the target A-β nerve, so as to depolarize and thereby activate the nerve fiber, which once activated deactivates the pain causing A-α, A-δ, and C-fibers.

Hence, once mapping has been performed, the sensing device 150 may or may not be removed from its position and/or the body altogether. For instance, in various embodiments, the sensing and the tMS applicator device 150 may be positioned directly on the body of a subject, and the tMS applicator 105 may be positioned adjacent and/or proximate to the tMS sensing device 150. The tMS applicator 105 can then be used to give a stimulatory pulse to a nerve to be targeted, the response to which can be detected by the sensing device 150 in a manner whereby the nerve to be targeted can be identified and its coordinates defined. In such an instance, the tMS sensing device 150, because it is positioned proximate the tMS applicator 105, it need not be removed from the body prior to application of a magnetic pulse. Thus, the sensing device 150 may be, but often does not need to be, repositioned and/or removed prior to application of the magnetic pulse from the tMS applicator.

Accordingly, in various embodiments, application by the tMS applicator 105 of a magnetic pulse may be coupled subsequently by the sensing of a response by the tMS sensing device 150 of a target A-β fiber so as to ensure that the target nerve has been appropriately activated, such as for mapping the target nerve and/or administering pain remediation. Specifically, the sensing and application devices 150 may be positioned and employed so as to map out the coordinates of a nerve fiber to be targeted, such as for pain remediation. Such coordinates can include the length, width, and depth of the target nerve. For instance, X, Y, and Z coordinates can be defined by one or more arrangements of the sensor elements 160 of the tMS sensor module 150, such as where the module includes one, two, three, or more sets of three sensor units 162 each having a plurality, e.g., 3, elements for triangulating the positioning and/or morphology of the target A-β nerve cell, e.g., by each sensor of the set recording the strength, intensity, and duration of the identifiable, characteristic waveform.

More Specifically, once the sensing device 150 is placed on or proximate the body, sensing may begin, but will likely be indistinguishable from noise of surrounding nerve fibers, including A-α, A-δ, C fibers, as well as A-β fibers and the like. However, once a magnetic pulse has been delivered to an A-β nerve cell to be targeted, a characteristic waveform, as can be seen with respect to FIG. 3D will be sensed and registered by the sensing device 150, and hence forward, the system can remove the resonant noise, and focus on defining the dimensionality of the target nerve fiber.

In various embodiments, the tMS sensing and monitoring device 150 may be positioned on the body 1000 at the site of immediate pain experience, or may be positioned proximate the spinal column, such as where the damaged nerve enters the spine. For instance, the neural system includes a brain, a spinal chord, and a wide variety of peripheral nerves. Peripheral nerves extend throughout the body and its limbs, but all join the spinal column via the Dorsal Root Ganglia (DRG). Accordingly, in various embodiments, a sensing device may be positioned proximate the DRG, and further, a tMS application device 105 may be positioned near, e.g., but not over, the sensing device 150, and may then be employed to administer therapeutic magnetic pulses to the nerve proximate where it joins the DRG.

Figure 5C:
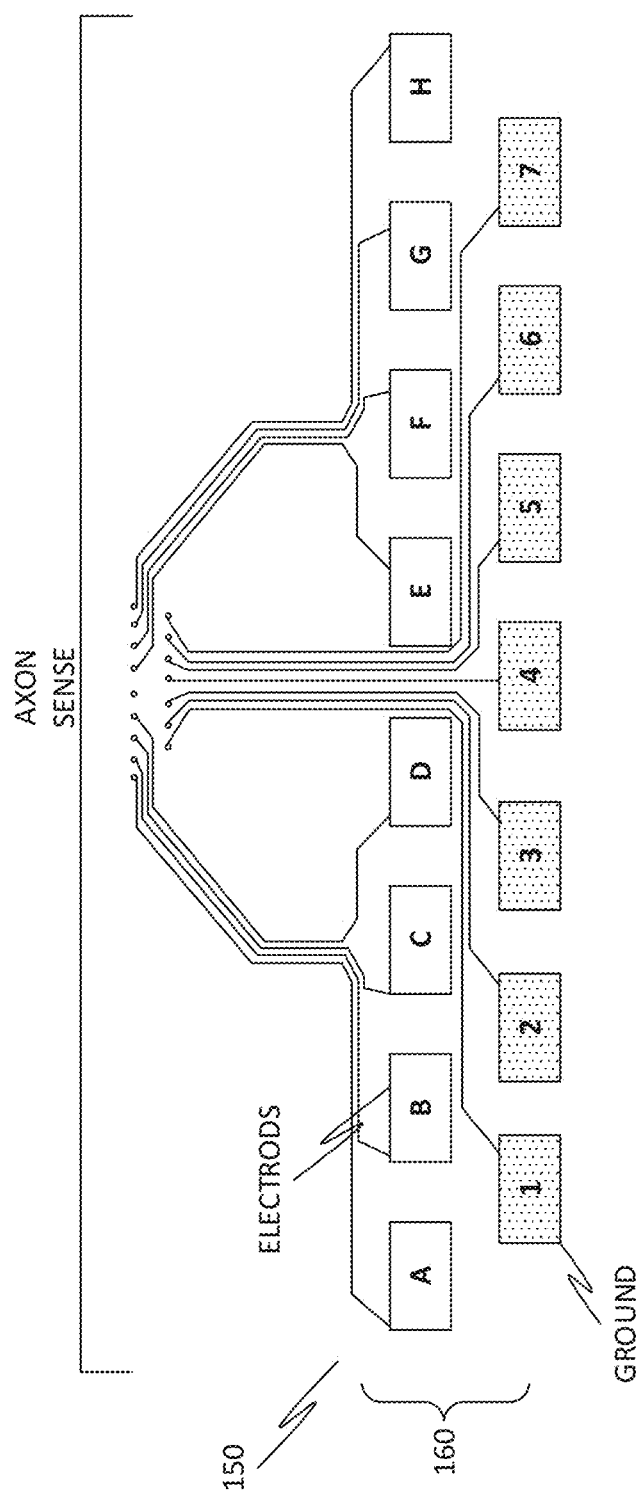
FIG. 5C provides a plurality of sensor layers of a tMS sensing device, where the sensors of each layer are electrically coupled together so as to form a sensor module.

In such an instance, as can be seen with respect to FIG. 5C the tMS sensing device 105 includes 15 sensing elements, which may include one or more electrodes and/or magnetometers 160. As depicted the sensor elements 160 are aligned in three rows of five sensors. In this embodiment, there are several different arrangements of sets of three sensor configurations, e.g., sensor units, whereby a combination of configurations of sensor elements 160 can be used to define the nerve fiber to be targeted.

A targeting operation may be employed whereby a tMS sensing device 150 is positioned proximate an identified nerve fiber, such us on or above a body portion 1000 in the tissues of which the nerve fiber resides. In one exemplary embodiment, the tMS sensing device may be positioned proximal a nerve fiber that joins the spinal column, and the tMS sensing device 150 is positioned proximal the Dorsal Root Ganglia, and the tMS applicator 105 may be positioned proximate thereto but away from the sensing device 150. Hence, once the tMS applicator 105 and tMS sensing device 150 are positioned, the tMS applicator device 105 may propagate a magnetic pulse, and the response of the nerve to the magnetic pulse, can be detected and measured by the tMS sensing device 150, such as by a set of three, or more, sensor elements in one or more, e.g., a plurality, of arrangements.

Consequently, once a magnetic pulse is issued, an A-β nerve to be targeted will respond by depolarizing with the characteristic waveform set forth in FIG. 3D. The wave pulse will then be detected by a variety of sensor units 152 including trios of sensor elements 160, and in response thereto, the morphology of the A-β nerve fiber can be mapped out by sensing it's depolarizations by the various sensor elements, such as in an iterative and/or sequential triangulation process. Thus, in view of the above, the tMS applicator device 105 can emit a first magnetic pulse, which will cause the A-β nerve fiber to depolarize. The depolarization can then be detected, e.g., by one or more sets of three sensor elements 160, and a first, second, etc., set of coordinates can be defined for the nerve fiber. Once the A-β nerve fiber has been detected and/or determined, the tMS applicator can be iterated over the surface area to better define the locality of the nerve. Additionally, one or more extrapolation operations can be conducted by a computing device, e.g., AI module, of the system so as to identify other various nerve fibers (or other structures), such as A-α, A-δ, and C fibers, which may have similar sensory nerve variable characteristics, which once identified can be targeted themselves and/or their responses can be characterized and be removed from the sensing operations as noise. Specifically, one or more extrapolation operations can be conducted by a computing device of the system so as to identify and remove other various nerve fiber responses, such as A-α, A-δ, and C fibers, which may have similar sensory nerve variable characteristics, which once identified their responses can be characterized and be removed from the sensing operations as noise.

Such probing by the tMS applicator device 105 may be an iterative process, such as where the tMS applicator is moved, such as cm by cm, mm by mm, micrometer by micrometer, even nanometer by nanometer, across a treatment area so as to better identify and characterize a target nerve fiber. Probing may also be performed so as to identify various different system settings, which probing may include administering a pulse at a variety of different configurations, such as, for example, 400 pulses at 0.5 Hz, or 800 pulses at 1 Hz, up to 4,000 pulses at 5 Hz, and the like. The number of pulses and frequency delivered can be manipulated in a manner to optimize the amount and length of depolarization in the target nerve without leading to depolarization and/or nerve fatigue, e.g., based on how quickly and/or intensely the nerve responds. Specifically, it is desirable to flood the nerve with activation signal in a manner that provokes and/or maximizes filtering at the DRG thereby deactivating A-α, A-δ, and C fiber signaling, and thus, reducing the experience of pain.

This mapping process can be repeated a number of times, whereby the combination of sensing elements for detecting the depolarization can be re-arranged, in an iterative fashion, to better isolate and define the configuration of the A-β nerve to be targeted. In a manner such as this, the configuration of the nerve fiber can be triangulated and mapped. In various instances, one or more times during this process the tMS application device 150 may be repositioned and/or re-orientated, so as to better perform the triangulation process. Further, during this process, activation of the A-β nerve will naturally result in the cessation of conductance in both A-δ and C fibers, as A-β is naturally a pain modulator the activation of which results in the deactivation of A-δ and C fibers. Consequently, once the tMS coil 115 emits its pulse, A-β will be activated, and correspondingly, activated A-α, A-δ, and C fibers will be deactivated, and pain that has been experienced, will cease. In this manner, noise from A-α, A-δ, and C fiber will be reduced, and removed.

Once the nerve has been defined, e.g., via the sensing of its actionary response to the magnetic pulse, then the tMS device will scroll through movements and/or moments so as to maximize the signal, better define the target nerve, and better administer therapeutic magnetic pulses thereto. Further, once the target nerve to be treated has been identified, defined, and its coordinates defined, the positioning and orientation of the tMS application device with respect thereto can also be defined, and used to administer treatments over subsequent treatment administrations.

Additionally, once the target nerve has been defined, the health of the nerve can then be determined, such as by its conductance pattern, such as with respect to whether it has suffered trauma or other form of dysopothy, diabetic neuropathy, chemotherapy neuropothy, and the like. Particularly, it can be determined if the subject suffers from diabetes or chemotherapy neuropothy, such as based on the characteristics of signal conductance, e.g., strength or weakness of the conductance, whether it is patchy or consistent, strong or weak, tight or lose, or the like. Thus, the system may be configured for performing one or more neuropathic diagnosis. It is to be noted that although these measurements are disclosed with regard to use of magnetometers and/or electrodes, the imaging module can also be used for partaking in these measurements.

Accordingly, in various instances, the system 1, e.g., a tMS applicator 105 and/or tMS sensing device 150, may be configured for delivering both a magnetic and an electrical field or pulse to one or more nerve cells of the subject in a manner so that the two fields pulse in sequence, as depicted in FIG. 3D, in one embodiment, or not in sequence, in another embodiment. As can be seen with respect to FIG. 3, the tMS applicator 105 may include a plurality of wire wrought treatment coils, 115A and 115B, which may be configured as magnetic coils that are adapted for receiving a current passing there through, and in response thereto, generating a magnetic impulse. The magnetic impulse may have defined wave characteristics that may be modulated as set forth above. Specifically, the characteristics of the generated magnetic wave field will have a wavelength, a frequency, and amplitude that may each be adjusted.

More specifically, as can be seen with respect to the representation of FIG. 3E, given the figure-8 configuration of the tMS applicator coils, each magnetic coil 115 will generate a magnetic field, which individual magnetic field has an individual amplitude that reinforces that of the other. So being, the tMS applicator 105 may be designed such that the distance between the coils 115 causes a single magnetic waveform to be generated in such a manner that the amplitude of that waveform can be increased and/or decreased as needed to treat each individual subject in a uniquely catered manner. In various embodiments, other nerve reaction characteristics may also be affected, e.g., modulated by the system such as including sensory conduction velocity (CV) as well as increases or decreases to sensory onset latency, nerve conduction, action potential strength, ionic flux, and the like.

Figure 3F:
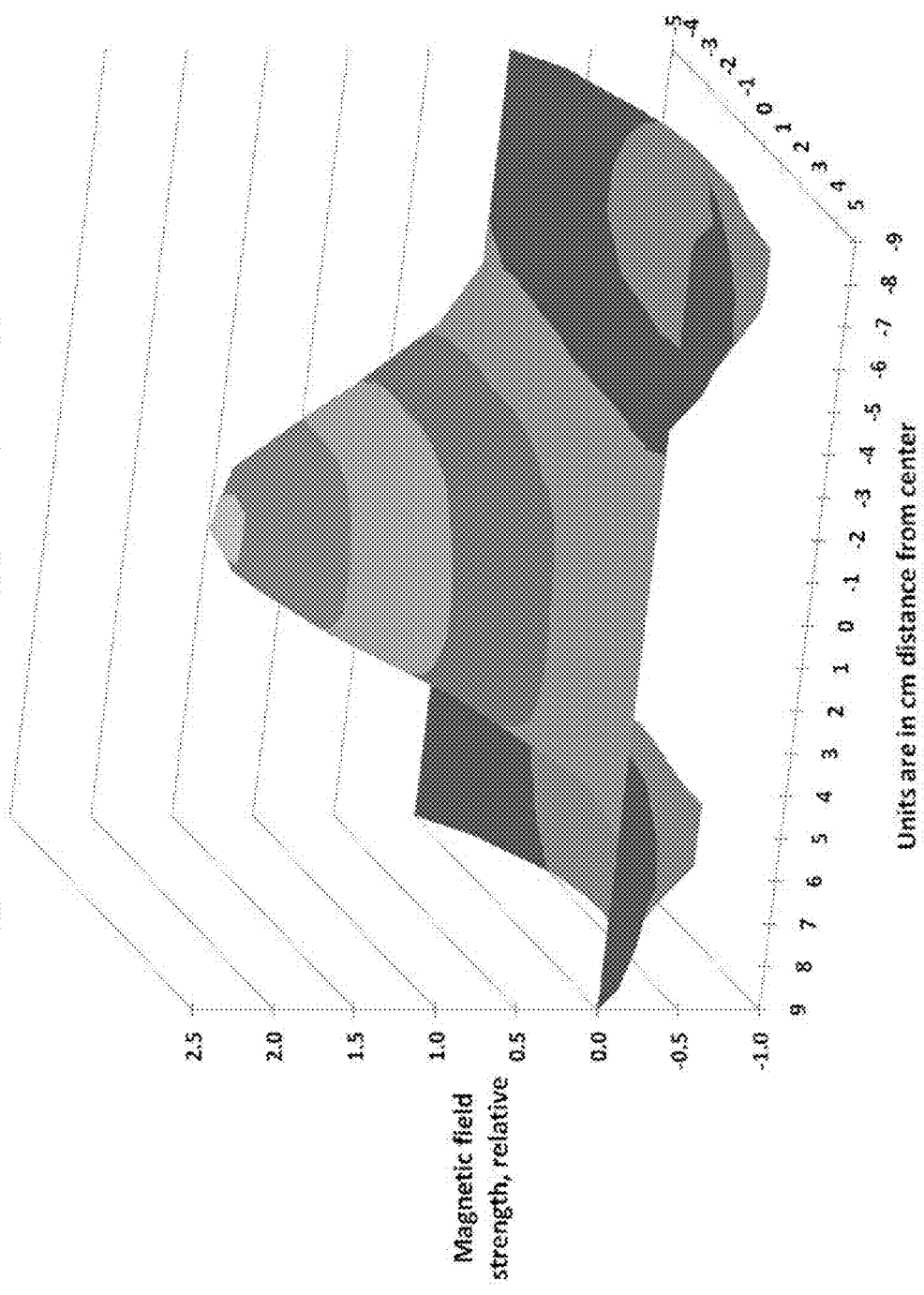
FIG. 3F provides a graphical representation of an amplitude of a the generated magnetic pulse of FIG. 3D.

For example, as can be seen with respect to FIG. 3F, the field shape of a generated magnetic pulse is presented at about 50% amplitude, which amplitude can be increased or decreased dependent upon the depth of the distance between the nerve to be treated and the magnetic coil. Particularly, the depth of penetration, and/or field strength, may be increased or decreased by moving the coils closer to the body of the subject to be treated, and may further be modulated by increasing the amplitude of the magnetic field.

More particularly, as depicted, the two lower portions represent the center of each coil, and the line between them represents a horizontal axis, and the peak of the cone forms a vertical axis that represents the combination of the magnetic fields, which is at a determined depth below each coil, in this instance, the vertical axis extends from −1 (the coil surface) to 2.5 cm, which is 50% penetration. Hence, at full penetration the depth may be about 5 cm, and in some instances, can be deeper, such as at about 10 or 20 cms. Accordingly, as can be seen with respect to FIGS. 3D, 3E and 3F, the resultant waveform emitted from the magnetic coils that the tMS applicator 105 generates may be a single waveform that has an amplitude that can be adjusted so as to effectuate deeper penetration. Particularly, the two generated magnetic fields can be brought into or out of sequence to determine the resultant effects on the nerve cells of the subject, e.g., by modeling their waveforms, e.g., with respect to wavelength, frequency, amplitude, and the like. Other waveform characteristics may also be modulated by the system including sensory conduction velocity (CV) as well as increases or decreases to sensory onset latency, nerve conduction, action potential strength, ionic flux, and the like.

Further, in various embodiments, a tMS sensor system 150 may also be provided. In certain embodiments, a tMS sensor system 150 may include one or more magnetometers 160 and/or electrodes, which may be included as part of, or otherwise be provided in conjunction with, the tMS application device 105. For instance, a tMS application device 105 may be provided so as to generate one or more magnetic pulses to a targeted portion, e.g., a nerve fiber, of the body of a subject, and further, one or more tMS sensing devices 150 may also be provided so as to detect the reaction of the nerve fiber in response to the provided magnetic stimulation. In particular embodiments, the tMS sensing device 150 may also be configured for delivering an electrical impulse to the skin of a body to which it is attached. Hence, in certain instance, the present systems may be configured for delivering, one or both of a magnetic and/or an electric field, such as simultaneously or sequentially, to the tissues of the treatment area.

The magnetometers and/or electrodes can be in any suitable arrangement. For instance, one or more of the magnetometers and/or electrodes may be formulated as a skin electrode, a magnetometer, or both, such as where the distance between the electrodes, and respective sensors, is precisely determined, based on the selected functions to be performed. Where electrodes are present, the tMS sensing device 150 may include an electric field generator, and may additionally include an interface layer, such as a hydrogel, e.g., a conductive hydrogel, so as to interface between the tissue surface and the electrodes. The hydrogel may be applied as an interface between the body of the subject receiving treatment and the tMS sensing 150 and/or application 105 device. For instance, a hydrogel may be placed between the electrodes and/or magnetometers associated with the device so as to better provide a conductive interchange of data between the body and the electrodes and/or magnetometers of the sensor.

In a manner such as this, respective nerve fibers can be identified and localized with respect to the other various nerve fibers in the surrounding tissues. Particularly, an electric field can be applied to one or more sub-tissue structures so as to determine where a stimulated conductive signal within a nerve is in fact occurring, thereby identifying the nerve and/or its structure. Likewise, a magnetic field can be used to determine conductance wave characteristics.

In view of the above, FIG. 5C presents an exemplary embodiment of a sensor unit module 162 within a tMS sensing device 150 of the disclosure, where the sensor unit modules 162 includes at least one substrate 155 upon which one or more sensors 160, in this instance, a plurality of sensors, are positioned. Specifically, the sensor units 162 may include a plurality of electrodes and/or magnetometers, which may be electronically coupled together by one or more traces or wired interconnects. Particularly, in this embodiment, the substrate 155 is formed of silicon and includes two rows of sensors 160 demarcated by letters, A-H, in a first row, and numbers 1-7, in a second row, where each individual sensor element 160 is connected to a central controller 110A via an interconnect. In this instance, two rows of eight magnetometers are presented but any number of rows and/or sensors per row may be employed for these functions.

In various instances, the silicon substrate 155 may be configured as a semiconductor, such as complementary metal-oxide-semiconductor. The sensors 160 can be any element configured for performing a sensing function, and as such may include, or otherwise be coupled to, an imaging module 130, an electrode and/or magnetometer element 160, and the like. A unique feature of the tMS monitoring and sensor device 150 is that because there are multiple sensor units and/or sensor elements within the module it makes nerve identification and localization a relatively straightforward process, such as via triangulation.

Accordingly, in various instances, the tMS applicator 105 and/or tMS sensor 150 devices may be used to identify and/or map a nerve fiber, and/or other sub-tissue structures, such as muscle fibers and vessels, such as by triangulation and trilateration, where any three sensors, e.g., of two or more rows of sensor arrays, may be employed to perform the triangulation and/or trilateration. A suitable sensor array unit 162 may have any suitable configuration and include a variety of different sensors 160, in a multiplicity of arrangements, but in some instances, a plurality, e.g., two or three, or four, sensor units 162 may be provided. For instance, an array of sensors 160, such as a linear, staggered, and/or a multi-layer array of sensors may be provided. In particular instances, the distance between individual sensor units is finely measured and at a determined spacing from one another.

Particularly, in one configuration, each sensor unit 162 may include three groups of sensors 160 forming a sensor module, which sensors 160 are positioned so as to allow for the triangulation of the positioning, orientation, and/or configuration of one or more sub-surface nerve fibers or tissues, such as where each grouping includes one, two, three, four, five, six, nine, twelve, sensors, and the like. For instance, in various embodiments, one, two, or more sets of three sensors 60 may form an array that may be used to triangulate and/or translaterate two or more positions of one or more fibers within the tissue of the target area. In one exemplary embodiment, one set of sensor arrays, e.g., 1, 2, and B, may be tasked with identifying the nerve fiber, and other sensor arrays, e.g., 2, 3, and C, and/or 3, 4, and D may be tasked with determining a location of the nerve fiber. Additionally, another sensor array, e.g., 6, 7, and G, may be employed so as to determine the morphology of the nerve fiber. In this manner, any set of three sensors can be employed so as to perform any number of the sensing functions disclosed herein, such as for performing a mapping operation.

A lighting element, an optics component, and/or an imaging module, including an image capturing device may also be included so as to capture an image of the interior structures of the tissues of the target area during one or more of these triangulation and/or trilateration operations so as to better identify and localize the nerve fiber of interest. For instance, in some embodiments, the sensor device may include a sound generating mechanism for generating the image.

As indicated, in particular embodiments, the imaging module may include an optical and/or sonic imaging element capable of imaging and/or identifying various of the different cellular structures in the tissues of the target area. For example, in various embodiments, the imaging module may include or otherwise be associated with one or more of a light and/or sound emitter and/or an optical element and/or an antenna for focusing the emitted energy and directing it into the tissues of interest. Likewise, the imaging module may include or otherwise be associated with a receiver for receiving the reflected and/or refracted energy back from the tissues so as to thereby generate an image of the tissues, such as on a cellular level, and a transmitter, for transmitting the images, such as to a control module of the system.

Accordingly, in various embodiments, the sensor module may be configured for generating a 3-Dimensional morphological positioning of the sub-tissue structures of the area being treated, such as via a computer generated map or a captured or otherwise recorded image of the nerves, muscles, vessels, and/or other structures within the tissue of the treatment area. In a manner such as this, and as described in greater detail herein below, a nerve fiber map may be generated, whereby the map provides a spatially resolvable interior architecture of the treatment site, specifically with respect to preferentially identifying particular nerve fibers, e.g., A-β, over the other interior structures present in the tissue being treated, such as A-α, A-δ, and C fibers, which in various instances, can be filtered out as noise, such as where only A-β nerves are being targeted for treatment. Of course, in certain other configurations, various other nerve fibers, such as A-α, A-δ, and C nerve fibers, or other interior tissue structures, such as blood vessels, muscle tissues, and the like may be targeted. Hence, in various instances, a signal, such as a magnetic, light, sound, electrical, or other signal may be emitted and focused into the tissue of the target area, and after a given time period a return signal may be collected.

Such imaging may be performed before, after, or during the administration of a stimulatory magnetic or electric, e.g., an electromagnetic, pulse is administered to one or more of the nerve fibers of interest, where by the nerve's response thereto can be used to identify and map the nerve with respect to the various other surrounding nerve fibers in the tissue of interest. More particularly, the nerve cells to be stimulated may be the nerve cells of interest, e.g., an A-β nerve fiber that is stimulated in a manner to produce activation, e.g., for identification purposes, or the nerve cells to be stimulated may be the surrounding nerve cells, e.g., an A-α, A-δ, or C fiber, from which activation the nerve fibers of interest may be identified and located, e.g., with respect to the activated surrounding nerve tissues, such as via extrapolation from identified nerve cells.

Any given tissue may be innervated by a plurality of different nerves being composed of a variety of different nerve fibers. Typically, nerve tissues are composed of a plurality of A-α, A-β, A-δ, and/or C fibers that are all packaged together, e.g., very closely, which makes identification, mapping, and targeted delivery of a focused magnetic pulse very challenging. However, the tMS sensing device 150 disclosed herein can be uniquely configured so as to identify, recognize, and distinguish between the various different nerve cells, muscles, vessels, and other subdermal structures of the tissues in the treatment area.

Accordingly, the present devices, systems, and the methods of using the same are directed to identifying, locating, mapping, isolating, and delivering a targeted magnetic field to a nerve tissue, e.g., one or more nerve cells of interest, as explained herein. The devices and methods for performing these procedures are explained in detail herein below. Particularly, in various embodiments, these functions may be performed by the tMS sensing 150 and tMS application 105 devices, as herein described. For instance, one or more of the tMS sensing 150 and applicator 105 devices may include an imaging module for illuminating the tissue of interest in the target area, visualizing interior structures therein, and capturing one or more images of the illuminated area and/or structures therein. In particular embodiments, the imaging module may include or otherwise be associated with one or more of a light emitter and light sensor, an optical unit, and an image capturing device, such as a camera, so as to take one or more pictures of images of the target area. In various instances, the imaging module may include a sound generating mechanism, such as for better generating images of the interior tissue structures.

The captured images may be used for a variety of different purposes, such as for identifying, locating, mapping, isolating, and delivering a targeted magnetic field to an identified nerve tissue. For example, in one particular embodiment, one or more of these images may be used to remove background noise from structures not of interest from the treatment area so as to isolate the identified structures, e.g., nerve fibers, of interest. Particularly, such exclusion, e.g., filtering, is useful for more accurately effectuating the targeted receipt of treatment, such as to at least partially resolve and/or model the spatial configuration of the structure, e.g., nerve fiber, to be treated.

Specifically, in various embodiments, the system components may be configured so as to resolve and/or generate an interior nerve fiber, e.g., A-β, morphology, with mm and sub-mm accuracy, for instance, from about 0.01 to 1 mm, so as to better determine where treatment and in what orientation it should be applied. One or more filters, such as for eliminating background noise may be provided, such as to isolate a specific nerve fiber for treatment, e.g., A-β, from those other nerve fibers, e.g., A-α, A-δ, and C fibers, and other structures, to which treatment is not going to be administered and/or which may interfere with the administration of treatment. Once the A-β fibers have been identified, the surrounding structures can then be excluded from the imaging and/or targeting area, such as via a suitably filtering operation implemented by one or more system processors, such as in an inverse problem solution.

Particularly, once the A-β fibers have been identified, the A-α, A-δ, and C fibers can be corrected for or otherwise filtered out. This filtering is useful because these A-α, A-δ, and C fibers provide noise for the accurate targeting and application of the magnetic field for treatment. The identification and filtering of these fibers may be performed visually, via image subtraction, coordinately, mathematically, based on conductance, and/or signal noise reduction, and the like. More particularly, both A fibers and C fibers have different conductance rates, and thus, their conductance have waveforms that are distinguishable from one another.

However, the presence of all of these divergent signals cause noise and make identifying the desired signaling difficult. But, once the conductance waveform for the fiber of interest is identified, the other waveforms, e.g., having different Hz, can be subtracted from the mapping and/or application field. For example, the conductance of A-β fibers have a unique and distinguishable waveform that can be identified and isolated, such as via the sensing and/or monitoring unit. Hence, the tMS device can be configured so as to activate and produce conductance in the desired fibers, e.g., A-β fibers, to the exclusion of other fibers.

Specifically, in various embodiments, the administered pulse can be catered specifically to generate an activation energy in the fiber of interest, such as at a determined unique frequency, such as between about 0.1 to about 10 Hz, about 1 to about 7 or about 5 Hz, including about 1.5 or 1.65 hz to about 3 or 4 Hz, including about 3.3 or about 3.5 Hz or more, and the like, including the numbers in between the cited ranges. The pulse can likewise be administered for an appropriate length of time to produce the desired activation, such as between about 0.001 seconds to about 10 seconds, 0.01 to about 5 or about 7 seconds, for instance, about 0.1 or 0.7 seconds to about 2 or about 3 or 3.5 or 4 seconds, including about 1 second, or more and the like, including the numbers in between the cited ranges.

These wave characteristics may vary, e.g., based on the nature of the fiber to be activated, and its natural activation energy and conductance waveform, e.g., based on its natural pattern. However, in certain instances, the waveform may be manipulated, such as by computer generation, so as to selectively identify and/or activate the fiber of interest, in a manner that wouldn't naturally occur in the nerve itself. Hence, the system may be configured for generating a unique signal in a target nerve that can then be used to activate and identify unique fibers, while excluding those surrounding fibers that are not of interest.

Accordingly, in a manner such as this, the system 1 may be configured for performing one or more localization operations. For instance, in one aspect, a method for identifying and locating a nerve, e.g., based on its activity, within a tissue defined by a treatment area, is provided. Particularly, the system 1 may be configured for identifying the location of one or nerve fibers within a target area of treatment, such as where the identifying occurs through application of one or more of a magnetic and electric field, such as via transcutaneous magnetic stimulation of the treatment area, which field may be applied to the target area in conjunction with a sensor array that is configured for determining and/or measuring the output and/or a response thereto.

More particularly, a tMS sensor device 150, as described herein with respect to FIG. 5C, having an array of nerve activity sensors, may be placed in a known location, or a plurality of tMS devices may be positioned at a plurality of locations on the body, which device(s) can be used to locate a target site within one or more target areas of a subject's body, so as to localize one or more particular nerve structures in need of treatment. These one or more sensor devices 150 may be configured for measuring and/or recording measurement data of a nerve in response to a magnetic and/or electric field applied from a tMS applicator 105 to the target area, e.g., directed at the target nerve of interest.

Once the structures, e.g., nerve fibers, of interest have been identified, e.g., through an identification protocol and/or imaging, computer generation, and the like, as explained herein, the relative coordinates of the structure can be defined, saved, and used for later targeting based on the identified, mapped, and/or saved coordinates. In various embodiments, feedback from a subject, e.g., patient, may be elicited so as to identify and/or confirm one or more of identification, targeting, and/or mapping, such as to confirm feedback received by the tMS sensing device.

Generally, an exemplary targeting and/or mapping procedure may include one or more of the following steps. For instance, as indicated, the tMS sensing device may include one or both of an imaging and a sensing module. In such an instance, the tMS device may effectuate the delivery of a magnetic field to a target area, and the tMS sensing device may sense the physiological response thereto, while an imaging module thereof may take one or more images of the physiological response. In this manner, one or more interior structures, e.g., nerve tissues, within the target area may be activated in response to the applied magnetic field, the response may be sensed by the tMS sensing device, and the tMS imaging module may capture an image of the activated structures, so as to identify the target nerve.

Likewise, once identified, the positioning of the nerve fiber, such as defined by its spatial coordinates, may be recorded, so as to allow for more precise, targeted treatment. Specifically, once the target nerves in the treatment area have been identified and/or mapped, a treatment can be applied, such as by being directed to the targeted nerve tissues so as to effectuate the diminution of the experience of pain. For example, as explained herein below, a target nerve may be identified and characterized such as by its response to the tMS applied stimulation, where no stimulation of the structure in response to the applied magnetic field indicates the structure is not the nerve of interest to be treated, and where there is a decrease in pain experience in response to the applied magnetic field may be an indicator that the reactive structure is, or is at least associated with, the nerve of interest.

More specifically, once a responsive structure has been identified, it can further be subjected to targeted stimulations so as to better characterize the structure. For instance, the orientation and spatial positioning of the tMS applicator may be changed, e.g., iteratively and repeatably, so as to map the area and its structures and/or to extract one or more features thereof. This feature extraction, therefore, can be performed iteratively in accordance with any pattern, such as by navigating a grid like pattern or a pattern of concentric circles, e.g., of decreasing or increasing diameters, such as described in greater detail herein below.

Particularly, where the circle is too big, too many structures will be contacted, and the treatment may be too diffuse. However, where the circle is too small, it may be too difficult to hit the right area in the first place, and targeting cannot accurately begin. Likewise, having a smaller focus area may not provide a wide enough range to activate the treatment area. As such, the area of focus can be increased and/or decreased, iteratively, as needed to find a target area, e.g., a target nerve fiber, so as to serve as an anchor point, which may then be used to define the extent of the target nerve, such as by moving the application of stimulation in a pattern designed to define the target nerve and its branching.

Consequently, having a plurality of sensor elements as part of the sensor device is useful, such as for triangulating the nerve cells. Accordingly, in a particular instance, the system may be configured for identifying and determining the target tissues of interest, such as by formulating an inverse problem solution. In a manner such as this, one or more of the various A-$\alpha$, A-$\beta$, A-$\delta$, and C fibers may be pinpointed within the tissues of the treatment area, such as by determining and/or characterizing their response to magnetic and/or eclectic stimulation. Once the pain causing nerve fiber(s) has been identified, the pain fiber of interest may be mapped such that the system, e.g., via the tMS applicator and/or tMS sensing device, is able to lock on to its conductance signal, and then the positioning element may be positioned in the appropriate three-dimensional space so as orientate the tMS applicator to effectuate targeted delivery of a magnetic field to the affected nerve fiber.

For example, in performing a mapping and/or targeting procedure, a sensing device having an array of sensors, such as set forth with respect to FIG. 5C, may be used so as to give feedback to the system controller in a manner so as to define the target area, identify the nerve to be treated, and once identified, map both its co-ordinates, such as for orientating the tMS applicator, and delineating the nerve's morphology, such as for more precise targeting of the nerve, e.g., A-$\beta$ nerve fiber, in need of treatment. Such a mapping and/or targeting procedure can begin by applying a general, non-focused pulse to the target area to determine if there is a reduction in the general experience of pain in the area, as determined by correlating feedback from the subject being treated, and feedback from the sensing array device. If a reduction of pain is not experienced or otherwise sensed, the tMS applicator can be moved to a new position and/or orientation, and another pulse can be delivered, such as until an appreciable decrease in pain experience is determined.

A mapping procedure can be performed in several different ways. For instance, a locating and mapping procedure may be configured to be performed in a grid-like fashion.

Particularly, the treatment area may first be defined, such as by a large square that is made up of a plurality of smaller squares, each representing a predefined area, such as of square boxes, and an area of one box of the grid is tested, to determine its reactivity to treatment, until the pain causing nerve has been appropriately identified and/or mapped, and the appropriate wave characteristics determined. In one instance, a grid-like structure may be applied to the treatment region whereby the treatment region can be broken down into sub-regions and through an iterative process of application of magnetic stimulation a narrowly defined active site can be identified.

Specifically, a grid of rows and columns forming boxes can be applied to the treatment region. In particular embodiments the grid can be formed from 3 to 6 to 9 to 12 to 16 boxes that together form a larger box that defines the boundaries of the target region. The boxes can vary in size, such as where each box may be from about 3×3 mm to about 9×9 mm to about 12×12 mm in area, depending on the target are and/or treatment site, e.g., whether it's smaller than a finger or larger than hand, etc. Regardless of size, stimulation can be delivered by the tMS device in an iterative, square by square fashion, to the various sub-regions of the target region until all areas proximate the treatment site have been suitably identified.

Accordingly, when a magnetic pulse is delivered to the appropriate pain signaling nerve fiber, in the correct orientation, so as to stimulate activity in the nerve cell, a concomitant dulling of the pain will be experienced by the subject, and the box defining that targeted site can then be identified as part of the treatment area. The coordinates of the device and characteristics of the impulse signal can be determined and recorded, such as in conjunction with the tMS sensing array device. This process can be repeated until an adequate number of areas have been identified so as to define the treatment area, and more particularly, the treatment site, such that by applying one or more magnetic pulses to the treatment site results in the diminution and/or total abeyance of pain sensation.

In various embodiments, the grid may be laid out like a telephone key pad with numbers from 1 to 9, stimulation is provided to each number, e.g., sequentially, and for each number the subject can self-report an evaluation on the pain diminishment, such as using a scale from 1 to 10, and in this manner each box particularly defining the precise bounds of the treatment site may be defined. Hence, by aligning the active boxes and correlating the application of the magnetic device with sensor data received by the sensing apparatus, the topographical distribution of the nerve may be defined such as by horizontally, vertically, or diagonally aligning the active boxes, e.g., where three sequential numbers demarcate a horizontal distribution pattern, any number separated by three demarcate a vertical distribution pattern, and a sequence of odd numbers demarcates a diagonal distribution pattern. Of course, other patterns can also be identified based on the characteristics of the nerve distribution. Accordingly, in a manner such as this, the nerve to be treated may be clearly identified, localized, mapped, and treated. Hence, one or more locations on the grid may be identified, based on sensed data and subject responsiveness to the targeting pulses, and then through a repetitive, iterative process the nerve fiber to be targeted can be mapped out.

Once mapped out the characteristics of the pulses can be calibrated to maximize delivery effectiveness. For instance, during this process the unique waveform of the conductance within the nerve fiber can be sensed, e.g., by the sensor array, or otherwise determined, and can then be used to identify and further map the target nerve fiber, such as by its unique pulse sequence, and the target nerve fiber can be distinguished from its neighboring nerve cells. As indicated, in certain instances, this targeting may initially be the result of an iterative process, e.g., of trial targeting, however, once its dimensionality has been defined and/or mapped, its targeting can be achieved much more efficiently and accurately. In a manner such as this, the target site can be defined and mapped, and effective orientation of the tMS applicator can be determined, so as to effectuate pain relieving administration of the magnetic pulse.

Accordingly, in view of the foregoing, in one aspect, provided herein is a system 100 for identifying one or more characteristics of a neuropathic nerve to be targeted with an application of a focused magnetic stimulation so as to ameliorate neuropathic pain experience. So being, provided herein is a transcutaneous sensing and monitoring device 150 that is configured for detecting a prospective nerve's response to the application of a magnetic stimulation as well as a computing device 110 that is configured for analyzing sensed response data for the purpose of identifying and characterizing the identified nerve. Particularly, as recited above, the transcutaneous sensing and monitoring device 150 may have a plurality of sensing elements 160, which may be configured in the form of a grid including both rows and columns of sensing elements, for instance, as depicted on FIG. 5C. Any number of sensing elements 160 may be provided such as in any number of rows and columns, depending on the size and orientation of nerve to be targeted, such as in 2, 4, 6, 8, 10, or more, or any number there between may be provided. Each sensing element 160 may be a magnetometer, or other sensing element, is configured for identifying a reaction of a nerve in response to an applied magnetic stimulus so as to produce raw reaction data, which raw reaction data may include a magnitude and an orientation of the response of the nerve. Likewise, the transcutaneous sensing and monitoring device may include a communications module for transmitting the sensed raw reaction data.

Additionally, the system 100 may include a computing device 110A, such as a computing device that is part of or otherwise coupled to the transcutaneous sensing and monitoring device 105. As indicated, the computing device 110 or 110A may be configured for receiving the raw reaction data, evaluating the raw reaction data, and determining one or more characteristics of the neuropathic nerve to be targeted. In various instances, the computing device 110 or 110A includes a set of processing engines for processing the raw reaction data in a variety of manners using a plurality of different combinations of sensor elements 160 so as to triangulate and/or trilaterate which sensor elements pick up the strongest responses and in what orientations.

For instance, a first processing engine, or set of processing engines, may be provided, such as for receiving the raw reaction data from a first unit of a plurality of sensing elements of the transcutaneous sensing and monitoring device. Particularly, the first sensing unit may include a first set of sensing elements, such as a first of at least two or three, or four or five, or six or more, sensing elements. A variety of raw data may be collected, such as raw reaction data that includes an amplitude, magnitude, direction, and/or orientation data, such as from each or a selection of sensing elements. This data may be in a raw form and may be used to characterize the response of the neuropathic nerve to the applied magnetic stimulus. In such an instance, the first processing element may be configured for integrating the direction, magnitude, and the orientation data from each of a selected set of sensing elements of the first sensing unit. Hence, the first sensing element or set of sensing elements may be configured for determining a first integrated magnitude and a first integrated orientation for the first unit.

Further, a second processing engine, or set of processing engines may be provided, such as for receiving the raw reaction data from a second unit of sensing elements. As per above, the second sensing unit may include a second set of sensing elements, such as a second set of at least two or three, or four or five, or six or more, sensing elements. Like above, the raw reaction data will include amplitude, magnitude, direction, and/or orientation data, such as from each or a selection of sensing elements, such as for further characterizing the response of the neuropathic nerve to the applied tMS stimulus. The second processing element, therefore, may be configured for integrating the direction, magnitude and orientation data from each of the sensing elements of the second sensing unit, and may further be configured for determining a second integrated direction and/or magnitude and a second integrated orientation for the second unit. These processes may be repeated for a number of different selections of sensing units including a number of different combinations of sensing elements, all producing a wide variety of sensor data having different strengths of magnitudes in different directions and having different orientations, such as in three-dimensional, X, Y, and Z space.

Furthermore, a third processing engine, or set of processing engines, may be provided for receiving the first and second, as well as any and all other integrated direction and magnitude data, and may further be configured for determining which collection of sensing units, and which sets of sensing elements thereof, evokes or otherwise evidences the greatest magnitude. The same or a different processing engine may then be configured for evaluating the sensed magnitude data and associating a weight to the evaluated data points, such as where greater weight is given to the sensing unit, as well as to the sensing elements thereof, evidencing the greatest results data, e.g., with respect to amplitude and/or magnitude of response. Lessor weighting may then be attributed to all the other sensing units and sensing elements.

Further still, a fourth processing engine, or set of processing engines, may be provided, such as where the fourth processing engine is configured for receiving the first and second and any additional integrated orientation, evaluating the same, and associating weights to individual data points, where a greater weight is given to whichever orientation is correlated with orientation data received by sensing elements of the sensor units evoking the greatest response, e.g., evidencing greater magnitude. Lessor weighting may then be attributed to all the other sensing units and sensing elements. A fifth processing engine, or set of processing engines, may also be present for receiving and evaluating respective integrated magnitude, integrated orientation, and other collected data, e.g., integrated direction and amplitude data, as well as the weight data for a plurality of sensing units, and determining a set of coordinates defining the neuropathic nerve to be targeted, such as based on the evaluated magnitude, orientation, other collected data, and weight data. A sixth processing engine, or set of processing engines, may be provided such as for determining a first treatment protocol for administering the focused magnetic stimulation to the neuropathic nerve to be targeted so as to thereby ameliorate neuropathic pain experience, such as where the first treatment protocol may include a proposed orientation of a tMS application device relative to the neuropathic nerve to be treated and/or an amplitude, or other waveform characteristic, of the focused magnetic stimulation to be administered.

Specifically, before, during, or after, one or more nerve tissues have been identified and/or mapped with respect to one another in the target region, a magnetic pulse may be applied to the identified and/or targeted cells within the target site, such as by positioning, orienting, and/or activating the tMS applicator such that a magnetic pulse is generated and directed to the targeted nerve fiber(s), e.g., to one or more A-β fibers. For instance, once one or more nerve fibers have been identified and/or classified, such as to type of pain fiber, the activity of the identified fiber can be characterized and monitored over time, and based on the nature of the treatments the parameters of the treatments to be administered can be determined with respect to the waveform characteristics, such as with regard to the amplitude, hertz, and/or the like of the magnetic field administered.

Particularly, an initial frequency of delivery can be selected based on its ability to evoke a response, e.g., a potentiation, in a wide variety of nerve fibers, such as between 0.001 Hz to about 1 or about 2 Hz, which should stimulate a wide variety of nerve fibers, and 3 or 4, e.g., 4.5, or 5 or 6 Hz up to about 10 Hz or more, which actuate a much smaller range of nerve cells. Likewise, the amplitude and/or duration of the administration, e.g., such as from about 1 or 2 minutes to about 15 or about 20 minutes, such as from about 5 to 10 minutes, including about 7 or about 8 or about nine minutes can also be selected and modulated so as to either generalize and/or personalize the administration of the treatments.

Various characteristics of the subject, such as age, metabolism, weight, and the like can be used to determine initial administration parameters. For instance, in any particular instance, a given subject may or may not adapt well to the treatments. In either instance, the parameters of the treatment may be recorded and/or a change in parameters can be determined and measured so as to account for the occurrence of one or more trends, such as a trend that does or does not lead to a reduction of pain. For example, in one particular embodiment, a first administration to ameliorate pain may be administered in accordance with a particular set of delivery parameters, e.g., at 4 or 5 Hz for 20 mins, but the subject, e.g., patient, may respond well to the treatments, and with adaptation thereto, such as over time, subsequent administrations may only need to be delivered at 0.5 or 1 Hz for about 3 or 5 minutes. Hence, this shows a positive trend that can be tracked and predicted so as to more closely align the treatments to the individual's personal response thereto.

In such an instance, due to adaptation or priming to the delivery parameters, the system can not only effectuate pain relief much quicker, using less energy, but may also increase the sensation of pain relief experienced by the subject, such as at 2×, 3×, 4×, or more. The reverse, such as a negative trend, may also be identified and tracked, and the system parameters modified to respond or otherwise correct for the negative trend. As described herein, one or more of these parameters can be determined, such as in a time-dose optimization regime, can be tracked, and the delivery parameters may be adjusted, upwards or downwards based on an observed or determined trend.

Accordingly, a further aspect of the disclosure is directed to a method for determining one or more delivery characteristics of the focused magnetic stimulation to be administered to the target nerve in the target area in the body of the subject experiencing neuropathic pain, such as for alleviating the neuropathic pain experience. The method may include coupling the transcutaneous sensing and monitoring device 150 to the body 1000 at the area of pain experience. As indicated above, in particular instances, the transcutaneous sensing and monitoring device 150 may have a plurality of sensing units 162 such as where each sensing unit 162 includes a plurality of, e.g., at least tow or three, sensing elements 160 that may be arranged so as to form a grid having both rows and columns of sensing elements, such as 2, 3, 4, 5, up to 10 or more rows and columns of sensing elements 160. Each sensing element may be configured for identifying the reaction of the nerve to the applied magnetic stimulation so as to produce raw reaction data, such as where the raw reaction data may include a direction, an amplitude, a magnitude, and/or an orientation of the response.

Once the tMS or other sensing device 105 has been coupled to the body 1000, a magnetic stimulation may be applied, e.g., by a mobile tMS application device 105, to the area of pain experience in a manner so as to provoke a reaction in the target nerve in such a manner that a response thereto by the nerve to be targeted may be sensed by one or more of the sensing elements 160 of the tMS sensing device 105. Accordingly, subsequent to applying a magnetic pulse to the target area, the transcutaneous sensing and monitoring device 105 will collect the raw reaction data from the plurality of sensing units. The collected data may then be processed and evaluated, such as by a processing element onboard of the sensing device and/or by a computing device associated therewith, and the sensor element 160 and sensor unit data, e.g., from a selection thereof, may be determined and integrated in such a manner that a plurality of integrated sensor unit data is produced. In such an instance, each individual and/or integrated sensor unit data may include an integrated magnitude and an integrated orientation of the response detected by the sensing elements 160, e.g., of each of the plurality of sensing units 162.

The computing device 110 may then compare the integrated sensor unit data collected from a selection of the sensing units 162, one with the other, so as to produce a set of comparison results. The computing device 110 evaluates the results of the comparison and then determines a treatment protocol for the delivery of the focused magnetic stimulation to the targeted nerve. For instance, in various instances, the treatment protocol may define one or more delivery characteristics, such as a set of coordinates defining the nerve to be treated and/or an orientation for orienting the tMS application device 105 relative to the target area 1000 and/or target nerve. In particular instances, the computing device 110 may determine one or more application parameters that may be used in generating the magnetic pulse. As indicated, the magnetic pulse may be engineered to have one or more determined waveform characteristics. In such instances, the one or more application parameters may include a voltage level and a current level, such as for generating a desired magnetic pulse, e.g., where the magnetic pulse is defined by a wavelength, frequency, amplitude, and duration of the magnetic pulse, which may all be selectable.

Accordingly, once the treatment area and the appropriate dosage regime have been determined, such as prior to the application of magnetic stimulation, the system may be configured to align the applicator to the determined treatment site for treatment thereof. For instance, where the system includes a tMS applicator 105 and a positioning element 140, such as an articulating member, described above, the device may be configured so as to position and orientate the tMS applicator 105 in such a manner as to align it to the treatment area and/or treatment site. This may be done autonomously or may be done through instructing a system operator to configure the system appropriately.

Particularly, the system 1 may be configured so as to specifically align the one or more coils 115 of the applicator 105 to the target site so as to be angled with respect thereto so as to effectively administer the magnetic flux to the treatment site in a precise and targeted manner. In a manner such as this, the angle of the applicator and/or coil(s), the frequency of the flux, as well as the magnitude of the magnetic wave can all be modulated so as to determine the maximum effectiveness of the treatment with respect to the nerve fiber of the subject to be treated. More particularly, once the pain causing nerve fiber(s) has been identified, the pain fiber of interest may be mapped such that the system 1, e.g., via the tMS applicator 105 and/or sensing device 150, is able to lock on to its conductance signal, and then position the positioning element in appropriate three-dimensional space so as orientate the tMS applicator 105 so as to effectuate targeted delivery of a magnetic field to the affected nerve fiber.

Accordingly, in one aspect, once the nerve in need of treatment is located, targeted, and/or mapped, and the orientation and suitable impulse characteristics of the tMS application have been determined, then one or more calibration procedures may be implemented, so as to calibrate the tMS applicator to the treatment site, such as prior to the delivery of treatment. For instance, prior to diagnosis and/or treatment, a calibration and/or initiation protocol may be run, whereby a few initial magnetic and/or electric pulses of defined characteristics may be emitted and directed to the cover and/or sensor, such as directed at a treatment area of the body, so as to verify and characterize the output and calibrate the tMS applicator 105 and/or system 1.

For example, once the defined pulses are emitted from the tMS applicator 105, they may be received by one or more calibrations sensors, such as in the cover and/or tMS sensor device 140. The characteristics of the received pulses can then be compared to the defined characteristics. Using the results data from this comparison, the system components can be modulated so as to calibrate the system and/or correct for any differences between the defined and the received pulses.

Prior to calibration, the tMS sensor module 150 may be positioned near the treatment area, and a protocol for calibrating and/or identifying the target nerve may be initiated. For example, communicating with the tMS sensor module 150, the positioning element 140 can translocate the tMS applicator 105 proximate the target area 1000, using initial determined coordinates of the nerve fiber, at which point one or more magnetic pulses may be delivered to the nerve fiber by the applicator, so as to activate the nerve fiber. The activation of the nerve fiber will cause a conductance response in the nerve, which conductance can then be sensed and characterized by the sensor module. In such an instance, the feedback from the nerve may be picked up by the sensor module 150, which may then be processed therein and/or be communicated back to the tMS system 1 and/or applicator device 105 for recalibration and/or continued, e.g., more focused, targeting and/or treatment application.

Particularly, for the purposes of calibration, a unique sequence of pulses may be emitted from the tMS applicator 105. In various embodiments, the characteristics of the pulses are selected and/or are otherwise configured for identifying the nerve of interest and differentiating it from other non-target nerves in the treatment area. Likewise, once targeted, the system can then calibrate the pulses to be applied to the target nerve fiber itself, such as for determining the ideal characteristics of the magnetic and/or electric pulses to be applied to the body tissues, such as with respect to its waveform, frequency, amplitude, and the like.

Specifically, once an initial targeting protocol has been implemented and/or the appropriate waveform characteristics have been identified, a more precise targeting procedure can be executed, as described above. In this manner, as described above, one or more locations on a grid may be identified, based on responsiveness to the targeting pulses, and then through a repetitive, iterative process the nerve fiber to be targeted can be mapped out. Once mapped out the characteristics of the pulses can be calibrated to maximize delivery effectiveness. More specifically, during this process the unique waveform of the conductance within the nerve fiber can then be used to identify and further map the target nerve fiber, such as by its unique pulse sequence, and the target nerve fiber can be distinguished from its neighboring nerve cells.

Accordingly, in this manner, the pain causing nerve fibers of interest can be identified and mapped out by their unique response to the pulse sequences, and then the magnetic pulse applicator can be calibrated, and one or more treatment pulses can be administered for the alleviation of the experience of pain from the subject. The recited calibration can be performed so as to determine the optimal treatment waveform for pain alleviation, such as with respect to frequency, wavelength, amplitude, device orientation, and the like. More specifically, in one instance, once a maximum amplitude has been determined, an effective and efficient pulse sequence can be determined.

Likewise, once one or more of the target nerve fibers, e.g., A-β fibers, has been determined, its other neighboring fibers, e.g., A-α, A-δ, and C fibers, can then be mapped out, such as by extrapolation. During one or more of these iterations, the tMS sensor device 150 may be repositioned, and/or chained with other sensor devices, so as to better triangulate, trilaterate, and define the target area and zero in on the treatment site. In this manner, the tMS sensor module 150 may be positioned proximate the treatment site and can be used in combination with the tMS applicator 105 to finely tune and direct treatment to the target nerve, and the concomitant response in the nerve can be used to further map the nerve, calibrate the system 1, and position the tMS sensor 150 and applicator 105.

Hence, once the axon protect cover 108 has been positioned on the tMS applicator 105, if desired, and the device calibrated, the positioning element 140 can be actuated to position the tMS applicator 105 adjacent the target area 1000 and adjoining the tMS sensor device 150. After being appropriately positioned and orientated, one or more pulses may be delivered to the treatment site, such as directed to the nerve fiber of interest, so as to activate the nerve. Feedback from the activated nerve can then be sensed by the sensor unit, and a localization protocol can be implemented to zero in on the target site, such as through a triangulation, trilateration, and the like, process described above.

Specifically, one or more arrays of the sensor device 150 may be activated so as to determine which of the multiplicity of sensors 160 is receiving feedback with the greatest signal strength. Through an iterative process of activation and sensing, a grid-like representation of the morphology of the target nerve within the tissue of the target area may be mapped and defined. If not already performed, a calibration sequence of unique pulses may be implemented to refine the magnetic and/or electric field being applied to the nerve to effectuate an optimized pulse delivery to the nerve so as to better produce pain amelioration.

A unique feature of this process is that through the mapping procedure an objective determination of the positioning of the nerve within the tissue may be defined in a manner that delineates the sub-tissue coordinates of its dimensionality, which coordinates can then be used to target the nerve in a precise manner through subsequent treatments. This makes treating pain much more objective, repeatable, and efficient, thus, requiring less time and energy, especially where the positioning and application is performed autonomously by the system controller, e.g., as determined and implemented by the AI module of the system.

Accordingly, one or more of the systems presented herein may be configured for collecting various data so as to generate and implement a treatment protocol and to measure and track a pain experience of a subject through one or more treatment procedures. In this regard, in response to an applied magnetic stimulus the targeted nerve may respond by depolarizing in a manner that can be sensed by one or more sensor elements 160 of the tMS sensor device 150. Specifically, the amplitude of the response of the nerve depolarization may emit a signal, e.g., an amplitude signal, that can be sensed by various sensors elements 162, e.g., electrodes and magnetometers, which once the nerve fiber has been triangulated, the signal, the depolarization within the A-β nerve, can be maximized, such as by optimizing the position and/or orientation of the tMS device 105 and its coils 115.

Particularly, the system 1 can be configured to solve for the space into which the magnetic coil 115 is to be positioned with respect to the targeted nerve fiber so as to maximize the response within the nerve cell to the magnetic pulse. More particularly, the positioning of the tMS applicator 105 can be defined, with regard to the X, Y, and Z axes (space), along with rotation around each of the same, such as with respect to the coordinates of the target nerve. This data can be determined based on increasing the amplitude and frequency of the applied magnetic pulse that results in the greatest decrease in the experience of pain, such as in a gradient descent computation.

The results of these computations can then be used, such as in a linear regression optimization model, so as to determine the best configuration of the tMS applicator 105 vis a vis the target nerve, so as to maximize the amplitude of the response of the nerve to the emitted magnetic pulse. In the described iterative process, various characteristics of the waveform and its generation may be produced, and a protocol for defining various administration parameters, e.g. waveform variables, can be determined and correlated such as with respect to how one or more of the identified nerve fibers, e.g. A-α, A-β, A-δ, C fibers, and the like, nerve is functioning in regard to activation and/or depolarization characteristics related to one or more of the height of the amplitude, pulse width, slope, frequency, positioning, e.g., coordinates, impudence and/or resistance of the coils, the voltage to be applied, and the current employed, all of which can be determined by the system, e.g., an artificial intelligence (AI) module of the system 1.

For instance, upon placement of the sensing and stimulating devices on/or proximate the body, the AI of the system will then determine the location of the target nerve and the ideal positioning and/or orientation of the stimulatory device for maximal effect. In this manner, the system characterize pain, correlate the pain to history of patient, then treat the pain, and in its resolution define what the cause of the pain was, what the treatment was, and why the treatment resolved the experience of pain. This data can then be collected by the system, can be analyzed, and can be used, through an iterative process of increasing and/or decreasing one or more of the variables, such as amplitude, frequency, and the like, during the treatment process, such as on a step by step basis, so as to characterize the positioning of the nerve, its morphology, and the conditions that affect it. These iterations can be repeated again and again so as to maximize the reduction in pain while minimizing the time take to decrease that pain, while at the same time as increasing the period during which no pain is experienced.

Hence, in view of the above, once a maximum amplitude for pulse delivery for a given target nerve has been determined, then an enhanced pulse sequence can be determined and implemented, e.g., to verify the nerve of interest to be treated. Likewise, once the target, e.g., A-β, nerve has been identified, then the positioning of the other background nerve fibers, e.g., A-α, A-δ, and C fibers, which are not of interest, can be extrapolated, and once their location and/or positioning is known, then any reactivity of these fibers can be sensed and subtracted as background noise from the response of the A-β fiber of interest. Particularly, a baseline of nerve reactivity can be established, background nerve activity can be minimized, and the reactivity of the nerve of interest can be used to better hone in the system for delivering a magnetic and/or electrical field more precisely to the target nerve.

In this manner, as the honing continues, the reactivity of the A-α, A-δ, and C nerve fibers should decrease, and the reactivity of the target A-β fiber should increase, thereby making targeting much easier. Consequently, the implementation of the treatment process becomes more and more optimized the more treatment is administered, and likewise, the more the target nerve will become potentiated, the less the amount of stimulus will be needed, and the greater effectiveness can be rendered prior to nerve fatigue. Fatigue can also be monitored and the system can be optimized for predicating and reducing the onset of nerve fatigue in the same manner as above so as to allow for hyperpolarization.

In another aspect, as discussed above, the system may be configured so as to perform one or more diagnostics on the subject, such as to determine the presence of neuropathy and/or to treat the effects of such neuropathy. For instance, as discussed above, there are several different nerve types, and likewise, there are several different conditions that affect nerves in such a manner so as to cause pain to a subject having the condition. Specifically, having a form of neuropathy causes an imbalance in the subject's nerve processes, the system, therefore, can be configured for determining such an imbalance and in response thereto a treatment regime may be generated and applied by the system so as to bring the subject's system, e.g., one or more nerves thereof, back into balance, such as autonomously or through manual operation.

Hence, the system may be configured for not only optimizing its own system parameters, and optimizing system parameters for use in delivering treatments to each particular subject, but may also be configured for determining one or more neuropathies so as to better determine how to treat pain sensation and for optimizing nerve functioning of the subject. Consequently, the neuropathic conditions of the subjects treated may be characterized with respect to the various variables of their condition, which variables can be used to diagnose and treat the subject, and further used to diagnose other subjects evidencing the same variable conditions, such as with respect to both subjective and objective variables experienced by the subject, such as their experience of pain and pain alleviation and the objective characteristics of their conductance waveform of their nerves, e.g., before and after treatment. This data can then be used to optimize treatment delivery both generally, for a class of subjects or clients, and specifically, for each individual client.

Additionally, the data can be employed, and new data collected, when monitoring the subject post treatment, to further personalize the treatment regime for each individual client. Specifically, in addition to treating nerve pain, the present system is especially useful for diagnosing hard to determine nerve damage, alleviating the frustration of a subject having to go from doctor to doctor in search of an explanation of a pain that apparently seems to defy diagnoses. And once an appropriate diagnosis has been made, by the systems and methods disclosed herein, a treatment regime can then be implemented. Based on the sensed data, and/or subject feedback, one or more neuropathies can be determined and treated.

The results of the diagnosing and treatment can be saved within an associated database. Hence, a database of maladies may be generated, cataloging the diagnoses and treatments of a plurality of subjects, which database can then be used by the system to perform a diagnosis on one or more subjects, such as by comparison of conductance characteristics between a current subject to be assessed and/or treated and past subjects that have been assessed and/or treated. Accordingly, once an assessment has been performed, the system can then be configured, e.g., by a system administrator or autonomously by the system itself, and one or more treatments can be performed in accordance with the assessment. Treatments may be applied to the target area of the subject in need of such treatments for the amelioration of the sensation of pain. For instance, when a subject comes in for treatment, one or more assessments can be performed, such as in conjunction with using the sensing device and tMS application systems disclosed herein.

Particularly, a sensing apparatus may be positioned on the subject's body, proximate the target area, the tMS applicator can be orientated to the one or both of the sensor and applicator, and a series of pulses can be applied to the body. For example, initially, over the first visit, a diagnostic procedure can be performed. Specifically, in preparation for treatment, a diagnostic regime may be implemented so as to determine the presence of one or more neuropathies in a nerve to be treated.

In a first step, a sensor module, as described above, may be positioned on the body at the area where pain is being experienced, the protective cover can be placed over the tMS applicator device, the tMS applicator may be positioned near the tMS sensor and proximate the tissues of the treatment area, and one or more calibration and/or diagnostic pulses may be administered to the body, directed to the target area where the neuropathic nerve is expected to be. As explained above, in one embodiment, to initiate activation of the tMS system the protective covering may be positioned at the head of the tMS applicator. As indicated, the system may be configured such that the placement of the protective cover over at least a portion of the head of the tMS applicator results in the activation of the tMS applicator.

For instance, the protective cover can be intelligent, or at least include one or more of a microchip, sensor, battery, one or more coils, such as a passive coil, and/or a transceiver. Once the cover is coupled to the applicator, a signal may be sent from one device to the other, which signal represents an activation code authorizing use. For example, in one embodiment, an initiating signal may be sent from the tMS applicator, such as a limited magnetic pulse, which signal can be received by the cover, and in response thereto a return signal can be sent from the cover to the applicator so as to activate the system.

More particularly, where a magnetic pulse is sent from the tMS applicator, when received by the passive coil of the cover, induces a current therein that energizes the transceiver which then sends an authentication code to the system controller activating use of the tMS applicator, such as in a once per use model. In various embodiments, the cover may include a radio-frequency identification (RFID) tag, and the tMS applicator (or tMS sensor) may include an RFID reader such that as the two come into proximity of one another a verification signal is sent and received and the system is activated. In particular instances, the cover may include one or more magnetic sensors that can detect the presence of a magnetic field, which may then cause activation of a return authentication signal being transmitted, and/or may be used to calibrate one or more of the tMS applicator and/or sensing device. It is to be understood that this authentication between the protective cover and the tMS applicator can also be implemented in reverse order and/or may be implemented using the tMS sensor unit.

Accordingly, in a typical treatment protocol, a subject, e.g., a patient, will come in and a cover may be placed over the tMS applicator coils, so as to protect the applicator and the subject to be treated. Treatments can then be administered and the activities of the various nerve fibers can be determined and/or monitored. In a manner such as this, once the neighboring nerve tissues have been identified, the responsiveness of the target nerve fiber can be better resolved such as by removing any responsiveness of the neighboring nerve fibers, e.g., constituting noise, from that of the target nerve fiber, such as by extracting the noise from the target conductance. This process may be repeated a number of times, such that over time the treatments become more focused and more resolved, as it becomes clearer where the target nerve fiber is, and the noise of the neighboring nerve fibers can more easily be identified and filtered.

Specifically, the better the target nerve fibers are resolved, the more focused the stimulatory pulses can be delivered, and the more focused are the stimulatory pulses, the less will the neighboring fibers will be activated and the less noise will be generated, making filtering easier, and resolution of the target nerve fibers even better. This resolution is useful because it can then be more easily determined when the target nerve has become fatigued, and is no longer responding to the magnetic pulses, at which time a break in application can occur, and after a suitable rest period, treatments can be renewed again, such as with a modified inductive waveform so as to avoid hyper polarization. Likewise, in various embodiments, the one or more magnetic pulses may also be employed so as to increase perfusion in one or more vessels in the target area, such as where the target area has suffered both nerve and vessel damage. By increasing blood flow to the treatment area, healing can be expedited.

Further, in various instances, the energy to be applied to the treatment area may be sonic energy, which, in some instances, may be employed so as to visualize and/or image the treatment area, and the tissues and vessels therein, but in other instances, may be configured for targeting sonic energy, e.g., sound waves, to the target nerve or vessels. For instance, in various implementations, the applied sound waves may be directed to the vessels so as to breakup and/or treat blood clots, atherosclerosis, and the like.

In another aspect, the system may be configured to monitor one or more nerves, such as via the tMS sensing device. For instance, in one embodiment, a monitoring system is provided. The monitoring system may include a tMS sensing device, such as described herein, where the tMS sensing device is configured for monitoring a nerve activity level. For example, the tMS sensing device may include a sensor module having a set of sensor modules. So being, the sensing device may be positioned proximate a treatment area, whereby one or more sensors of the sensor module may be configured for identifying the activity of one or more nerves so that the tMS applicator can be appropriately aligned to identified target site. In various embodiments, the sensor module can then communicate with the tMS applicator so as to indicate how, where, and in what configuration and/or orientation the magnetic field should be applied to the target site for the delivery of treatments in the correct form to the specifically identified nerve cell(s).

As described above, the sensor device may include one or more sensor modules having a plurality of sensors that are configured for performing a triangulation and/or trilateration operation. For instance, one or more sensor modules may be configured for triangulating a selected nerve cell, and in various embodiments, a plurality of sensors, in one or more sensor modules, may be adapted so as to form a nerve identification and registration system. Further, as discussed above, in various embodiments, the sensing device may include an imaging module having an image capturing element, such as where the image capturing element, e.g., imager, may be configured to capture one or more images of the sub-tissue structures within the treatment area, such as the nerve cells of interest. In such an instance, as discussed above, the imager may be an optical or sonic element that is adapted for capturing an image, such as a 3-D image of the nerves and/or other vessels and structures within the target area tissues.

In a manner such as this, the target nerve cells, e.g., A-β nerve fibers, can be identified, located, registered, and defined, such as by the sensor registration system, in a manner such that the sensor module can then communicate to the tMS applicator where and in what orientation to deliver the magnetic pulses. Hence, in such an instance, based on the registration process, the location and/or morphology of one or more nerves, such as in tissues within the target area, can be identified and used to locate and define not only one or more nerves but the treatment site as well.

In a manner such as this a nerve to be treated can be identified, located, and mapped so as to be particularly targeted for treatment in a systematic and repeatable fashion. This may be repeated a number of times, e.g., along the tissues and/or nerves, such that multiple areas of a nerve of interest can be targeted for treatment, such as along the course of the body, such as in a sensor device chaining process, described below.

Such targeting can be used to direct the positioning of the tMS applicator device, such as via the moving of a positioning element associated therewith, either manually or electronically, so as to properly align and orient the tMS applicator to each treatment site, such as in a sequential manner, such as over a plurality of treatments over a number of different times. For instance, as discussed above, in performing an identification process, a unique pulse sequence can be applied to the nerve cell, e.g., by a tMS applicator, and an expected response thereto can be detected, e.g., by a tMS sensor, so as to identify or verify the nerve fiber, to identify and/or characterize a degree of damage to the nerve, e.g., based on its conductance characteristics, and/or determine a diseased state.

For example, a test pulse can be delivered in order to find a base level response when pain is experienced and then again when pain is not experienced, and the characteristics of the conductance of the nerve in these two conditions can be stored in the system and used thereby to predict future pain onset, such as when the treatment is wearing off and how fast, which can then be used to automatically schedule the subject for another treatment. Particularly, as indicated, a unique pulse sequence can be applied to locate and identify the nerve of interest, e.g., A-β, and a series of different energy pulses, such as magnetic or electric field pulses of varying waveform, e.g., different frequencies, wavelengths, amplitudes, and the like, can be delivered to first identify the nerve and to characterize its relative health. In one particular exemplary embodiment, 2 or 5 or 10 or 15 or more pulses can be delivered at about 0.5 to 10 or 15 to about 20 or more Hz, and over the course of about 1 to about 10 seconds, e.g., in an iterative sequential sequence, and the nerve's responses thereto can be used to categorize its health, relative its own baseline, the collective baseline of a sample, e.g., all, of those equivalent nerve types in the subject, and/or relative to a database of nerve types over a wide sample of subjects. And of course, once a baseline and/or neuropathic condition has been established by the system, then the tMS sensing device can be employed to monitor the nerve's condition over time, such as throughout the course of the day, the week, the month, the year, and the like.

Accordingly, in various instances, the system may be configured for monitoring and characterizing nerve fiber activity such as in response to a stimulating event, where the nerve fiber activity can be characterized with respect to the frequency, wavelength, amplitude, speed, and the like of the nerve fiber's conductance. Specifically, a tMS sensing device may be positioned on a subject's body and can be configured for monitoring and characterizing nerve fiber activity so as to determine an increase or decrease in spikes of conductance activity, such as where an increase or decrease in nerve activity causes an increase or decrease in pain, which may then be transmitted to the system or monitor thereof so as to notify one or more system users that a pain causing or pain diminishing event may just have occurred, such as due to damage done to nerves in the target area.

In various embodiments, in response to a stimulatory event, a decrease in nerve activity can be identified, which decrease in nerve activity, such as in a monitored A-β nerve fiber, results in an increase in pain experience, and likewise, a stimulatory event may cause an increase in nerve activity, such as in a A-β fiber, which increase in nerve activity results in a decrease in pain experience. The opposite configuration may also be monitored, such as where an increase in stimulation of a nerve fiber, such as a C fiber, results in an increase in pain, whereas a decrease in stimulation results in a decrease in pain experience. The stimulatory event may be caused by the application of a magnetic and/or electric pulse, such as applied by a tMS applicator of the system, or may be caused by an activity performed by the subject wearing the tMS sensing and monitoring device.

In various instances, a plurality of tMS sensor devices may be applied to the body, in a variety of different positions, where each sensor device includes a communications platform that is configured for allowing each sensor device to be communicably coupled with one another, thus, allowing the sensing devices to be used in concert for triangulation, trilateration, mapping, treatment delivery, and/or the like, such as where the nerve to be treated spans a plurality of regions of the body, and/or has multiple loci of injury. For instance, in many instances, sensor module chaining is useful because it facilitates identifying a nerve of interest, and for performing a mapping operation, and is further useful in providing multiple treatments to the same or different body parts in concert or synchronously. Particularly, in various embodiments, one tMS sensor device and/or tMS applicator can be positioned so as to apply treatment at a treatment site, and another set can be positioned at a different portion of the body, such as proximate a portion of the spinal cord, where in such instances, different portions of the nerve can be monitored and/or treated together, e.g., simultaneously or sequentially.

Hence, in one exemplary embodiment, if a nerve in the leg is to be treated, three sensor devices and/or applicators may be applied to the body, such as behind the knee, at the waist, and at the spine, and one or more, e.g., all three, sensors can be used to target the nerve so that treatments can be delivered to the length of the nerve at the same time, or in sequence, or iteratively, and the like. Such delivery at multiple treatment sites of the same nerve has been found to be especially useful in alleviating the experience of pain. In such instances, positioning a sensor module both at the site of pain and at a site of the spinal cord may be particularly useful, such as for applying magnetic and/or electric pulses along the course of a nerve fiber, e.g., from the locus of pain and the location at where the nerve interfaces with one or more nerves of the spinal column.

In some instances, a sequential or iterative application of a magnetic pulse may be desired, and hence, the automatic positioning element of the tMS device may be configured for repositioning itself, e.g., via communication with the sensor modules, so as to move from a first target site demarcated by a first sensor module, and then move to another, and/or another treatment site, until all treatment sites have been treated. For instance, once identified and/or mapped, a nerve targeted for treatment may be identified, and re-identified, prior to treatment to ensure that the appropriate nerve is to be treated. This verification process can be initiated by aligning the tMS applicator proximate a sensor indicator at a treatment area, and delivering a verification pulse to the nerve, such as in a known pulse sequence, and comparing its conductive response thereto to a known response thereof, such that if the responses correspond, then it is known that the correct nerve to receive treatment has been appropriately targeted.

As noted above, such pulses may also be employed so as to diagnose a diseased or injured state and/or to assess damage of the nerve fiber, for example, diagnosing a diseased or injured state and/or a degree of damage. In an exemplary embodiment, 2 or 5 or 10 or 20 pulses, from about 0.5 to 10 Hz can be delivered to one site on one nerve so as to clearly differentiate baseline activity of the target nerve from its neighboring, non-targeted nerve fibers, and of course once its identity is known its morphology, such as structural characteristics may be defined, and the coordinates recorded by the system for future targeting and treatment.

Accordingly, given the sensor devices having the sensor modules disclosed herein, pain can now be quantified, monitored, and tracked before, during, and after treatment, both subjectively and now objectively, such as by determining one or more spikes or drops in nerve tissue activity, such as where the change is indicative of a pain occurrence above an identified threshold. Particularly, subjectively, a subject to be treated may identify a sensation of pain, and may quantify that sensation on a system generated scale or other form of data entry, such as a numerical scale from 1 to 10, then a measurement of nerve activity can be taken and can be associated with the subject entered data and used to give an objective component to the subjective entered data. Likewise, these data may be used to establish a baseline of pain and pain tolerance for the individual subject.

Further, the system may be configured for measuring and monitoring pain amelioration over one or more treatments to the subject, both objectively and subjectively. For instance, once a baseline for an experienced pain sensation has been determined, then one or more treatments may be administered to the subject, and a subjective measurement may be taken, such as via a questionnaire or filling out a pain threshold scale, and then nerve activity can be measured again and these results can be compared to one or more earlier results. Specifically, prior to treatment the conductance of the various nerve fibers in the target area can be measured and determined, such as by measuring the characteristics of the conductance taking place in the respective nerve fibers. More specifically, the waveform of the conductance through the nerve fiber, e.g., its amplitude, wavelength, frequency, and/or the like, can be measured and used to characterize the sensation of pain.

Likewise, the tMS applicator, discussed herein, can then be used to administer magnetic pulses to the treatment site, and the nerve activity during and/or subsequent to treatment can then be measured by the tMS sensing and monitoring devices, e.g., with respect to the characteristics of the conductance occurring in the activated nerve fibers, such as with respect to the amplitude, wavelength, and/or frequency of its waveform. From this data the subjective and/or objective characteristics of pain can be determined, measured, monitored, and tracked, and thereby the effectiveness of treatments can be determined and/or a treatment regime determined and effectuated.

A unique feature of the present devices, systems, and methods disclosed herein, therefore, is that it has been determined that focused administration of magnetic pulses to the A-β nerve fibers at a locus of injury or pain can activate the nerve fibers, which activation leads to an amelioration of pain, which can last for hours, days, weeks, and even months, such as until a new injury occurs to the nerve fiber and/or the nerve fiber returns to its pre-treatment state. Accordingly, in various embodiments, the tMS sensor devices disclosed herein may be configured so as to be wearable, and as such, may be configured for monitoring nerve activity and pain over time. Such monitoring may be performed directly by the device, and the generated data stored thereon, and/or the data may be transmitted to a client computing device, such as a paired mobile phone or tablet computer, or to a server, which monitoring may be employed so as to track the health of the subject over time and distance.

Particularly, with the activation of the A-β fibers at the locus of pain, a renewed sense of health can be obtained, and because of this sensation of health, the subject having been treated may feel they are capable of engaging in activities they would not otherwise be able to engage in, which in some instances may cause a renewed injury to the pain causing fibers, which will be picked up by the wearable sensor, quantified, and if a given threshold, e.g., pain tolerance threshold, has been breached, the subject can be notified that a new treatment regime should begin. Likewise, in certain instances, the system's activation of the A-β fibers may last for a period of time, but may eventually decay, which may in turn result in an increase in C-fiber activity and the onset of pain once more, this diminution on A-β fiber activity and/or increase in C fiber activity can be observed, determined, and/or monitored by the wearable sensing device and/or monitoring system, and when a given threshold is evidenced, a warning signal may be sent to a system administrator and/or to the subject being treated. Such notification can be performed by the system, e.g., automatically, and can be delivered via a phone call, text, SMS, direct messaging, posting, e-mail, and the like, such as to the wearer of the device or a health professional monitoring the same, and the like.

Feedback can also be elicited from the subject so as to qualify the context of the pain event both biologically within the subject, e.g., at the locus of pain, and/or environmentally, as in what they were doing to cause the pain, when, where, and how, and the like. In a manner such as this, the system can track the daily activities of the subject, and associate a pain profile to one or more, e.g., each of the activities engaged in, such as where pain is experienced, and where a spiking of pain occurs, this can be tracked, and feedback given to the subject of treatment. For instance, the system can determine a regular pattern of behavior for the subject, and where a determined activity that has been identified as causing pain, e.g., acute pain, or having the potential to do so, this can be tagged by the system and a warning may be transmitted to the subject, and where the activity does cause the predicted pain, then a treatment may be set up on behalf of the patient such that after the activity, a new treatment can be administered so as to reduce any pain cause by the activity.

Specifically, the difference in activities may result in different conductive characteristics of the nerve fibers, such as where an activity leads to acute or chronic pain onset, causing different characteristics of wave form and function that can be identified with those activities and tracked. Hence, chronic pain sensation can be monitored and tracked, and where an acute pain episode is experienced or predicted, or a diminution in chronic pain cessation is predicted, the system may identify and warn of a change or potential change in the health status of the subject, such as prior to when a flare up occurs.

In a manner such as this, the system can track pain and activities correlating the two together, so as to generate a user activity profile, which can be used to determine a regular treatment schedule based on predicted acute and/or chronic pain onset to ensure a pain free existence of the subject. This scheduling function can be configured such that scheduled appoints can be made directly to a computing device of the subject, without need for subject intervention in the process, essentially the process, e.g., including treatment notifications, can take place automatically. Once a new treatment has been administered and pain subsided, the pain characteristics can be tagged and used to update the system configurations, and the system monitoring and tracking may be reset, until the next pain episode is experienced.

In a manner such as this, given a clear mapping of the nerve tissues in the pain area, as well as an extensive characterization of the pain profile for the subject, the subject's experience of pain can be managed by generating a regular treatment schedule for each subject receiving treatments by the system. Specifically, the system can determine the extent of amelioration of pain for a subject due to treatments, and dynamically generate a treatment schedule to ensure pain reduction, such as where the physiological characteristics of the conductance of the nerve fibers is used to determine the subject's pain profile, e.g., based on conductance wave characteristics, such as duration, frequency, wavelength, amplitude, and the like. For instance, it has been determined that subjecting the subject to multiple treatments potentiates the nerve system thereby making subsequent treatments more effective, longer lasting, with less intensity needing to be applied. However, too much stimulation within too short a time period can lead to nerve fatigue.

Accordingly, another use for the wearable tMS sensing device is to determine approaching nerve fatigue when receiving therapeutic magnetic stimulation, so as to maximize the amount of treatment capable of being received by the subject, such as during a prolonged treatment session. Particularly, in various instances, a range of treatment conditions may be provided, such as to achieve a plurality of treatment objectives. For instance, the applied magnetic pulse to be delivered may be in a range between about 0.1 Hz or 0.5 Hz or 1 Hz to about 8 Hz or 9 HZ or about 10 Hz, such as for about 0-5 minutes to about 20 minutes, such as from about 10 minutes to about 15 minutes, and iterations in between.

More particularly, the treatment parameters may be determined by an iterative process of applying a low frequency magnetic pulse, configured to elicit a general response for a large number of people, such as at 0.5 Hz, and then upping the frequency to about 1, 2, 3, 4, 4.5, 5 or more Hz, and the like. This process can be done manually by a technician and/or other system operator, or may be performed autonomously by a system controller and/or by being informed by a system predictive, AI, analysis.

Likewise, the time period during which the treatments are to be applied may also be determined iteratively such as beginning from about 1 min to about 20 min or more, such as where treatments may start at a minimum amount of time, prior to evoking fatigue, but then increase with time, and eventually decrease due to potentiation, whereby a lesser amount of application intensity can be applied for a lesser amount of time, but with a greater amount and/or duration of pain relief. Age of the recipient of treatments may also be accounted for, such as where the younger the subject the more the applied time and the higher the frequency and/or amplitude may be set.

In a manner such as this, a real-time dose optimization regime can be implemented, and facilitated by the predictive analyses performed by the AI system. As indicated, this can be determined in a number of ways, such as by the amplitude of the conductance within the nerve, as well as the nature of the magnetic wave form being produced by the applicator to be applied to the subject, such as for the treatment thereof. Particularly, the intensity of the pain being experienced by the subject can be determined, in part, by the wave form of the conductance, such as with regard to its amplitude, wavelength, frequency, duration and the like, e.g., where an increase or decrease represents an increase or decrease in pain experience (dependent on the nerve fiber), which may trend over time. And likewise, the application of a magnetic field to the subject may be generated and provided whereby the wave characteristics of the magnetic field applied may be indicative of the extent of treatment necessary to effectuate an amelioration of pain over time, such as where a downwards trend, e.g., in amplitude, wavelength, frequency, and the like, is indicative of the health of the subject increasing, or at least their responsiveness to the treatments is increasing.

These activities may be conducted system wide for a large number of subjects, and a pain characterization and tolerance database may be generated, so as to better train the system to be responsive to the needs of the subjects using the system for treatments, thus making the predictive function more accurate, such as with respect to reducing or diminishing pain flare ups. Hence, the system is configured for determining an upwards or downwards trend, e.g., in pain experience and/or treatment efficacy, measure the trend, and adequately predict the effective treatment parameters of the magnetic field to be administered, such as in view of past administrations to the same or similar subjects, with the same or similar pain characteristics. The extent of the change in characteristics, e.g., amplitude, frequency, duration, and the like, can be determined and measured, and used to adjust system parameters, such as with respect to the frequency of treatments, their duration, and the intensity of treatments, and the like. Thus, the subject's adoption and/or adjustment to the treatments can be accounted for, and subsequent treatments can be personalized to the subject, accounting for their subjective experience of pain, and/or their adjustments to the treatments.

In view of the above, in certain instances, the tMS sensor devices of the system may be configured to record one or more sensed readings from the sensor modules, recognize patterns therefrom, and store the result in the memory so that it may be determined if one or more characteristics of the wearer is within or outside of a determined normal range. Particularly, in various instances, where a biological or other sensor is included, the sensor may be positioned close to the skin, such as positioned proximate a target area having one or more target structures therein to be treated and/or monitored. In such an instance, the sensor and/or imaging unit may be positioned behind a window area so as to maintain the waterproof patency of the device while at the same time allowing the sensor unit to perform one or more sensing operations. More particularly, in various instances, the processor module may work together with the sensor module to perform one or more analysis on the sensed data, either at substantially real time, or by retrieving the sensed data from the memory.

In such instances, as described herein below, the computing, e.g., AI, system may include one or more processing engines that can be configured to perform a regular analysis of the sensed and/or stored data to determine one or more baselines of one or more conditions of the wearer, and once established can periodically assess sensed data, e.g., presently sensed data, to determine if one or more of the wearer's conditions experiences a change. For instance, in some embodiments, the processor module may determine a baseline of routine activity, may identify a biological and/or physical pattern, and/or may establish a typical range of characteristics, and once determined the system can monitor these various parameters and assess the general health of the wearer and/or notify the wearer when a pattern has been interrupted and in such instances, warn the user to either cease engagement in an activity or to prepare to assume various consequences thereof.

For example, where the wearer of the sensing module has received one or more pain reducing treatments, the system may track their physiological conditions to determine when the pain treatment is wearing off and warn against engaging in various activities suspected of being likely to cause pain, and/or may notify the user, e.g., via a suitably configured downloadable application running on a mobile device, of the upcoming expected need for re-treatment. Specifically, in one implementation, a wearer's heart rate, blood pressure, body temperature (e.g., at the target area), and/or other monitored condition can be monitored and tracked, and this information can be coupled with the wearers experience of pain at the target site, such as entered at an interface on the client application, so as to determine the wearer's physiological conditions both with and without pain, and can then be used to predict when pain levels are moving from a non-pained or minimally pained state to a pained state where treatment is needed again.

Likewise, the experience of pain can be back-tracked to the activity causing the pain, such as via entering the pain threshold and the activity into the application, which may then be associated with sensed movement data so as to correspond the activity of the wearer of the device with pain causing activity and thus be able to warn the wearer that when engaging in a determined activity known to cause pain that if the activity is continued there is a likelihood of pain resulting. If such a condition change is experienced this may be transmitted and/or otherwise communicated or signaled to the system controller.

All of this information may be collected and used as data points for predictive or other modeling. As explained in greater detail herein below, these procedures can be implemented by a suitably configured Artificial Intelligence module including a machine learning and prediction unit running a predictive logic function, e.g., running a phase-locked loop. Specifically, as indicated, in certain instances, the various devices and systems, as well as their methods of use, as disclosed herein, may be employed so as to collect and evaluate sensed data, e.g., sensed nerve activity data, as well as reported pain experience data, e.g., from the subject in need of treatment.

These data points may then be used to generate location and orientation data, such as with regard to identifying a target nerve to be treated and cancelling out noise from surrounding, non-target nerves. Such data may also be employed to determine a predicted position and orientation of the tMS application device that may then be used so as to optimize an effective and efficient targeting of the pain causing nerve. Specifically, using the various data collected from the various sensor elements, and analyzed by the various computing devices of the system, one or more administration protocols can be generated and employed so as to deliver a magnetic impulse that is finely catered so as to achieve a maximal response of the nerve to be targeted, such as for the purpose of accomplishing one or more determined objectives, such as pain reduction and/or cessation.

Accordingly, such collected data, e.g., sensor data, can be classified, analyzed with respect to one or more captured characteristics, tagged, and stored, such as in a structured database containing one or more libraries. This evaluated and analyzed data may then be used to generate one more predictions, such as a prediction about an optimized configuration of the system as well as its methodology of use. For instance, the system may be configured for making a first prediction, about a first aspect of the system, and based on how well the actual results of this first prediction match the predicted results, the system may make a series of further predictions, so as to optimize the system configurations. Hence, a first prediction may be directed to identifying a target nerve fiber to be treated; a second prediction may be directed to identifying non-target nerve cells that may be proximate the target nerve, and therefore, creating noise; a third prediction may then be made as to what position and/or orientation the tMS applicator should be in in relation to the identified target nerve so as to produce an optimized response thereby, and then a further prediction may be made as to what parameters should characterize the stimulatory pulse to be delivered from the tMS applicator device to the target A-β nerve.

Once the AI module of the system has made a first set of predictions, so as to generate one or more first application protocols, the one or more protocols can be initiated, as described above. The one or more of the first set of predictions can then be tested against the actual results achieved by implementation of the initial protocol, and from these results a score may be given, e.g., with respect to the ability of one or more variables, e.g., amplitude, frequency, wavelength, etc. to effectuate the predicted outcome. Consequently, each variable may be given an initial weight, which initial weighting can then be used to better determine the optimal parameters by which to configure the system so as to achieve one or more determined objectives, such as increased pain reduction over increased periods of time. This process can be iterated over a number of configurations and administrations until an optimal response is achieved, such as in a predicted manner.

Accordingly, the data to be collected may be used to define one or more variables with regard to dynamically treating the experience of neuropathic pain in an individual, such as caused by irregular or non-activity of an A-β nerve fiber. For instance, the variables to be defined may include an amplitude of the magnetic pulse and a frequency to be generated by the tMS application device, so as to, at first, define and map the nerve fiber resulting in pain, and then to treat for the experience of pain. Specifically, a first objective to be achieved may be identifying the A-β nerve the inactivity of which is causing pain, such as by failing to deactivate corresponding A-α, A-δ, and C fibers. A second objective may be to map out the A-β nerve fiber so as to define its spatial arrangement and/or morphology, such as along its length, and may further be to define one or more surrounding nerve fibers, such as A-α, A-δ, and C fibers.

Further variables to be defined may include locating the tMS application device in space, with respect to the target nerve position, as well as orientating the coils of the tMS applicator so as to better target the nerve to be treated. Additional variables include determining and optimizing the characteristics of the magnetic field being generated, e.g., with regard to voltage and current, and applied by the tMS applicator, which may include modulating the amplitude and energy of the magnetic pulse being generated, the voltage and/or current being pushed through the coils, and/or configuring the system to minimize resistance. In further instances, the length and duration of the pulses being applied may also be modulated so as to generate a characteristic response within the nerve fiber, such as with respect to creating an optimal depolarization within the target A-β nerve, for a prolonged period of time, without fatiguing the nerve.

Accordingly, in view of the above, one or more of the aforementioned parameters may be dynamically modulated and tested and/or modified throughout the mapping, targeting, and treating process, in an iterative process, as explained herein, so as to determine the optimal use parameters for the system. Hence, the system may be configured so as to determine and implement an optimal treatment protocol on a person by person basis, so as to administer more and more effective treatments for a person over time. The results may be achieved by better characterizing the pain experience, better defining the pain causing tissues, e.g., nerves, better administering treatments in terms of spatial positioning, and characteristics of the treatment waveforms. The system, therefore, is configured for better improving the quality of life of the persons receiving the treatments.

Likewise, these identified pain characteristics, as well as the optimal treatment parameters for the person being treated with their individualistic features, may be defined, classified, catalogued, tagged, and saved into one or more databases of the system. The system may then perform various analyses, as described herein, over a wide range of pain and/or subject characteristics, over a prolonged period of time, and with respective treatment protocols that have been or have not been effective for treating them. Further, their pain, such as with respect to similarities and dissimilarities between them can be defined and characterized.

In certain instances, a user of the pain treatment system may be a trained professional, a healthcare practitioner, or the subject to be treated themselves, or the like, who is responsible for controlling one or more components of the apparatus so as to ameliorate the experience of pain. Accordingly, in such instances, the overall system may evaluate collected data, generate a first protocol and a set of user instructions for implementing the first protocol, which instructions may walk the user, and/or instruct the system itself, so as to define the target site and/or administer the treatments to the target site.

The system may then administer a series of questions, such as in a dynamic and interactive interview process, by which the system can elicit from the treated subject their experience of the reduction in pain. The subject's subjective responses may then be processed, and a comparison may be made to a collection of other subjects having been treated for the same or similar experience of pain. The system may then generate one or more modifications to the treatment protocol based on the analysis performed, and may present a new protocol to the subject for continued treatments to better alleviate a pain condition.

Specifically, in generating a protocol for the treatment of pain, the system may select or otherwise generate a series of questions so as to elicit a characterization from the subject as to where their pain is located, how it is characterized, e.g., acute, sharp, and fast versus chronic, dull, and slow, etc., as well as how a previous round of treatments affected the alleviation of pain, such as compared to before and after administration or in comparison to other treatments received. Based on the user responses, one or more of the system configurations and/or treatment parameters may then be adjusted or tagged for further use in subsequent treatment administrations. These procedures may then be repeated one or more times until the optimal parameters for the subject have been identified and administered to the subject.

For instance, once the treatment data and the subject's subjective experience of pain and relief thereof has been collected, based on these results, various of the configurations and parameters can be weighted and re-weighted, based on the correspondence, determined by the system, of the device configurations, treatment parameters, and experience of the alleviation of pain. Hence, the system can collect data regarding the system and treatment configurations, can analyze them, determine which factors have contributed to pain alleviation, and which have not, and in response thereto, weighting and reweighting these factors when determining treatment configurations and protocols for future use with the present or future subjects.

Hence, these factors can be identified, analyzed, weighted, tagged, categorized, and stored in one or more libraries of a repository of the system, such as with respect to one or more defined categories and classifications based on the various characteristics of the treatments and administrations. In various instances, one or more of the parameters may be weighted and implemented based on one or more entered or otherwise determined objectives of the person treatment, such as extent of pain reduction, duration of pain reduction, quality of pain reduction, rapidity of pain reduction, and the like. The system may further track the subject responses over time and use them to personalize the treatments to the individual being treated.

The analysis, evaluating, and weighting may be based on one or more selected or system determined objectives, such as with respect to increasing pain reduction via the administration of a treatment protocol that accounts for identifying a target nerve fiber, an appropriate orientation of the tMS application device, and delivering a magnetic pulse having pre-selected waveform characteristics and delivery parameters, including the amplitude, frequency, duration, current, and voltage of the pulses being delivered so as to achieve a corresponding amelioration of pain. Consequently, various of these parameters may be causally connected to one another and may result in the formation of one or more distinguishable patterns, such as where an adjustment of one parameter leads to an increase or decrease in a corresponding sensation of pain. These connections and patterns may be directed to how the target nerve is being identified, how the tMS device is being orientated, and/or how the magnetic pulse is being generated and/or delivered.

The system, therefore, may determine and analyze this data, discern various patterns thereby, and develop one or more protocols, e.g., rules, or objectives therefrom, which rules may then be used to better effectuate treatment protocols and system configurations. Other rules, developed from identified patterns of various relationships between treatment configurations and pain amelioration, such as with respect to treatment protocols and device orientations, may also be determined and implemented, such as in evaluating and treating new subjects based on the parameters and settings employed when treating prior subjects. Hence, once one or more patterns have been determined by the system, specifically via a suitably configured AI module thereof, the pattern can be used to derive rules by which the treatments and tMS system can be configured to generate new treatment protocols and system arrangements, in a dynamic manner, which can be more tailored to target nerve fibers of a subject. Consequently, one or more actions may be taken by the system in view of the identified relationships and/or determined patterns so as to make the system more effective and efficient at reaching its determined objectives in a manner so as to alleviate the experience of pain.

For instance, once a relationship between the various treatment parameters and/or system configurations as well as the factors relating thereto have been determined, such as with respect to how best to identify and target a nerve fiber for treatment in a subject, a pattern with respect to how to best activate that nerve with a magnetic pulse with regard to evoking a reduction in pain experience, the system may take one or more actions, e.g., corrective measures, to generate a new, revised protocol that builds on the success of a previous protocol so as to make the system more efficient at treating pain without fatiguing the nerve. Accordingly, in view of the above, the system, e.g., an artificial intelligence module thereof, may be configured for performing one or more analyses on collected data, treatment protocols, system configurations, and the circumstances during which the treatments are to be delivered, and one or more patterns may be determined by which an optimal treatment protocol can be determined, an ideal system configuration can be determined, and the model wave pattern for the magnetic pulse can also be determined. Likewise, based on these analyses, the system may also be configured for evaluating the various results of the treatments, and given one or more of the other determined parameters, the AI of the system may recommend ideal treatment and/or system parameters that may be modified so as to achieve better predicted results.

Hence, once one or more patterns or trends have been established, a correlation between the treatment and its achieved objectives may be determined. High performing parameters, therefore, can then be scored, weighted, and stored for later use by the system in generating new protocols and configurations, as disclosed herein. The system may store the parameters and configurations that effectuate a maximal reduction in pain based on the subject's individual response to the treatments. Those parameters and configurations may be mapped to the resulting ameliorations and scored, and the identified patterns can then be used for developing new treatment parameters and configurations for each particular subject and/or a group of subjects. These patterns may be recognized and identified by the AI module of the system.

In particular instances, the AI module may include a pattern recognition or machine learning platform, as well as a predictions module, together which AI module may be configured to recognize patterns, analyze them, and determine rules, e.g., protocols, by which to re-orientate and/or calibrate the system and its treatment regimes. From these patterns, the machine learning and/or predictions module of the system may be employed to evaluate content, e.g., online content. One or more subject's particular pattern(s) of pain experience and response to treatment with respect to pain amelioration can be evaluated. And a pattern in relationship between the two may be determined, so as to then calculate the effectiveness and usefulness of the treatment protocols and system configurations.

Such evaluations may be performed for a number of different reasons, especially with respect to one or more determined objectives of a determined treatment regime. This process is useful in situations such as where a pattern of system parameters and/or configurations leading to a reduction of pain appears to coincide or conflict with the patterns of usage and pain reduction experienced by others, or for the same period across treatment administrations. Specifically, the system may be configured for determining the presence of various factors influencing a reduction in pain experience, e.g., in one or more persons receiving treatments.

In various instances, there may be a number of factors, such as factors pertaining to the identifying and targeting of nerve fibers, orientating the tMS application device with respect thereto, and pertaining to the configuring the tMS delivery parameters, as well as for determining which factors may be leading to and/or influencing a reduction in pain experience, and to what degree. Further, once these influencing factors have been determined, the system, e.g., via the suitably configured learning module, may then be adapted to produce rules or parameters that may be employed in generating a treatment protocol that capitalizes on such influences. For instance, a predictive intelligence module of the system may determine whether the influencing factors are such that in view of them a weighting scale may be increased or decreased, which weighting scale may be used to weight both the configurations of the system and the delivery parameters for delivering a treatment protocol.

Accordingly, in view of the above, when various patterns are formed, the system may learn these patterns, breakdown and learn the factors leading to the pattern so as to thereby determine the existence of, and the reason for, the presence of a trend, e.g., in pain reduction. Likewise, using this data the system may predict a likely manner in which pain reduction will occur, and a level of confidence may be given to the predicted factors leading to the predicted outcome, such as from 0.0, not very likely to 1.0 almost completely certain. Thus, when the system makes a correct prediction, e.g., that a given parameter will result in a certain percentage decrease in achievement toward an objective, such as pain reduction, the connection between the initiating action, e.g., treatment initiation, and the resulting action, e.g., pain reduction, can be strengthened.

For instance, a first initiating event may be the identification of a target nerve fiber, e.g., with respect to one or more locations. Further, a second initiating event may be the generation and/or delivery of a treatment protocol, where the treatment protocol includes elements known to positively influence pain experience, e.g., factors affecting a reduction in pain. A prediction may then be made by the AI of the system as to the successfulness of proposed pain treatments. This prediction may be based on the strength, e.g., weighting, of the relationships between the various administration and/or system configuration factors. So being, when a prediction is made, with regard to one or more initiating events, and the final outcome occurs, e.g., pain is reduced, the various connections that had led to the successful outcome may be strengthened.

In such an instance, when these same or similar conditions occur again, for one or more subjects, the system will be quicker to from predictions and based on those predictions generate and administer treatment protocols, with a higher prediction of their effectiveness. However, if the expected predictive event, e.g., pain decrease, is not achieved, the system will then access the various weighted factors to determine why the model did not work, and corrections and/or recalibrations to the system and/or its component parts will be made so that a new predictive model can be developed. Hence, in a manner such as this, when factors are identified as having a positive predictive correlation to one another, they may be deemed to be connected, and the strength of that connection can be increased.

Further, the more the two factors occur together, such as where a given protocol or configuration results in a decrease in pain experience, the weighting of that association can be further increased. Where the predictive model does not or ceases to work, the system may analyze the various factors and/or metrics, draw new connections, and re-weight the various defined connections so as to come up with a new predictive model. The new predictive model may then be used to generate a new treatment protocol or system configuration, with the expectation of increasing the objective outcome, e.g., pain reduction, and the like. Hence, when a pattern is observed, and the predicted result occurs, the weight between the various elements in the predictive chain may be increased, making it more likely for this pattern to be propagated again and again.

However, when a pattern is observed, and the predicted results do not occur, the weight between the various elements in the predictive chain may be decreased and/or reorganized until a new pattern is performed. These predictive analyses are especially useful in determining the treatment protocols and system configurations that are to be weighted, scored, and used for generating new protocols and configurations. Particularly, the system can be calibrated such that a universal treatment protocol and/or system configuration can be developed and used as an initial model, e.g., based on a sample set of previously treated subjects, which model can then be adapted, in an iterative and dynamic fashion, to each particular, individual subject.

Accordingly, the connection between the action and a predicted outcome of that action may be evaluated, such as by giving an estimation of a successful predicted outcome, e.g., a successful pain treatment, and the like. When that estimation is proved out, the predictive model may be strengthened, such as for future implementation. However, when the estimation is not proved out, the connection may be weakened.

Particularly, predicted outcomes for treatment success may be made based on the totality of the variables being considered, such as where the same or similar protocols are being proposed to be used in a plurality of the same or substantially similar circumstances, e.g., pain experiences across subjects. Thus, when a previous pattern is repeated, in the same or different treatment subjects, the various variables identified by the system as leading to the pattern, and the connections between them, may be given more weight. Likewise, when a pattern is broken, less weight may be given to the various connections between the initiating action, e.g., the amelioration of pain, and various factors leading to the occurrence of non-predicted outcome. A new weighting and organization of the elements of the treatment protocol and/or system configuration may then take place until a new positive pattern is re-established. Changes in patterns can also be aggregated along various dimensions to group a plurality of treatment protocols for a variety of subjects, which groupings may be used to more precisely define and weight patterns of treatment based on their collective response to treatments.

In a manner such as this, the system may be configured to keep track of the various treatment protocols, relevant factors, and configurations with respect thereto, as well as the characteristics of the subjects being treated. Thus, the various identifiable factors that may be influencing the emergence and/or maintenance of such patterns, with respect to pain alleviation, may be identified, predicted, and employed for a plurality of different uses, such as for dynamically selecting and employing universal and/or individual treatment protocols and configurations.

For instance, the system may be configured for generating an interview to be presented to a user who is in need of treatment. In such an instance, a series of questions may be generated and/or selected from a database of questions, which questions may be provided so as to produce answers that can be used to build a profile of the individual and their pain experience. Accordingly, in response to the presented questions, a series of replies may be received, and a search of one or more data structures may be made so as to characterize that particular individual's pain experience. A first prediction as to what may be causing that pain for that individual may be generated, such as where the characterization is based at least in part on a comparison of the individual to other subjects having experienced pain with the same or similar characteristics or circumstances.

Likewise, a first treatment protocol and a first prediction of successfulness can be generated, e.g., based on a comparison of what worked for others, and a first series of treatments may be made, based on the first treatment protocol. The results thereof, as reported by the treated individual, may then be analyzed by the system, and one or more new protocols can be generated and one or more new predictions of successfulness may be made. In various instances, the system may be configured for tracking effectiveness of the treatments, and for taking corrective actions, such as by modulating one or more system parameters so as to better achieve the cessation of pain.

For instance, a change in one or more parameters that leads to a reduction of pain can be given an increased score, and therefore, may be given a greater weight. Thus, the identified parameters may be used in a further treatment protocol to be administered to the individual to be treated. This process can be repeated until all of the relevant parameters affecting the experience of pain have been defined, and once defined, new protocols can be initiated so as to optimize these defined parameters. In this manner, all parameters can be characterized and individually evaluated, and those that work well can be given greater scores and weight, whereas those that do not do well can be given lesser scores and weights.

Specifically, the system may generate and employ one or more data structures that may be queried so as to predict the answer to one or more questions. For instance, as described in detail herein, the system may be configured for receiving information with regard to an individual's experience of pain, including descriptions about the personal characteristics of the individual, their morphology, and their pain experience. Additionally, the system may populate the data structure with a selection of others who share similar conditions and/or experiences, and who have been treated, whereby the treatments may have been successful or not successful.

Each of these data may serve as nodes in the data structure, and the system may then analyze the data so as to determine correspondences between the needs and thereby determine one or more relationships between the nodes. The system may then weight common connections between the nodes, strengthen those relationships that lead to the successful amelioration of pain, such as by giving them an increased weight, and those relationships that do not lead to a decrease in pain can be given less or even negative weight. In a manner such as this, those factors, as described herein above, can be identified, and those factors leading to pain decrease can be defined, weighted, and scored. This scoring can then be used to generate a treatment protocol for any particular individual seeking treatment.

According, all of this information may form data points that characterize any given subject, their experience of pain, and the successful treatment of them by the system. These data points may then be employed as nodes within a data structure, which data structure may take any suitable form, such as a data tree and/or a knowledge graph, and the like. From these various data points, e.g., nodes, relationships between nodes characterizing pain, and nodes characterizing the system configurations and protocols that have led to the amelioration of pain, may be identified. These connections between the identified data points may be weighted based on the number and form of the interactions between them, and the various factors defined and actions taken by the system to alleviate pain may also be weighted.

Hence, the more a system configuration and/or treatment protocol leads to a lessening of pain for one or more individuals, e.g., in a positive manner, the greater the weighting will be between the various nodes that may be employed to define these relationships and interactions leading to pain reduction. Likewise, the more negatively a protocol and/or system configuration leads to a reduction in pain, the less (or more negative) weight will be given to define these interactions. Likewise, in various instances, the system may make a prediction as to an outcome that actually occurs. In other instances, the predicted outcome does not occur, in such instances, more or less weight will be given to the relevant factors and configurations when predicting outcomes for future events, based on the successful prediction of outcomes of past events.

Accordingly, data points between the various nodes of a structured database of the system may be used to generate correlations between the nodes and to weight those correlations so as to build a data structure thereby, such as a knowledge graph or tree. The data structure may then be queried to determine other relationships not previously known. These new data points may be mined to predict the influence of external factors affecting the usage of the system, may be used in generating treatment protocols, and may further be used to select optimal system configurations, all of which can be tested. The results of this testing may be used to predict and weight potential outcomes of new treatment regimes, such as based on a collective of usage patterns of how others may have responded to the same or similar treatment regimes, such as when the individuals have the same or similar characteristics and/or experiences of pain.

For instance, a data structure, such as a knowledge graph, may be generated. Particularly, a knowledge graph may be generated by the system receiving known data about the various individuals to be treated, e.g., characterizing the conditions of the subject and the characteristics of their pain, and further receiving known data about various treatment protocols and system configurations that have been implemented to treat these and other subjects successfully. Each of these entities may form nodes in the knowledge graph, and the interactions between the nodes, one with the other, may be mapped and scored. Where the interaction is positive, a positive score may be given for that interaction, and the same for the negative.

In a manner such as this, the system may be configured for building stars of data points that together form a constellation of relations. These relations are defined by a multiplicity of interactions that form webs between known pain characterizations as well as the protocols and system configurations that have been successfully employed to relieve that experience of pain. These knowledge graphs, the various data points they represent, and the relationships between them, may be used by the system to dynamically generate a treatment protocol and system configuration for treating each individual in a manner so as to decrease the experience of pain.

The number of relationships between the various data points as well as the strength of those correlations may then be determined and used to weight the known or fact based relationships. Likewise, from these known fact based relationships, previously unknown, inferred relationships may be determined, and weighted. In a manner such as this, the knowledge graph, or other data structure, may be generated so as to include both known and unknown, inferred, relationships. These known relationships may then be leveraged to identify treatment protocols and system configurations that may be useful for treating for an individual's experience of pain.

Accordingly, once generated, the knowledge graph may then be queried along a number of lines so as to make one or more determinations with respect to the various relationships between the various nodes of the graph. In such an instance, the system may leverage the identified connections so as to predict what actions may be taken to strengthen or decrease those relationships. Essentially, in one implementation, the system can be configured to determine the relationship between an individual's experience of pain and the protocol and system configurations that are successfully used to treat that pain. From the strength of that relationship between these two factors, a score may be given so as to weight the possibility that the protocols and system configurations used to successfully treat that subject may be employed again to treat that same subject, e.g., at a later time, and/or other subjects having the same or similar characteristics and/or pain experiences.

Accordingly, in various embodiments, the system may be configured so as to be queried along a number of different parameters to determine and weight a number of different metrics and/or answers, and thereby make a variety of different predictions. These predictions may then be given a weighted score, such as to the probability of being correct. Based on that score, the system can generate a treatment protocol and/or orientation of the tMS applicator as well as pulse characteristics so as to administer treatments to a target nerve and properly account and/or correct for the predicted responses.

In a typical architecture for performing such functions, such as for generating a treatment protocol, e.g., for applying magnetic pulses for the alleviation of pain, the system may include a database of relevant protocol and/or magnetic pulse features. For instance, one or more databases may be queried or searched for commonalities between: subject conditions, pain characteristics, as well as treatment protocols and system configurations that have successfully been employed so as to treat those pain conditions in the past. The system may also identify and/or pinpoint pattern data, as well as predictive outcome data of the past, present, and/or future, so as to narrow the search query and identify other characteristic data the system determines is relevant to the particular question being asked and searched. In such an instance, the relevant data points may be identified and pulled from a general repository or dedicated database, and a localized data structure may be built.

Any data structure may be constructed and employed for performing the search in question. In various instances, however, the data structure may be a relational data structure, such as a Structured Query Language (SQL) database, which may be implemented via a relational database management system. For instance, in one implementation, the SQL database may be a table based data structure, such as where one or more tables form the base structure wherein data, such as media content, may be stored, searched, relations determined, and queries run and answered in a structured manner. Particularly, in various embodiments, a table based database may be presented, searched, and used to determine relationships from which answers to one or more queries may be determined.

Typically, in such a data structure, identifiers, such as keys, are used to relate data in one table to that in another table. For example, typically, SQL databases have a relational architecture. These constructions may be represented by a table structure. A series of tables or a word graph, for instance, may then be employed by which correlations may be made in an iterative fashion to identify parameters and/or metrics that may be of particular use in building an appropriate treatment protocol and/or system configuration.

Specifically, with respect to whether a certain subject being treated is positively or negatively engaging with a selected treatment protocol and/or system configuration, such as with regard to a particular orientation and device setting, a first correlation may be made between the subject's normal (past) experience of pain, and/or a typical response to treatment, and their current experience and response given a change in protocol and/or configuration. For instance, a first correlation may determine the nature of a subject's response to a pain remediation protocol. This may be reviewed for a period of past treatments and protocols, and may be determined over a series of days, weeks, or months, such as to determine a baseline for how well the subject responds to treatments and the extent to which interactions are consistent over time.

The results of these comparisons and analyses may be compared to subsequent treatments for the subject, and/or how others responded, when treated in like manner. In such a manner, the present subject can be compared against the mean or average of the subject's past responses, and/or the mean or average of the response of others, who have been treated in like manner. This data may then be broken down and a first table, or other data structure, may be formed to record this data as a first use model sample set.

Subsequently, a second table, or other data structure, may be built whereby the subject being treated, or a group of subjects having been treated, under varying protocols, configurations, and/or system parameters, may be tracked and compared against the subject themselves or a collective. The two data structures can be compared with one another so as to determine if the subject's present interactions and experiences comport with their, or other's, past interactions, and/or how their present experience comports against the collective of relevant other subjects. Where it is determined that a user's present response is outside of what would be their historical or predicted usage average, the system can flag the interaction as worthy of a deeper dive.

If necessary the system can then mine the data structure and can begin to look for other correlations between a present subject and their response to treatments, so as to determine possible explanations as to why this user's present interactions are outside of their predicted behavior, which may be for the better or for the worse. Specifically, where the data structure is a series of tables, the user's identifier may be searched and compared through a number of tables for a wide variety of correlations that may be determinative in explaining their present experience with a given treatment regime. Where a source of positive or negative interaction is determined to be present, the system can implement a corrective regime to enhance or correct for that experience.

Accordingly, a key may be used to correlate the tables, or other data structures, which key may be accessed in response to a question, prompt, or command, such as why the user's present response does not comport with their past response. The key may be any common identifier, such as a name, a number, e.g., a RFID number, cellular identification number, a phone number, and the like, by which one or more of the tables, or other data structures, may be accessed, correlated, and/or a question answered. Accordingly, without the key it becomes more difficult to build correlations between the information in one table with that of another. In certain instances, a table may be a hash table and a hash function may be employed in search the table for correlations with other data structures.

As indicated, a further architecture that may be used to structure a database is a data tree, e.g., a suffix or prefix tree, where various data elements may be stored in a compressed, but in correlated fashion, where the various roots and branches form divergent data points with respect to potential correlations. In other instances, a graph based architecture may be structured and used to determine the results for one or more queries. Particularly, a knowledge graph architecture may be employed to structure the media repository, so as to enhance the performance of computational analyses executed using that database. Such analyses may be employed so as to determine whether a given patient's present activities and their responses to treatment comports with their past activities and responses to pain treatments. Accordingly, the sophisticated algorithms employed herein, are adapted for structuring the infrastructure of a relational database so as to enable more efficient and accurate searching, such as for identifying and evaluating and scoring successful treatment protocols and system configurations, which data can then be collected, graphed, and predictions may be derived therefrom, such as via performing graph based analyses, as well as for performing table or tree based analyses.

Consequently, in one aspect, a device, system, and method of using the same to build a searchable, relational data structure, such as described herein, is provided. Particularly, in one instance, the devices, systems, and methods disclosed herein may be employed so as to generate and/or otherwise collect data, such as treatment and system configuration data pertaining to how one or more subjects respond to treatments over time. This data may then be used in developing treatment protocols that may more effectively characterize and then relieve an experience of pain for one or a group of subjects, such as within a same or similar demographic.

Accordingly, in one embodiment, methods for building and structuring a searchable database are provided. For instance, in a first step, data, e.g., factors and parameters used in applying and/or responding to a treatment, may be identified, scored, collected, scored again, e.g., at a later time, cleaned, weighted, and then be prepared for analysis. In various embodiments, the data may be labeled and/or categorized, and may then be structured into a searchable data architecture, such as a knowledge graph, table, or tree-like structure. And once the database is structured, it may then be populated with data, e.g., treatment protocols and responses thereto, as well as the conditions leading to the same, in accordance with the determined or inferred relationships. Such relationships may be notional, fact, or effect based.

More particularly, in certain instances, a machine learning protocol, as disclosed herein, may be employed so as to determine relationships between data points, e.g., related to treatment protocols as well as those who responded favorable to those protocols, which may be entered into the database. Such relationships may be determined based on known facts, and as such the learning may be supervised learning, e.g., such as where known factors may be used to label, categorize, and store data, such as pain experience and location, interaction, device orientation, magnetic pulse configuration, responses to treatments, and the relationships pertaining thereto, and other related data.

In other instances, the learning may be inferred, such as in an unsupervised learning. For instance, in certain instances, the data to be stored may not be known, relationships between the data may not have been pre-determined, and the query to be answered may also not have been otherwise identified. In such instances, the data to be stored is unsupervised, and as such, patterns in data to be stored and their relationships, such as commonalities between data points, may be determined notionally, and once determined such patterns may then be used in forming the architecture that structures the searchable data architecture.

For example, where an individual's response to the administrations by the system, e.g., their decrease in pain experience when undergoing treatments, breaks a pattern, either positively or negatively, the system may explore relational characteristics of the individual and/or his or her response to pain treatment so as to determine what pattern was broken and/or to assure its maintenance or correct for its effects, or to simply determine a new pattern of response is emerging, in which instance, a deeper exploration may not be warranted. For example, a known sequence of patterns may be used to infer that if events A and B in a known sequence may be followed by event C such that if event C does not happen as predicted, a flag is set off for initiating a deeper exploration of the nature of the causes of the flagged event. However, where upon a first round of exploration, it is discovered a new pattern of behavior is being established, the flag may be removed and a deeper exploration as to the causes of the new pattern formation can be but need not be explored.

As described above, in certain instances, at the heart of the platform, therefore, may be a generated data structure, e.g., a graph based database architecture. The data structure to be generated may be constructed on the fly by the APIs and/or skimmers of the system retrieving data points from a plurality of sources, and populating those data points into a suitable data structure from which relationships and/or correlations between the data points may be made. This is particularly useful when determining consumer response individually or en masse to an advertising campaign of one or more companies.

First, when populating the data structure, known facts, e.g., system settings and condition parameters, and/or responses thereto, may be populated. Then known relationships may be determined. From these known facts and known relationships, otherwise unknown facts and/or relationships, e.g., how an individual will respond to a change in one or more parameters, may then be determined.

In such a manner as this, the treatment parameters employed, the wave pulse characteristics, the orientation of the applicator with respect to a proposed target site, and the reported responses to the mapping procedure, e.g., with regard to which triangulation and/or trilateration sets provoke the greatest responses to pain alleviation may be leveraged and used as data points in the construction of a data structure, such as a knowledge graph. From this data structure, correlations and relationships may be determined, for instance, between a single subject over time or between a collection of subjects, for example, by determining how these various factors interact with one another, with respect to leading to a reduction in pain.

The type, quality, and/or quantity of these relationships may then be determined by the system. Pain reduction (and/or other metrics) may be evaluated in terms of quantifying a reduction in pain quality, as compared to a wide selection of system configurations, and the results may be employed so as to determine a predicted outcome, such as in response to a given query. For instance, the data structure may be queried for the purpose of determining the potential that a change in one or more parameters will result in a change, e.g., a reduction, in pain quantity, quality, and/or experience.

Once the data structure is built, and the known and inferred facts and relationships determined and/or weighted, the data structure may then be queried, such as with respect to identifying system parameters that are useful for building one or more treatment regimes and/or system configurations of the system. Specifically, the system may be directed, such as by a system operator or treatment subject, as to what the query is or should be, such as from a list of known query types. Such a directed query may be implemented so as to perform a supervised search query. Alternatively, the system itself may generate a query automatically, such as when it identifies certain patterns that are worthy of greater explanation, and as such an unsupervised query may also be instigated.

More specifically, the various data points entered into the data structure may be labeled and categorized. Such categorizations may be based on known identities and patterns between them, and may characterized identified metrics and/or parameters. One or more filters may be applied, and a given search query may be performed with respect to the identified labels and categories. Particularly, a first query may be run such as where the outcome, e.g., a known relationship, has previously been determined to be important to the performance of one or more objectives of a user of the system and/or person being treated. This is useful when the system is being primed and/or has already been primed in such a manner that it knows what it is looking for.

In other instances, the predictive AI module may itself identify patterns, commonalities, and/or other elements that form a previously unknown relationship, from which one or more labels and/or categories may be generated automatically by the system itself. The system may then run a query that can be performed based on system generated prompting with respect to these unsupervised factors. This is useful when it is not necessarily known what is being looked for, such as when initiating an initial mapping routine so as to identify the nerve to be targeted.

In particular, in various instances, a machine leaning module may be provided, such as where the machine learning module, as described herein, may be adapted to recognize how an output, a given response to treatment, was achieved based on the type and characteristics of the inputs received, e.g., the treatments administered. Specifically, in various instances, the present system may be configured to learn from the inputs it receives, the relationships it determines, and the results it outputs, so as to learn to draw correlations more rapidly and accurately based on the initial input of data received and/or the types, quality, and quantitates of the relationships it is able to correlate.

Likewise, once the AI machine learns the behavior, e.g., of one or more subjects being treated, the learned behavior may then be applied to a second type of data, e.g., unknown data, such as via a provided inference engine. For instance, an inference engine may be used to infer various relationships and/or to predict the answer to one or more unknown variables, or heretofore unknown relationships, based on previously determined and known relationships. Specifically, from known data and relationships, such as between pain amelioration and system setting parameters, the inference engine may make a prediction as to how to change in one or more system parameters will affect a change in pain reduction. These predictive data may then be used to select one or more system parameters that may be employed to optimize pain reduction while minimizing nerve fatigue and/or system overheating.

There are several different types of relationships that can be determined. For instance, relationships may be determined based on what is known, e.g., they are fact based, and/or they may be determined based on the known effects of those facts, e.g., they are effect based, e.g., logic based. In various instances, these relationships may be determined based on inferences, e.g., relationships, that are unknown but determinable. Specifically, a relationship between two treatment administrations and/or between two subjects, pain experiences, interactions, and/or other relevant conditions of one or more system parameters, may be inferred based on various common facts and/or effects observed between them.

As described in great detail herein, these previously unknown but inferred facts and/or relationships may be determined and/or used in predictive models by generating a data structure as disclosed herein. Other known, e.g., fact, effect based, or inferred data points may also be generated, or otherwise entered into the system. These data points may then be used to generate one or more nodes, e.g. a constellation of nodes, which may subsequently be used in the determination and/or weighting of the various relationships between the data points.

Particularly, the various data points of a data structure may be characterized in a plurality of different manners, such as with respect to being a subject, a predicate, and an object. More particularly, each node and the relationship between the various nodes will have properties by which they can be placed into one of these three categories based on a given query to be answered. Hence, as the nodes are populated, they are also populated with one or more characteristic properties that more fully define and/or classify that node.

Known facts, as well as their known properties, are first employed by the machine learning module (ML) to determine known outcomes, during which process the ML module thereby learns the patterns of behavior between the nodes and their relationships to one another, such as in a training process. This training may take place over a wide range of sample sets, e.g., for a given subject or across multiple subjects, until an acceptable accuracy has been established. Once appropriately trained, e.g., via a deep learning protocol, then the ML module, may be given data points from which unknown relationships need to be determined, and unknown outcomes predicted.

Specifically, once the ML module has learned the expected patterns of relationships, e.g., behaviors, with respect to known data points and relationships, it may then develop "inferred" rules by which it may classify and label new or unknown data points. These rules and known data points and relationships may then be correlated so as to determine and account for otherwise unknown relationships. In a manner such as this heretofore unknown data points, their properties, and relationships between them, may be classified, labeled, and/or otherwise defined. In such an instance, when expected results are achieved, such as with respect to a predicted experience of pain amelioration occurring given a determined system configuration, the system status quo may be maintained. However, when these new data points evoke a breakdown in patterns of relationships and/or expected outcomes, e.g., a subject reacts in an unexpected way or an unexpected result occurs, then a system alert may be triggered and a deeper exploration may be initiated.

Additionally, once the knowledge graph architecture has been constructed, the AI module may employ that knowledge graph to answer one or more queries of the system, such as to where treatments should be applied and what system parameters should be employed, and/or to make one or more predictions with respect thereto. For instance, the AI module may configure the data structure, and implement one or more functions with respect thereto, such as via one or more known or previously unknown facts, e.g., via the machine learning protocols disclosed herein, and thereby predict various consequences with respect thereto.

Further, once the data structure is generated, it can continually be updated and grown by adding more and more pertinent data into the knowledge structure. Such data may be collected or otherwise from any relevant source of information pertaining to the subject(s) being treated, and may be used so as to build more and more potential nodes and/or relationships. In various embodiments, the system may be configured for being accessible by system users, and/or other third parties having the appropriate access permissions. In such an instance, the user may access the AI prediction module, e.g., via a suitably configured user interface, upload pertinent information into the system, and/or determine the relevant nodes by which to answer an inquiry, e.g., such as what is predicted to result in the experience of pain in a subject if X, Y, and Z system parameters are changed, and/or does their behavior with respect thereto fit within an established and/or otherwise expected pattern of behavior.

The ML and AI predictive modules of the system have many potential uses. In certain embodiments, the system may be configured for collecting online content that can be evaluated and stored within the system and used to generate a treatment protocol that may then be administered to one or more target recipients. As such, the system may be configured for providing a platform by which a system user, e.g., a subject to be treated, may be enabled to more closely administer treatments, monitor treatments, and more effectively modulate treatment parameters that can be controlled from a single user interface, such as at a desktop or mobile computing device interface.

Specifically, in one embodiment, a downloadable application is provided, which downloadable application provides a graphical user interface (GUI) through which interface the user, e.g., subject to be treated, may more intimately involve themselves in administering treatments. More specifically, the GUI may be configured to present a dashboard to the display of the computing device, through which display the user may be enabled to interact in the treatment of pain in a more meaningful way. For instance, in one instance, the dashboard may present a display such as for displaying a series of menus by which a user of the system may configure the system and select an administration protocol, such as based on recommendations and prompting by the system, which can immediately be implemented for effectuating treatment administration.

In such a manner as this, a real-time treatment administration protocol may be generated, e.g., autonomously, by the system or may be selected, recommended, and/or approved by the system, or a user of the system. Likewise, based on a subject's response to the treatments, dynamic and real-time modulations to the targeting, orienting, and system use parameters can be made so as to better tailor the treatments to the ever changing needs and experiences of the subject being treated. These system modifications can be implemented automatically or merely by the touch of an engagement button. In various instances, the user may select from a variety of treatment protocols and system configurations that may be generated by the system and presented to a user, e.g., subject to be treated, for their selection via a dashboard display, such as via a downloadable application or "app", such as a mobile client application running on a client computing device, such as a mobile phone or handheld computing device. The dashboard may also provide a platform through which other system users, such as a treating professional, can monitor and/or approve selected treatment parameters in view of the subject's response to present or past treatments.

Accordingly, as described above, the machine learning module may be employed so as to generate a profile of the subjects being treated, the protocols and system parameters being employed to treat them, as well as their response to such treatments. The profile may be a list of properties, qualities, and/or characteristics that describe the subject to be treated, their conditions, e.g., pain experience, as well as the treatment parameters that were previously used to treat them along with their responses to those treatments. As such, the profile may be generated by a plurality of different methods, such as by providing an interview to the user and saving their responses, further characteristics may be determined based on their engagement with the system, such as by tracking, characterizing, categorizing, and saving the treatment protocols used to treat them as well their responses thereto.

Further characteristics may be determined based on how a selected group, having the same or similar conditions and/or experiences, have previously responded to treatments either individually or collectively, or some sub-portion thereof. All of this data may then be collected for the various users of the system, such as to generate a global pool of data that can then be used to generate a knowledge graph that may be analyzed with respect to determining commonalities and relationships there between so as to better determine one or more treatment protocols for individual subjects preparing to undergo treatment. Specifically, in various instances, once these characteristics have been determined, the AI module may determine various correlations between these characteristics so as to generate a real-time treatment protocol that can be rapidly implemented to treat subjects in need thereof.

Another advantage of the system is in the identifying of trends. For instance, a computing device, e.g., server system, of the system may serve as a central repository of how subjects are experiencing and characterizing pain, how they are responding to pain remediation treatments, and what system settings and parameters are affecting pain alleviation. The AI module of the system, therefore, can mine this data to develop rules by which treatment protocols can be generated, implemented, and tested in a predictable manner. The system configurations and settings that appear to correspond to the amelioration of various pain experiences can be given greater weight than those that do not, and may therefore be used to generate rules by which to produce future treatment protocols, which can then be tested and further refined to achieve optimal effectiveness.

Hence, the system may be configured for determining one or more trends in pain reduction and/or exacerbation, and updating or otherwise changing system parameters based on the determined trends. Specifically, the system may be implemented as a rules based system that may be configured for being dynamic and evaluating the rules to be applied so as to make the overall process more efficient. Particularly, the system may evaluate the overall processes being run by the system, e.g., administration parameters employed to treat pain, against one or more characteristics, e.g., amount of reduction in pain experience, so as to determine if one or more trends can be identified whereby a change in the rules, e.g., rules governing system settings, may result in a greater effectiveness, e.g., in pain reduction, and when a change in a rule is predicted to lead to a positive response to pain treatments, then that rule may be adopted and applied when setting the pain administration parameters.

For example, where a rule has become outdated, and the system flags a discrepancy between an expected or predicted result and an observed result, such as by a rule no longer being effective, or a new rule being required, the system can automatically modify one or more of the set of rules being applied in the process in a manner so as to accommodate the new, more effective, system settings. Particularly, the system may include an artificial intelligence (AI) module that reviews one or more datasets derived by the system to make predictions as to outcomes, and can then modify the rules of the system so as to more efficiently achieve predicted outcomes.

One or more aspects or features of the subject matter described herein may be realized in digital electronic circuitry, integrated circuitry, specially designed ASICs (application specific integrated circuits), FPGAs (field programmable gated array), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to as programs, software, software applications, hardware, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (sometimes referred to as a computer program product) refers to physically embodied apparatus and/or device, such as for example magnetic discs, optical disks, memory, and Programmable Logic Devices (PLDs), used to provide machine instructions and/or data to a programmable data processor, including a machine-readable medium that receives machine instructions as a machine-readable signal.

The term "machine-readable signal" refers to any signal used to provide machine instructions and/or data to a programmable data processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT), or a liquid crystal display (LCD), or light emitting diode (LED) or (OLED) monitor for displaying information to the user and a keyboard and a pointing device, such as for example a mouse or a trackball, by which the user may provide input to the computer. In various instances, the display screen may be a capacitive sensing interactive touch-screen display. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), WiFi, and the Internet.

The computing system may include clients and servers. A client and server are generally remote from each other and typically interact through a communication network. The relationship of client and server arises by virtue of computer programs running on the respective computers and having a client-server relationship to each other. The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter.

Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. Other implementations may be within the scope of the following claims. Likewise, where a range is given, it is understood that all intermediate values in between those ranges are included therein as if individually recited.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein. Although a few embodiments have been described in detail above, other modifications are possible. Other embodiments may be within the scope of the following claims.

The invention claimed is:

1. A transcutaneous sensing and monitoring device for determining a reaction of a nerve to receipt of a magnetic stimulation applied to a target area, the transcutaneous sensing device comprising:
   a housing having a plurality of sets of opposed surfaces offset from one another by a boundary member, one opposed surface of a set of opposed surfaces forming a top surface and a corresponding other of the set of opposed surfaces forming a bottom surface, together the plurality of sets of opposed surfaces and boundary member bounding a cavity, the cavity configured for retaining one or more components of the transcutaneous sensing device;
   a first and second extended insulation layer, the first insulation layer being positioned proximate the top surface of the housing and the second insulation layer being positioned proximate the bottom surface of the housing; and
   an extended substrate layer positioned between the first and second insulation layers and being configured for determining the reaction of the nerve to receipt of the magnetic stimulation, the substrate layer comprising:
      a plurality of magnetometers positioned along a surface of the substrate layer and being arranged in a grid formation having a multiplicity of rows and columns, each magnetometer being configured for detecting the reaction in a nerve fiber to the magnetic stimulation being applied to the target area so as to produce sensed response data, the sensed response data including a first amplitude representing the reaction of the nerve fiber to the magnetic stimulation;
      a printed circuit board coupled with the plurality of magnetometers, the printed circuit board comprising a processor and a memory, the processor being configured for receiving, processing, and integrating the sensed response data to produce integrated response data; and
      an antenna for enhancing data collection and transmission,
   wherein the transcutaneous sensing and monitoring device is configured to be coupled to a portion of a subject's body proximate the target area.

2. The transcutaneous sensing and monitoring device in accordance with claim 1, further comprising a plurality of sensors, each of the plurality of sensors including at least three magnetometers of the plurality of magnetometers, wherein each sensor is configured for identifying the first amplitude with regard to one or more X, Y, and Z coordinates of the nerve so as to produce target nerve characterization data.

3. The transcutaneous sensing and monitoring device in accordance with claim 2, wherein the identifying of the first amplitude comprises determining one or more of a direction and a magnitude, and the target nerve characterization data comprises both direction data and magnitude data from at least one sensor of the plurality of sensors.

4. The transcutaneous sensing and monitoring device in accordance with claim 3, wherein at least two of the at least three magnetometers are positioned in a different row and column.

5. The transcutaneous sensing and monitoring device in accordance with claim 4, wherein the processor is configured for performing one or more of triangulation and trilateration to determine a position of the nerve fiber by integrating the target nerve characterization data from the plurality of sensors so as to produce integrated target nerve characterization data.

6. The transcutaneous sensing and monitoring device in accordance with claim 5, wherein the transcutaneous sensing and monitoring device is further configured for characterizing a reaction in a non-target nerve fiber to the magnetic stimulation being applied to the target area, so as to produce noise data.

7. The transcutaneous sensing and monitoring device in accordance with claim 6, wherein the producing of integrated targeted nerve characterization data includes removing the noise data during a triangulating or trilaterating process.

8. A system for treating neuropathic pain in a subject's body via administration of magnetic stimulation, the system comprising:
   a transcutaneous sensing and monitoring device for identifying a nerve to be treated with the magnetic stimulation, the transcutaneous sensing and monitoring device comprising:
      a housing having an extended top and bottom surface offset from one another by a bounding member, together the top surface, bottom surface, and bounding member bounding a cavity for retaining one or more components of the transcutaneous sensing device;
      a plurality of extended insulation layers, a first insulation layer of the plurality of extended insulation layers being positioned proximate the top surface and a second insulation layer of the plurality of extended insulation layers being positioned proximate the bottom surface; and
      an extended substrate layer positioned between the plurality of insulation layers, the substrate layer comprising:
         a plurality of sensors positioned along one or more surfaces of the substrate layer and being configured for detecting a reaction in one or more nerve fibers to the receipt of the magnetic stimulation being applied to a target area of a subject's body so as to produce response data,
      a printed circuit board coupled with the plurality of sensors, the printed circuit board comprising a processor, and a memory, the processor being configured for receiving and processing the response data to produce processed response data, the processed response data including a characterization of an identified nerve to be treated, and
      an antenna for enhancing data collection and transmission, wherein the transcutaneous sensing and monitoring device is configured to be coupled to a portion of the subject's body proximate the target area; and
   a transcutaneous magnetic stimulation (tMS) application device for delivering focused magnetic stimulation to the identified nerve, the tMS application device comprising:
      a housing having an extended body, the extended body including a proximate portion having a proximate end, and a distal portion having a distal end, the extended body defining a cavity for retaining one or more components of the tMS device, and
      an insulated magnetic coil disposed within the cavity of the proximate portion of the extended body of the housing, the magnetic coil having a figure-8 arrangement and including braiding wrapped around a figure-8 portion of the coil, the magnetic coil being configured for generating and delivering a focused magnetic stimulation at a determined pulse rate and having a determined amplitude, the focused magnetic stimulation being defined by a voltage and a current,
   controller, the controller including:
      a memory for storing the processed response data, the characterization of the identified nerve, and one or more treatment protocols, and
      a control processor, coupled to the memory, the control processor configured to access the processed response data and the characterization of the identified nerve, and determine the one or more treatment protocols, the one or more treatment protocols defining one or more application parameters and one or more delivery characteristics, the one or more application parameters including:
         a voltage level and a current level for generating a magnetic pulse of the magnetic stimulation,
         a frequency and duration of the magnetic pulse to be generated, and
         the one or more delivery characteristics including a set of coordinates defining the nerve to be treated and an orientation for orienting the tMS application device relative to the target area; and
   a positioning element having a proximal portion including a proximal end, and a distal portion including a distal end, the distal portion of the positioning element being coupled to the transcutaneous magnetic stimulation (tMS) application device proximate the distal end of the positioning element, the positioning element being composed of a plurality of articulating arm members, a plurality of the arm members being coupled together by an automating element, the automating element for positioning and orienting the tMS application device proximate the treatment area in accordance with the orientation.

9. The system in accordance with claim 8, wherein the plurality of sensors of the transcutaneous sensing and monitoring device comprise magnetometers, the magnetometers having a grid configuration including both rows and columns.

10. The system in accordance with claim 9, wherein the plurality of sensors include at least three magnetometers, wherein any set of three magnetometers from the at least three magnetometers form a sensor, of the plurality of sensors, the sensor being configured for performing one or more of triangulation and trilateration to determine a portion of a target nerve based on a reaction of the target nerve to a receipt by the target nerve of the magnetic stimulation.

11. The system in accordance with claim 10, wherein the one or more of the triangulation or the trilateration involves identifying a first amplitude produced in the target nerve by a receipt by the target nerve of the magnetic stimulation with regard to one or more X, Y, and Z coordinates of the target nerve so as to produce nerve characterization data.

12. The system in accordance with claim 11, wherein the one or more treatment protocols includes instructions for orienting the tMS application device proximate the target area, the orienting of the tMS application device being based on the nerve characterization data such that an orientation of the tMS application device corresponds to an orientation of the target nerve.

13. The system in accordance with claim 12, wherein the positioning element is configured for autonomously positioning and orienting the tMS application device in a determined orientation proximate the target area.

14. The system in accordance with claim 13, wherein the system further comprises a movement sensor for detecting a movement of the target area, whereby any movement of the target area evokes a corresponding movement in the tMS application device so as to maintain the determined orientation relative to the target nerve.

15. A system for identifying one or more characteristics of a neuropathic nerve to be targeted with an application of a focused magnetic stimulation so as to ameliorate neuropathic pain experience, the system comprising:
   a transcutaneous sensing and monitoring device having a plurality of sensors in a grid including both rows and columns of sensors, each sensor being configured for identifying a reaction of the neuropathic nerve in response to the application of the focused magnetic stimulation so as to produce raw reaction data;
   a computing device, coupled to the transcutaneous sensing and monitoring device, the computing device being configured for receiving the raw reaction data, evaluating the raw reaction data, and determining one or more characteristics of the neuropathic nerve to be targeted for treatment by the application of the focused magnetic stimulation, the computing device comprising:
      a first processing engine for receiving raw reaction data from a first unit of sensors of the plurality of sensors, the first unit including a first set of at least three sensors of the plurality of sensors, the raw reaction data including magnitude data and orientation data from each sensors of the first unit and defining characteristics of a response of the neuropathic nerve to the applied focused magnetic stimulation, the first processing engine for integrating the magnitude data and the orientation data from each of the sensors of the first unit, and for determining a first integrated magnitude and a first integrated orientation for the first unit;
      a second processing engine for receiving raw reaction data from a second unit of sensors of the plurality of sensors, the second unit including a second set of at least three sensors of the plurality of sensors and the raw reaction data including second magnitude data and second orientation data from each sensor of the second unit and further defining characteristics of the response of the neuropathic nerve, the second processing engine for integrating the magnitude data and the orientation data from each of the sensors of the second unit, and for determining a second integrated magnitude and a second integrated orientation for the second unit;
      a third processing engine for receiving the first and second integrated magnitude, determining which sensor evidences a greater magnitude, and associating a greater weight to the sensor evidencing the greater magnitude;
      a fourth processing engine for receiving the first and second integrated orientation and associating a greater weight to whichever orientation is correlated with the unit evidencing the greater magnitude;
      a fifth processing engine for receiving and evaluating respective integrated magnitude, integrated orientation, and weight data for the plurality of sensors, and determining a set of coordinates defining the neuropathic nerve to be targeted in a treatment area based on the evaluated respective integrated magnitude, integrated orientation, and weight data; and
      a sixth processing engine for determining a first treatment protocol for administering the focused magnetic stimulation to the neuropathic nerve to be targeted so as thereby ameliorate neuropathic pain experience, the first treatment protocol including an orientation of a tMS application device relative to the neuropathic nerve to be treated in the target area and an amplitude of the focused magnetic stimulation to be administered.

16. The system in accordance with claim 15, further comprising a transcutaneous magnetic stimulation (tMS) application device configured for delivering the focused magnetic stimulation to the neuropathic nerve to be targeted.

17. The system in accordance with claim 16, further comprising a positioning element, the positioning element being coupled to the tMS application device and including a plurality of articulating arm members, a plurality of the arm members being coupled together by an automating element, the automating element for positioning and orienting the tMS application device proximate the treatment area in accordance with the orientation of the first treatment protocol.

18. The system in accordance with claim 17, wherein the tMS application device includes a controller comprising a processor and memory, the processor configured for controlling generation of the focused magnetic stimulation of the tMS application device with respect to one or more of a waveform to be produced by the tMS application device and voltage and current employed in producing the waveform.

19. The system in accordance with claim 18, wherein the transcutaneous sensing and monitoring device is further configured for sensing a response in the neuropathic nerve being targeted with magnetic stimulation to produce target nerve response data, and the computing device is configured for changing, based on the target nerve response data, one or more of the orientation of the tMS application device or an amplitude of the waveform produced.

20. The system in accordance with claim 19, wherein the system further comprises a movement sensor for detecting a movement of the target area, whereby the detection, by the movement sensor, of any movement of the target area evokes a corresponding movement in the tMS application device so as to maintain the orientation of the tMS application device relative to the target nerve.

* * * * *